United States Patent
Fatatis et al.

(10) Patent No.: US 10,414,771 B2
(45) Date of Patent: Sep. 17, 2019

(54) COMPOUNDS USEFUL FOR INHIBITING METASTASIS FROM CANCER AND METHODS USING SAME

(71) Applicants: Drexel University, Philadelphia, PA (US); Alliance Discovery, Inc., Doylestown, PA (US)

(72) Inventors: Alessandro Fatatis, Penn Valley, PA (US); Joseph M. Salvino, Chester Springs, PA (US); Olimpia Meucci, Penn Valley, PA (US); Whitney L. Gladney, Glenolden, PA (US)

(73) Assignees: Drexel University, Philadelphia, PA (US); Alliance Discovery, Inc., Doylestown, PA (US)

( * ) Notice: Subject to any disclaimer, the term of this patent is extended or adjusted under 35 U.S.C. 154(b) by 0 days.

(21) Appl. No.: 15/821,184

(22) Filed: Nov. 22, 2017

(65) Prior Publication Data
US 2018/0099972 A1    Apr. 12, 2018

Related U.S. Application Data

(63) Continuation of application No. 15/174,227, filed on Jun. 6, 2016, now Pat. No. 9,856,260, which is a continuation of application No. 13/776,220, filed on Feb. 25, 2013, now Pat. No. 9,375,474, which is a continuation of application No. 13/312,540, filed on Dec. 6, 2011, now Pat. No. 8,435,993.

(60) Provisional application No. 61/420,640, filed on Dec. 7, 2010.

(51) Int. Cl.
| | | |
|---|---|---|
| C07D 487/04 | (2006.01) | |
| A61K 31/451 | (2006.01) | |
| A61K 31/453 | (2006.01) | |
| A61K 31/7088 | (2006.01) | |
| A61K 39/395 | (2006.01) | |
| C07D 403/04 | (2006.01) | |
| C07K 16/28 | (2006.01) | |

(52) U.S. Cl.
CPC .......... *C07D 487/04* (2013.01); *A61K 31/451* (2013.01); *A61K 31/453* (2013.01); *A61K 31/7088* (2013.01); *A61K 39/3955* (2013.01); *C07D 403/04* (2013.01); *C07K 16/28* (2013.01)

(58) Field of Classification Search
CPC combination set(s) only.
See application file for complete search history.

(56) References Cited

U.S. PATENT DOCUMENTS

| | | |
|---|---|---|
| 3,939,159 A | 2/1976 | Dornauer et al. |
| 5,405,847 A | 4/1995 | Dieter et al. |
| 8,435,993 B2 | 5/2013 | Salvino et al. |
| 2002/0010125 A1 | 1/2002 | Carson et al. |
| 2006/0115834 A1 | 6/2006 | Racila et al. |
| 2007/0142386 A1 | 6/2007 | Nordvall et al. |
| 2008/0214578 A1 | 9/2008 | Nordvall et al. |
| 2010/0069396 A1 | 3/2010 | Zhang et al. |
| 2010/0105667 A1 | 4/2010 | Furet et al. |
| 2010/0216726 A1 | 8/2010 | Fuchino et al. |

FOREIGN PATENT DOCUMENTS

| | | |
|---|---|---|
| EP | 584487 A2 | 3/1994 |
| JP | 6076913 B2 | 2/2017 |
| WO | 0160406 A1 | 8/2001 |
| WO | 2004045526 A2 | 6/2004 |
| WO | 2005033115 A1 | 4/2005 |
| WO | 2005086971 A2 | 9/2005 |
| WO | 2008039139 A1 | 4/2008 |
| WO | 2009109616 A2 | 9/2009 |
| WO | 2009120140 A1 | 10/2009 |
| WO | 2011127333 A2 | 10/2011 |

OTHER PUBLICATIONS

Codding, Acta Cryst, 2005, A61, C329, p. 08.08.6.
International Search Report, issued in corresponding application, No. PCT/US11/63533 dated Jun. 12, 2012.
Metastatic Cancer (http://www.cancer.gov/cancertopics/factsheet/Sites-Types/metastastic), 2014.
Supplementary Partial European Search Report for 11847605.0 dated Oct. 1, 2015.
Aguirre-Ghiso, "Models, mechanisms and clinical evidence for cancer dormancy", Nature Reviews/Cancer, 7, Nov. 2007, 834-846.
Coffey, et al., "Cancer surgery: risks and opportunities", BioEssays, 28, 2006, 433-437.
Coffey, et al., "Excisional surgery for cancer cure: therapy at a cost", Lancet Oncol, 4, Dec. 2003, 760-768.
Deng, et al., "CXCR6/CXCL16 functions as a regulator in metastasis and progression of cancer", Biochimica et Biophysica Acta, 1806, Feb. 2010, 42-49.
Fatatis, Kerberos Biopharmaceuticals Inc., Oct. 2014.
Gassmann, et al., "CXCR4 Regulates the Early Extravasation of Metastatic Tumor Cells In Vivo", Neoplasia, 11(7), Jul. 2009, 651-661.

(Continued)

*Primary Examiner* — Umamaheswari Ramachandran
(74) *Attorney, Agent, or Firm* — Saul Ewing Arnstein & Lehr LLP; Kathryn Doyle; Domingos J. Silva

(57) ABSTRACT

The present invention includes compositions that are useful in preventing or treating metastasis in a subject diagnosed with cancer. The present invention also includes methods of preventing or treating metastasis in a subject diagnosed with cancer, wherein the method comprises administering to the subject in need thereof an effective amount of a pharmaceutical formulation comprising at least one pharmaceutically acceptable carrier and at least one $CX_3CR1$ or fractalkine antagonist.

2 Claims, 14 Drawing Sheets

Specification includes a Sequence Listing.

(56) References Cited

OTHER PUBLICATIONS

Gassmann, et al., "The tumor cell-host organ interface in the early onset of metastatic organ colonisation", Clin Exp Metastasis, 25, 2008, 171-181.

Hesselgesser, et al., "Identification and characterization of small molecule functional antagonists of the CCR1 chemokine receptor", J Biol Chem. 273(25), Jun. 1998, 15687-15692.

Huang, et al., "Chemokines and hepatocellular carcinoma", World J Gastroenterol, 16(15), Apr. 2010, 1832-1836.

Hulshof, et al., "Synthesis and pharmacological characterization of novel inverse agonists acting on the viral-encoded chemokine receptor US28", Bioorg Med Chem. 14(21), Nov. 1, 2006, 7213-7230.

Hüsemann, et al., "Systemic Spread is an Early Step in Breast Cancer", Cancer Cell, 13, Jan. 2008, 58-68.

Izraely, et al., "Chemokine-chemokine receptor axes in melanoma brain metastasis", Immunology Letters, 130, 2010, 107-114.

Jamieson, et al., "CX3CR1 Is Expressed by Prostate Epithelial Cells and Androgens Regulate the Levels of CX3CL1/Fractalkine in the Bone Marrow: Potential Role in Prostate Cancer Bone Tropism", Cancer Res, 68(6), Mar. 2008, 1715-1722.

Koizumi, et al., "Role of CX3CL1/Fractalkine in Osteoclast Differentiation and Bone Resorption", J. Immunol. 183, Nov. 2009, 7825-7831.

Mantovani, et al., "The chemokine system in cancer biology and therapy", Cytokine & Growth Factor Reviews, 21, 2010, 27-39.

Marchesi, et al., "The Chemokine Receptor CX3CR1 Is Involved in the Neural Tropism and Malignant Behavior of Pancreatic Ductal Adenocarcinoma", Cancer Res. 68(21), Nov. 2008, 9060-9069.

Mühlbauer, et al., "Lack of association between the functional CX3CR1 polymorphism V249I and hepatocellular carcinoma", Oncol Rep.13(5), May 2005, 957-963 (Abstract Only).

Nashan, et al., "Cutaneous metastases of visceral tumours: a review", J Cancer Res Clin Oncol. 135(1), Jan. 2009, 1-14.

Naya, et al., "Design, synthesis, and discovery of a novel CCR1 antagonist", J Med Chem. 44(9), Apr. 26, 2001, 1429-1435.

Nevo, et al., "The involvement of the fractalkine receptor in the transmigration of neuroblastoma cells through bone-marrow endothelial cells", Cancer Letters, 273, 2009, 127-139.

Ng, et al., "Discovery of Novel Non-Peptide CCR1 Receptor Antagonists", J. Med. Chem. 42, Jun. 1999, 4680-4694.

Russell, et al., "The α-receptor for platelet-derived growth factor as a target for antibody-mediated inhibition of skeletal metastases from prostate cancer cells", Oncogene, 28, 2009, 412-421.

Savarin-Vuaillat, et al., "Chemokines and Chemokine Receptors in Neurological Disease: Raise, Retain, or Reduce?", Neurotherapeutics: The Journal of the American Society for Experimental NeuroTherapeutics, 4, Oct. 2007, 590-601.

Schön, et al., J Natl Cancer Inst. 95(15), Aug. 2003, 1138-1149.

Shen, et al., "A small-molecule antagonist of CX3CR1 impairs homing and colonization of breast cancer cells in the skeleton", Proceedings of the 106th Annual Meeting of the American Association for Cancer Research; Apr. 18-22, 2015; Philadelphia, PA; Cancer Res. 75 (15 Suppl), 2015, Abstract.

Shulby, et al., "CX3CR1-fractalkine expression regulates cellular mechanisms involved in adhesion, migration, and survival of human prostate cancer cells", Cancer Res. 64(14), Jul. 15, 2004, 4693-4698.

Stroke, et al., "Identification of CXCR3 receptor agonists in combinatorial small-molecule libraries", Biochemical and Biophysical Research Communications, 349, 2006, 221-228.

Stuelten, et al., "Acute Wounds Accelerate Tumorigenesis by a T Cell-Dependent Mechanism", Cancer Res. 68 (18), Sep. 2008, 7278-7282.

Trivedi, et al., "Chapter 17. Chemokines: Targets for Novel Therapeutics", Annual Reports in Medicinal Chemistry 35, Jan. 1, 2000, 191-200.

Valastyan, et al., "Tumor metastasis: molecular insights and evolving paradigms", Cell. 147(2), Oct. 2011, 275-292.

Walters, et al., "Evaluation of a series of bicyclic CXCR2 antagonists", Bioorganic & Medicinal Chemistry Letters, 18, 2008, 798-803.

Yang, et al., "Synthesis and anti-leukemia activity mensuration of 1-phenethyl-4-hydroxy-4-substituted of bis[1-phenethyl-4-hydroxy-4-(3-flurophenyl) piperidinium hydrochloride] studied by X-ray and DFT methods", Journal of Molecular Structure 929, Jul. 16, 2009, 97-104.

Yu, et al., "Defective antitumor responses in CX3CR1-deficient mice", Int J Cancer. 121(2), Jul. 15, 2007, 316-22.

RFU (Change in RFU) = Peak - Baseline

% Increase in RFU = (Peak - Baseline) / Baseline x 100

COMPOUNDS USEFUL FOR INHIBITING METASTASIS FROM CANCER AND METHODS USING SAME

CROSS-REFERENCE TO RELATED APPLICATIONS

The present application is a continuation application of, and claims priority to, U.S. patent application Ser. No. 15/174,227, filed Jun. 6, 2016, now allowed, which is a continuation of, and claims priority to, U.S. patent application Ser. No. 13/776,220, filed Feb. 25, 2013, now issued as U.S. Pat. No. 9,375,474, which is a continuation of, and claims priority to, U.S. patent application Ser. No. 13/312,540, filed Dec. 6, 2011, now issued as U.S. Pat. No. 8,435,993, which claims priority under 35 U.S.C. § 119(e) to U.S. Provisional Application No. 61/420,640, filed Dec. 7, 2010, all of which applications are hereby incorporated by reference in their entireties herein.

STATEMENT REGARDING FEDERALLY SPONSORED RESEARCH OR DEVELOPMENT

This invention was made with government support under grant number W81XWH-09-1-0593 awarded by the Department of Defense/US Army (Breast Cancer Program) and under grant number DA015014 awarded by the National Institutes of Health. The government has certain rights in the invention.

BACKGROUND OF THE INVENTION

Metastasis or metastatic disease is the spread of a disease from one organ or part to another non-adjacent organ or part. Metastatic disease is primarily but not uniquely associated with malignant tumor cells and infections (Klein, 2008, Science 321(5897):1785-88; Chiang & Massagué, 2008, New Engl. J. Med. 359(26):2814-23).

Cancer occurs after a single cell in a tissue is genetically damaged in ways that result in the formation of a putative cancer stem cell possessing a malignant phenotype. These cancer stem cells are able to undergo uncontrolled abnormal mitosis, which serves to increase the total number of cancer cells at that location. When the area of cancer cells at the originating site become clinically detectable, it is called primary tumor. Some cancer cells also acquire the ability to penetrate and infiltrate surrounding normal tissues in the local area, forming a new tumor. The newly formed tumor in the adjacent site within the tissue is called a local metastasis.

Some cancer cells acquire the ability to penetrate the walls of lymphatic and/or blood vessels, after which they are able to circulate through the bloodstream (circulating tumor cells) to other sites and tissues in the body. This process is known (respectively) as lymphatic or hematogenous spread. After the tumor cells come to rest at another site, they re-penetrate through the vessel or walls (extravasation), continue to multiply, and eventually another clinically detectable tumor is formed. This new tumor is known as a metastatic (or secondary) tumor. Metastasis is one of the hallmarks of malignancy. Most tumors and other neoplasms can metastasize, although in varying degrees (e.g. basal cell carcinoma rarely metastasize) (Kumar et al., 2005, "Robbins and Cotran Pathologic Basis of Disease", 7th ed., Philadelphia: Elsevier Saunders).

Metastatic tumors are very common in the late stages of cancer. The most common places for the metastases to occur are the lungs, liver, brain, and the bones. There is also a propensity for certain tumors to seed in particular organs. For example, prostate cancer usually metastasizes to the bones. In a similar manner, colon cancer has a tendency to metastasize to the liver. Stomach cancer often metastasizes to the ovary in women. Breast tumor cells often metastasize to bone tissue. Studies have suggested that these tissue-selective metastasis processes are due to specific anatomic and mechanical routes.

Currently, only six percent of women that are first diagnosed with breast adenocarcinoma present with metastases (Hortobagyi et al., "Neoplasm of the breast". In: Cancer Medicine. B C Decker; Holland-Frei, Ed., 2006, p. 1584-643). Unfortunately, between twenty and fifty percent of them will eventually develop metastatic disease (Hortobagyi et al., "Neoplasm of the breast". In: Cancer Medicine. B C Decker; Holland-Frei, Ed., 2006, p. 1584-643) Metastases are responsible for an intolerably high number of deaths among patients that would otherwise be almost invariably cured by surgical resection and adjuvant therapy (Lu et al., 2009, Cancer Res. 69:4951-53). Autopsy studies have estimated that 70% of advanced breast cancer patients have skeletal metastases (Bussard et al., 2008, Cancer Met. Rev. 27:41-55). These secondary bone tumors cause significant morbidity, leading to considerable pain, spinal cord compression and pathological fractures (Coleman, 1997, Cancer 80:1588-94). In addition, when breast cancer cells have disseminated to the skeleton, the resulting bone tumors can be treated only with palliative measures (Body & Mancini, 2002, Off. J. Multi-Natl. Assoc. Supp. Care Cancer 10:399-407; Coleman et al., 2008, Clin. Cancer Res. 14:6387-95; Costa & Major, 2009, Nat. Clin. Pract. Oncol. 6:163-74). The majority of patients develop metastases years after initial treatment of the primary breast tumor. The appearance of late metastases can indeed be attributed to cancer cells disseminated to secondary tissues during different stages of primary tumor progression and remained dormant for variable periods of time. In fact, both early dissemination and dormancy of tumor cells are supported by strong evidence (Huseman et al., 2008, Cancer Cell 13:58-68; Aguirre-Ghiso, 2007, Nat. Rev. Cancer 7:834-46).

Due to the limited size of breast tumors that are first diagnosed today, the vast majority of patients are considered to be viable candidates for breast-conserving surgery (BCS) or lumpectomy. Since BCS minimizes the physical and psychological impact of breast surgery, this approach is widely preferred by patients (Veronesi et al., 2005, Lancet, 365:17271; Morrow, 2009, BMJ 338:b557). In addition, based on studies that reported comparable survival rates between lumpectomy and more radical approaches such as mastectomy, oncologic surgeons are also in favor of this form of treatment (Veronesi et al., 2002, N. Engl. J. Med. 347:1227; Fisher et al., 2002, N. Engl. J. Med. 347:1233). However, the conclusions of these studies are being challenged by a meta-analysis showing that for every four local recurrences prevented, one breast cancer death could be avoided (Clarke et al., 2005, Lancet, 366:2087). In fact, following lumpectomy only 37% of breasts are found tumor-free and between 22% and 59% of patients will need re-intervention because positive or close margins are detected (Sabel et al., 2009, J. Surg. Oncol. 99:99). In addition, reexcision or adjuvant therapies, such as local irradiation or chemotherapy, are normally started several weeks or even months after primary surgery (Buchholz, 2009, N. Engl. J. Med. 360:63; Balduzzi et al., 2010, Cancer Treat. Rev. 36:443) to allow for complete patient's recovery and improve post-operatory aesthetic results.

However, the stroma at the site of tumor removal is characterized by altered angiogenesis, immune cells infiltration and activation of cancer-associated fibroblasts (Hofer et al., "Wound-induced tumor progression: a probable role in recurrence after tumor resection," Archives of Surgery (Chicago, Ill.: 1960), 133, 383, 1998; Stuelten et al., 2008, Cancer Res. 68:7278). These events are potentially able to promote perioperative proliferation and motility of residual cancer cells, thereby allowing their escape into the circulation (Coffey et al., 2006, BioEssays, 28:433; Coffey et al., 2003, Lancet Oncol. 4:760). Even in the presence of dormant cancer cells already lodged into distant sites, the additional spreading of these cells would produce new waves of micrometastases.

The arrest of circulating cancer cells to the skeleton is highly dependent on specific adhesive interactions with the endothelial cells lining the marrow sinusoids (Lehr & Pienta, 1998, J. Natl. Cancer Inst. 90:118-23; Scott et al., 2001, Br. J. Cancer 84:1417; Glinskii et al, 2005, Neoplasia 7:522-27). The required next step is the extravasation of adherent cancer cells drawn by chemo attractant cues generated by the surrounding stroma (Liotta, 2001, Nature 410:24-25). The similarities between cancer cell dissemination and leukocyte trafficking lead to the identification of chemokines as crucial players in both sets of events (Mantovani et al., 2010, Cyt. & Growth Factor Rev. 21:27-39).

The interactions between the chemokine CXCL12 (SDF-1) and its receptor CXCR4 have been extensively studied (Müller et al., 2001, Nature 410:50-56; Dewan et al., 2006, Biomed Pharmacother. 60:273-76). The role of CXCR4 in cell adhesion appears to be dependent on the secondary induction of αvβ3 integrin presentation on the surface of cancer cells and consequent binding to vascular adhesion molecules (Engl et al., 2006, Neoplasia 8:290-301). However, CXCR4 inhibition did not block the binding of colon cancer cells to the liver endothelium, but did limit extravasation (Gassman et al., 2009, Neoplasia 11:651-61). Thus, similarly to its role in hematopoietic stem cells homing, the soluble chemokine CXCL12 seems to be an important player in cancer cell migration into the bone microenvironment rather than mediating adhesive interactions with CXCR4-bearing cells (Gassman, 2008, Clin. Exp. Metastasis 25:171-81).

CX3C chemokine receptor 1 ($CX_3CR1$), also known as the fractalkine receptor or G-protein coupled receptor 13 (GPR13), is a protein that in humans is encoded by the $CX_3CR1$ gene (Robertson, 2002, J. Leukoc. Biol. 71(2): 173-83; Raport et al., 1995, Gene 163(2):295-99). This receptor binds the chemokine $CX_3CL1$ (also called neurotactin or fractalkine or FKN). FKN is a transmembrane protein that is cleaved into a soluble molecule with potent chemoattractant properties (Bazan et al., 1997, Nature 385: 640-44). In its membrane-bound form, FKN can establish strong and stable adhesive interactions with its receptor $CX_3CR1$, and does not require any downstream signaling to induce activation of additional adhesion molecules (Haskell et al., 1999, J. Biol. Chem. 274:10053-58; Imai et al., 1997, Cell. 91:521-30; Goda et al., 2000, J. Immun. 64:4313). Prostate cancer cells were shown to express $CX_3CR1$ and, under dynamic-flow conditions, to adhere to human bone marrow endothelial cells in a FKN-dependent manner (Shulby et al., 2004, Cancer Res. 64:4693-98). In addition, $CX_3CR1$ was shown to be expressed in a high percentage of prostate cancer tissues while human bone marrow supernatants contain soluble FKN, which is released from cells of the bone stroma through a mechanism regulated by androgens (Jamieson et al., 2008, Cancer Res. 68:1715-22). A role for the FKN/$CX_3CR1$ pair in metastasis is also supported by the observation that there is a correlation between $CX_3CR1$ expression in primary breast tumors and clinical metastases. In addition, $CX_3CR1$ expression in pancreatic tumor cells was found to promote the infiltration of the central nervous system (Marchesi et al., 2008, Cancer Res. 68:9060-69). Finally, FKN and $CX_3CR1$ have been recently reported to be involved in adhesion of neuroblastoma cells to the bone in an in vitro system (Nevo et al., 2009, Cancer Lett. 273:127-39).

$CX_3CR1$ was previously detected in the epithelial compartment of normal and malignant human prostate gland tissues (Shulby et al., 2004, Cancer Res. 64:4693; FIG. 1). FKN was also detected both in the soluble fraction of human bone marrow (~2 ng/ml) and on the surface of human bone marrow endothelial cells (Jamieson et al., 2008, Cancer Res. 68:1715). Human tissue microarrays containing 172 samples of breast cancer were examined, and 131 were found to be positive for $CX_3CR1$ expression (FIG. 2). Because of the high propensity shown by several solid tumors, including breast cancer, to target the skeleton, these results support the idea that functional interactions between FKN in the bone and $CX_3CR1$ on cancer cells are involved in skeletal metastasis. This model was strengthened by the detection of $CX_3CR1$ also in several human breast cancer cell lines; the superior ability of MDA-231 cells to arrest at the skeleton through the blood circulation of mice was related to $CX_3CR1$ expression as compared to other cell lines such as MDA-436 that fail to express this receptor (FIG. 3).

Despite the extensive research on the mechanisms of cancer metastasis, there is not a validated and effective approach to minimize the development of metastasis in patients afflicted with primary tumors. There is a need in the art to identify a method of treatment that efficiently avoids, delays or minimizes the development of metastatic tumors in patients, especially in the context of metastatic bone cancer associated with primary prostate or breast cancers. The present invention fulfills these needs.

BRIEF SUMMARY OF THE INVENTION

The invention includes a composition comprising at least one agent selected from the group consisting of:

(i) a compound of Formula (I):

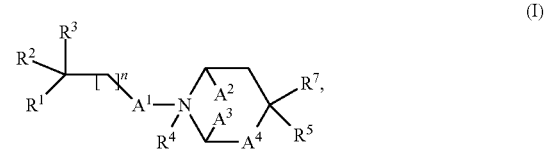

wherein in (I):

$A^1$ is $CH_2$ or cyclopentane-1,3-diyl;

n is 0, 1, 2, 3, 4 or 5 if A is $CH_2$, or n is 0, 1, or 2 if A is cyclopentane-1,3-diyl;

$A^2$ and $A^3$ are both H, or $A^2$ and $A^3$ combine to form a divalent radical selected from the group consisting of methanediyl, ethane-1,2-diyl, or propane-1,3-diyl;

$A^4$ is $CH_2$, $CH(CF_3)$, or $CF_2$;

$R^1$ and $R^2$ are both H, and $R^3$ is selected from the group consisting of:

wherein ring A is selected from the group consisting of phenyl, substituted phenyl, pyridinyl, substituted pyridinyl, thiophenyl, substituted thiophenyl, 1H-pyrazole, and 1-($C_1$-$C_6$) alkyl-1H-pyrazole;

$R^4$ is nil or ($C_1$-$C_6$)alkyl, wherein if $R^4$ is ($C_1$-$C_6$)alkyl, compound of Formula (I) is a quaternary ammonium salt;

$R^5$ is ($C_1$-$C_6$)alkyl, substituted ($C_1$-$C_6$)alkyl, phenyl, substituted phenyl, heteroaryl, substituted heteroaryl;

$R^6$ is H, ($C_1$-$C_6$)alkyl, substituted ($C_1$-$C_6$)alkyl, aryl or substituted aryl; and, $R^7$ is OH, $CH_2OH$, or $C(=O)OR^6$;

(ii) a compound of Formula (IX):

$$R^A\!-\!R^B \quad \text{(IX), wherein:}$$

$R^A$ is a group selected from the group consisting of:

and, $R^B$ is a group selected from the group consisting of:

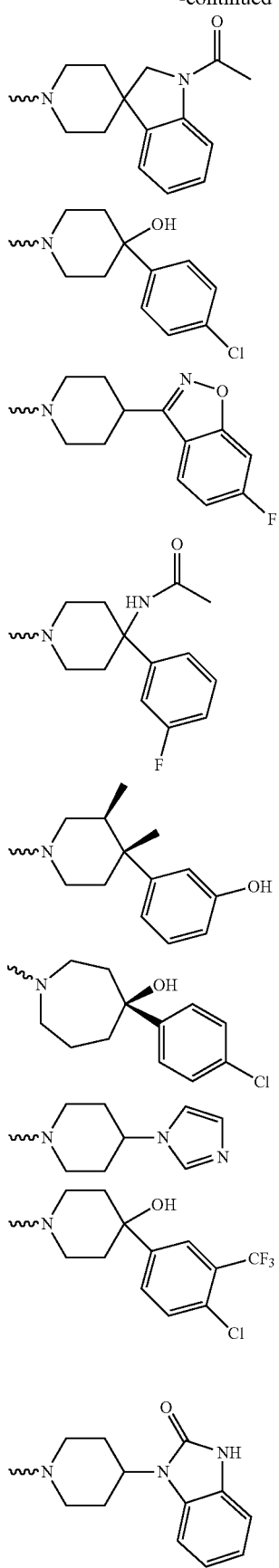
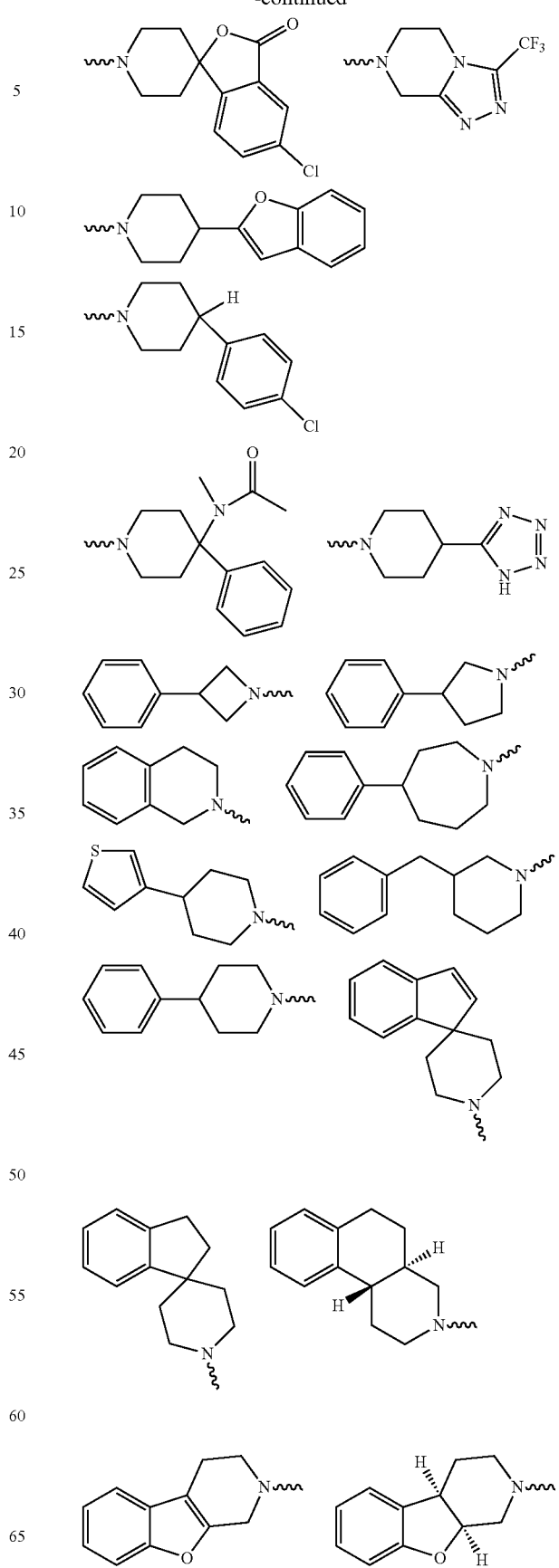

-continued

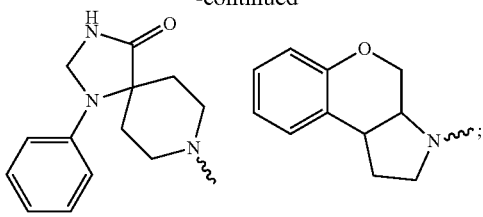

(iii) a compound of Formula (X):

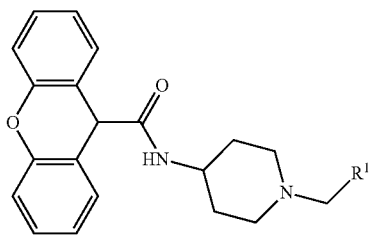
(X)

wherein R¹ is $(C_1-C_8)$ alkyl, substituted $(C_1-C_8)$ alkyl, phenyl, substituted phenyl, $(C_1-C_8)$ cycloalkyl or substituted $(C_1-C_8)$ cycloalkyl;

(iv) a compound of Formula (XI):

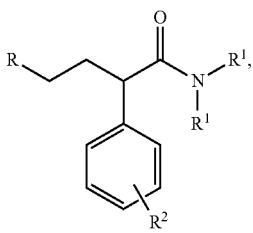
(XI)

wherein

R is selected from the group consisting of:

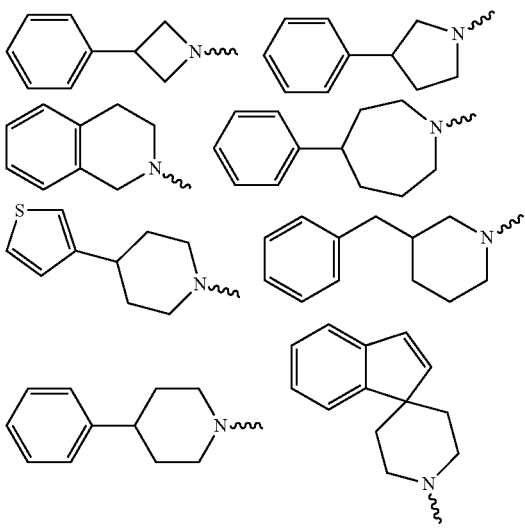

-continued

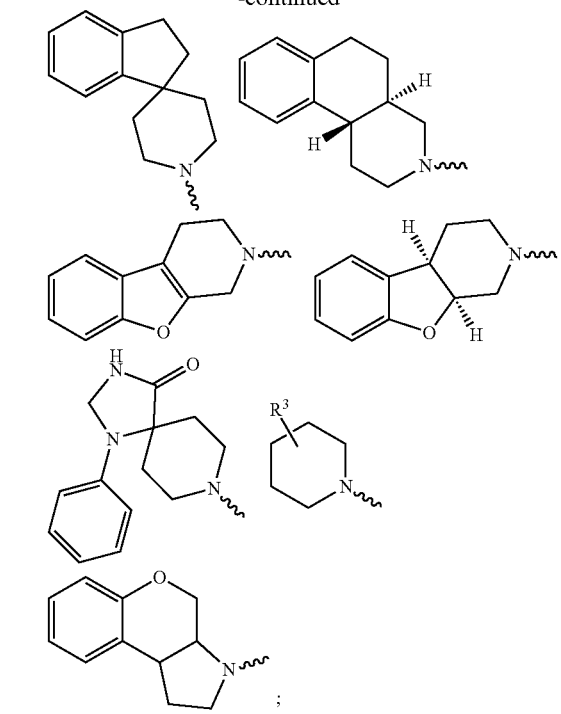

each occurrence of $R^1$ and $R^4$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

(v) a compound of Formula (XII):

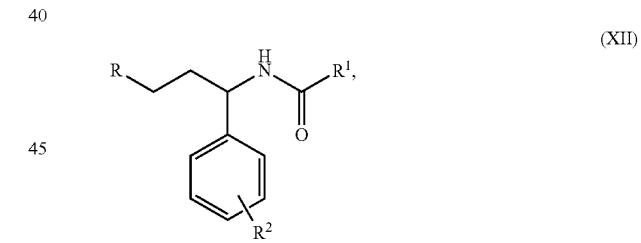
(XII)

wherein

R is selected from the group consisting of:

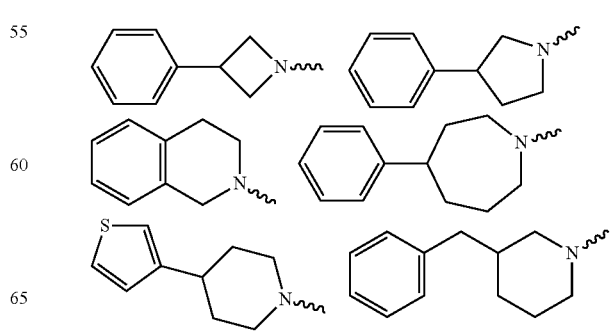

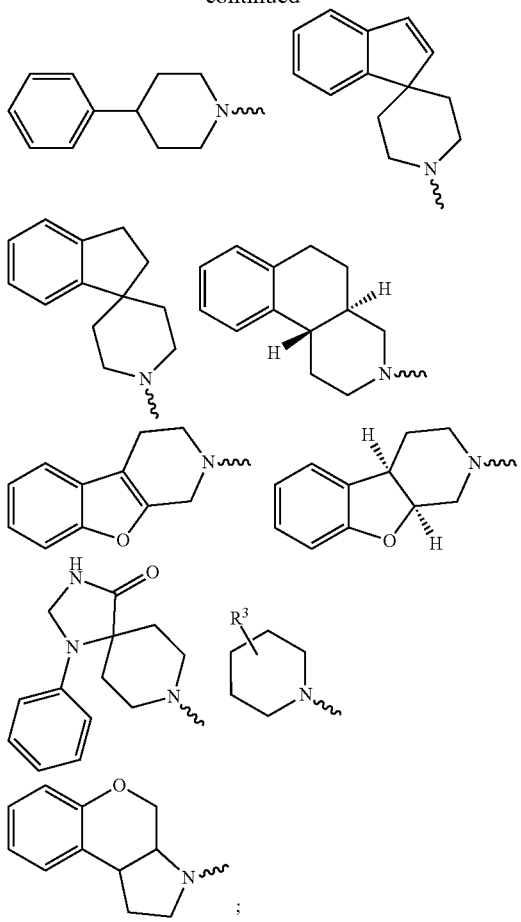

each occurrence of $R^1$, $R^4$ and $R^5$ is independently H, ($C_1$-$C_6$) alkyl, substituted ($C_1$-$C_6$) alkyl, phenyl, substituted phenyl, ($C_1$-$C_6$) cycloalkyl, or substituted ($C_1$-$C_6$) cycloalkyl; and, $R^2$ and $R^3$ are independently H, ($C_1$-$C_6$) alkyl, substituted ($C_1$-$C_6$) alkyl, phenyl, substituted phenyl, ($C_1$-$C_6$) cycloalkyl, substituted ($C_1$-$C_6$) cycloalkyl, halo, $OR^4$, $N(R^4)$ ($R^4$), $NO_2$, or NHAc;

(vi) a $CX_3CR1$ or fractalkine antibody; and combinations thereof, and a pharmaceutically acceptable salt thereof.

In one embodiment, the at least one agent is selected from the group consisting of: 5-(3-(4-(4-chlorophenyl)-4-hydroxypiperidin-1-yl)propyl)pyrrolo[1,2-a]quinoxalin-4 (5H)-one; 5-(3-(4-(4-chlorophenyl) piperidin-1-yl)propyl) pyrrolo[1,2-a]quinoxalin-4(5H)-one; combinations thereof, and a salt thereof. In another embodiment, the composition further comprises at least one pharmaceutically acceptable carrier. In yet another embodiment, the antibody comprises an antibody selected from a polyclonal antibody, a monoclonal antibody, a humanized antibody, a synthetic antibody, a heavy chain antibody, a human antibody, a biologically active fragment of an antibody, and combinations thereof.

The invention also includes a method of preventing or treating metastasis in a subject diagnosed with cancer. The method comprises administering to the subject in need thereof an effective amount of a pharmaceutical formulation comprising at least one pharmaceutically acceptable carrier and at least one $CX_3CR1$ or fractalkine antagonist.

In one embodiment, the subject is subjected to primary surgery related to the cancer. In another embodiment, administering the pharmaceutical formulation takes place before, during or after the primary surgery. In yet another embodiment, the cancer comprises a solid cancer. In yet another embodiment, the solid cancer is selected from the group consisting of breast cancer and prostate cancer. In yet another embodiment, the metastasis comprises bone metastasis. In yet another embodiment, the administering starts at least 6 months before the primary surgery. In yet another embodiment, the administering starts at least 3 months before the primary surgery. In yet another embodiment, the administering starts at least 1 month before the primary surgery. In yet another embodiment, the administering starts within 1 week after the surgery. In yet another embodiment, the at least one $CX_3CR1$ or fractalkine inhibitor comprises an agent selected from the group consisting of an antibody, siRNA, ribozyme, antisense, aptamer, peptidomimetic, small molecule, and combinations thereof. In yet another embodiment, the antibody comprises an antibody selected from a polyclonal antibody, monoclonal antibody, humanized antibody, synthetic antibody, heavy chain antibody, human antibody, a biologically active fragment of an antibody, and combinations thereof.

In one embodiment, the small molecule is selected from the group consisting of:
(i) a compound of Formula (I),

wherein in (I):
$A^1$ is $CH_2$ or cyclopentane-1,3-diyl;
n is 0, 1, 2, 3, 4 or 5 if A is $CH_2$, or n is 0, 1, or 2 if A is cyclopentane-1,3-diyl;
$A^2$ and $A^3$ are both H, or $A^2$ and $A^3$ combine to form a divalent radical selected from the group consisting of methanediyl, ethane-1,2-diyl, or propane-1,3-diyl;
$A^4$ is $CH_2$, $CH(CF_3)$, or $CF_2$;
$R^1$ is H, CN, $CO_2R_6$, ($C_1$-$C_6$)$CH_2NH_2$, or ($C_1$-$C_6$) $CH_2NHC(=O)NH(4$-piperidinyl);
$R^2$ and $R^3$ are independently aryl or substituted aryl; or $R^2$ and $R^3$ combine to form a divalent fragment (a), wherein X is selected from the group consisting of —S—, —O—, —CH$_2$S—, —CH$_2$S(=O)—, —CH$_2$S(=O)$_2$—, —SCH$_2$—, —S(=O)CH$_2$—, —S(=O)$_2$CH$_2$—, —CH$_2$CH$_2$—, —CH=CH—, —CH$_2$O—, —OCH$_2$—, —N(CH$_3$)C(=O)—, and —C(=O)N(CH$_3$)—;

(a)

or $R^1$ and $R^2$ are both H, and $R^3$ is selected from the group consisting of:

wherein ring A is selected from the group consisting of phenyl, substituted phenyl, pyridinyl, substituted pyridinyl, thiophenyl, substituted thiophenyl, 1H-pyrazole, and 1-($C_1$-$C_6$) alkyl-1H-pyrazole;

$R^4$ is nil or ($C_1$-$C_6$)alkyl, wherein if $R^4$ is ($C_1$-$C_6$)alkyl, compound of Formula (I) is a quaternary ammonium salt;

$R^5$ is ($C_1$-$C_6$)alkyl, substituted ($C_1$-$C_6$)alkyl, phenyl, substituted phenyl, heteroaryl, substituted heteroaryl;

$R^6$ is H, ($C_1$-$C_6$)alkyl, substituted ($C_1$-$C_6$)alkyl, aryl or substituted aryl; and, $R^7$ is OH, $CH_2OH$, or $C(=O)OR^6$;

(ii) a compound of Formula (II):

(II)

wherein:
A is a ring of formula (a), (b) or (c):

(a)

(b)

(c)

$R^1$ and $R^2$ independently represent H, $C_1$-$C_8$ alkyl, $C_2$-$C_8$ alkenyl, $C_2$-$C_8$ alkynyl or $C_3$-$C_7$ saturated or partially unsaturated cycloalkyl,
wherein in $R^1$ or $R^2$ the alkyl, alkenyl, alkynyl and cycloalkyl groups are optionally and independently further substituted with one or more substituents selected independently from the group consisting of OH, $C_1$-$C_6$ alkoxy, $CH_2OR^4$, $NR^5R^6$, $CO_2R^7$ and $CONR^8R^9$;

$R^3$ is $C_1$-$C_6$ alkyl, $C_2$-$C_6$ alkenyl, $C_2$-$C_6$ alkynyl or $C_3$-$C_7$ saturated or partially unsaturated cycloalkyl;
wherein in $R^3$:
the alkyl, alkenyl and alkynyl chains independently and optionally include a O, $NR^{10}$ or S atom in the chain;
the alkyl, alkenyl, alkynyl and cycloalkyl groups are independently and optionally further substituted by phenyl or a 5- or 6-membered heteroaromatic ring containing 1 to 3 heteroatoms selected independently from the group consisting of O, S and N;
the phenyl or heteroaromatic groups are independently and optionally further substituted with one or more substituents selected from the group consisting of halogen, $C_1$-$C_4$ alkyl, OH, $C_1$-$C_4$ alkoxy, CN, $CO_2R^{11}$, $NR^{12}R^{13}$, $C(=O)NR^{14}R^{15}$, $SO_2R^{16}$, $NR^{17}R^{18}$ and $SO_2N^{19}R^{20}$;

X is O, S or S(O);
$R^{21}$ is H, $CH_2OR^{24}$, $CH_2NR^{24}R^{25}$, $CO_2R^{24}$ or $C(=O)NR^{24}R^{25}$;
n is 0, 1 or 2;
$R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently H or $C_1$-$C_6$ alkyl;

(iii) a compound of Formula (VI):

(VI)

wherein:
$R^1$ is $CH_3$ or $CH_3CH_2$;
$R^2$ is H, 2-F, 2-Cl, 3-F, 3-$OCH_3$, 3-CN, 3-$CF_3$, 3-$CONH_2$ or 3-$SO_2CH_3$;
$R^3$ is H or $CH_3$;
$R^4$ is H or $CH_3$ and
$R^5$ is H; or, when $R^4$ is $CH_3$, $R^5$ is H or F;

(iv) a compound of Formula (VII):

(VII)

wherein:
 R$^1$ is CH$_3$ or CH$_3$CH$_2$;
 R$^2$ is H or CH$_3$;
 R$^3$ is H or CH$_3$;
 R$^4$, R$^5$, R$^6$ and R$^7$ are independently H, CH$_3$ or CH$_2$CH$_3$;
(v) a compound of Formula (VIII):

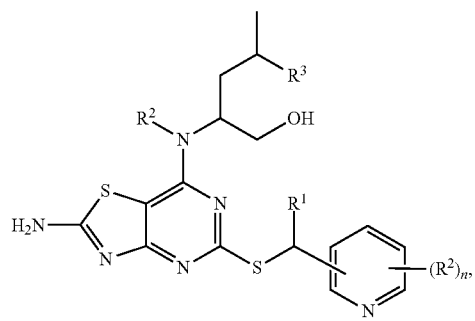
(VIII)

wherein:
 R$^1$ is CH$_3$ or CF$_3$;
 R$^2$ is halo, CN or C$_1$-C$_6$ alkyl;
 R$^3$ and R$^4$ are independently H or CH$_3$;
 n is 0, 1 or 2;
(vi) a compound of Formula (IX):

R$^A$—R$^B$ (IX), wherein:
 R$^A$ is a group selected from the group consisting of:

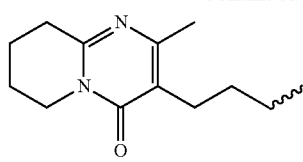

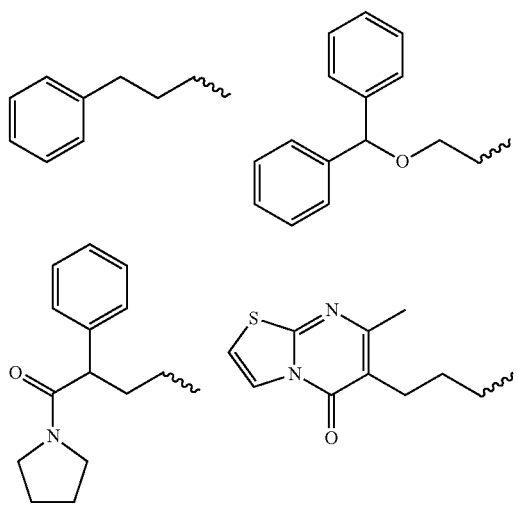

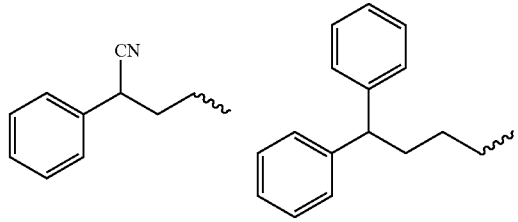

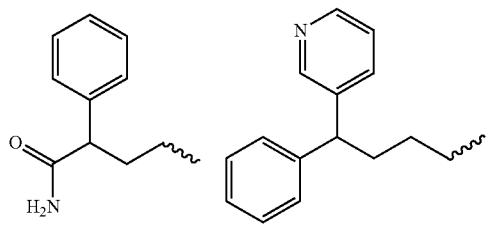

R$^B$ is a group selected from the group consisting of:

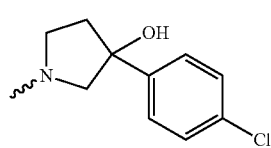

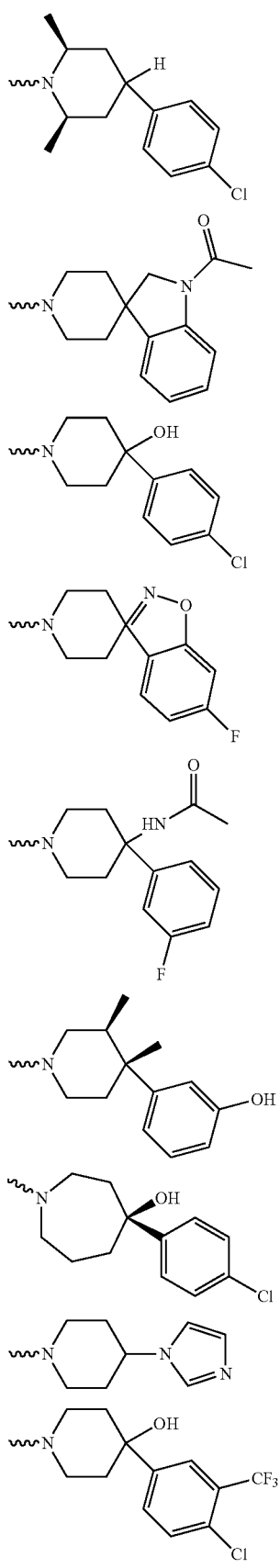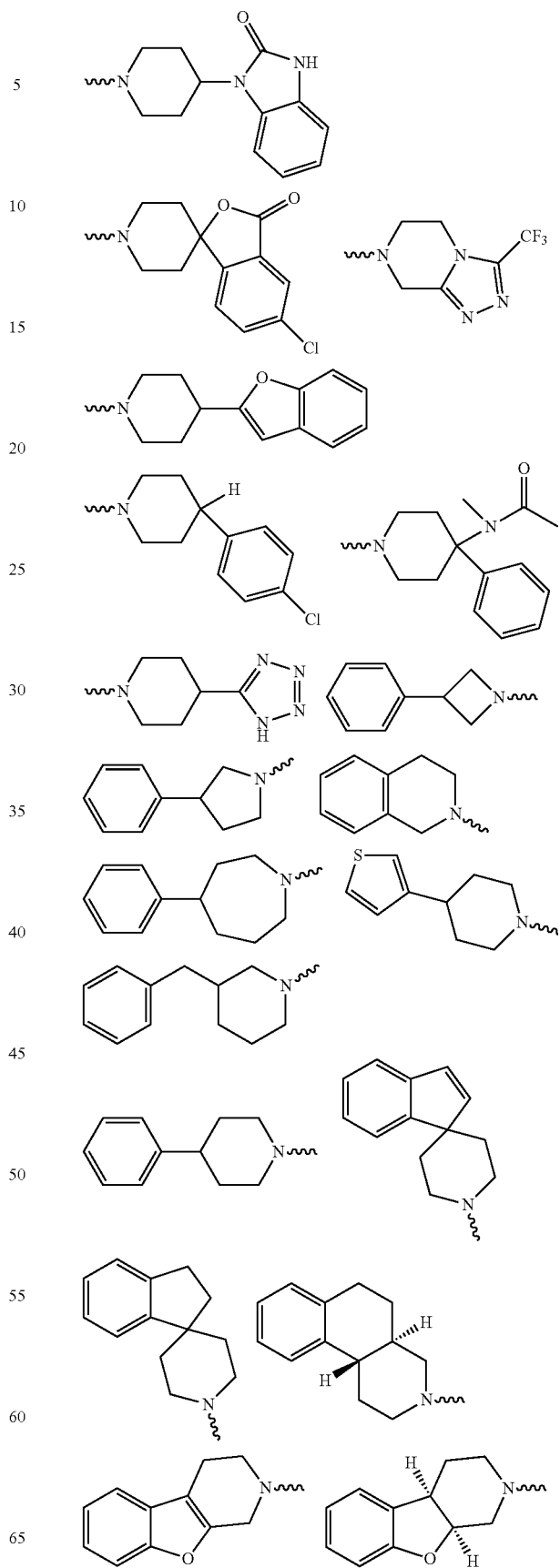

-continued

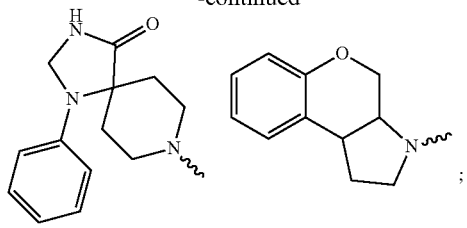

(vii) a compound of Formula (X):

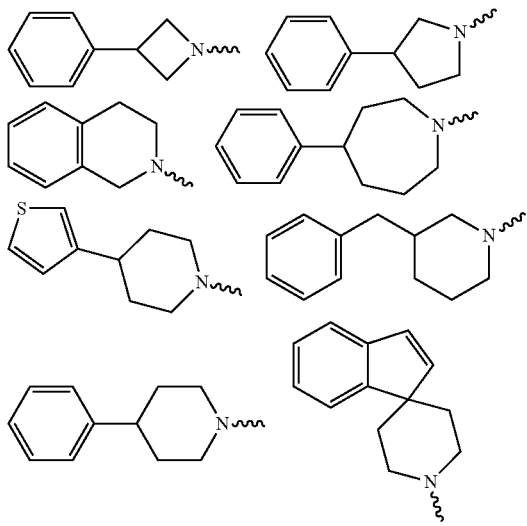

(X)

wherein R¹ is $(C_1-C_8)$ alkyl, substituted $(C_1-C_8)$ alkyl, phenyl, substituted phenyl, $(C_1-C_8)$ cycloalkyl or substituted $(C_1-C_8)$ cycloalkyl;

(viii) a compound of Formula (XI):

$$\text{(XI)}$$

wherein
R is selected from the group consisting of:

-continued

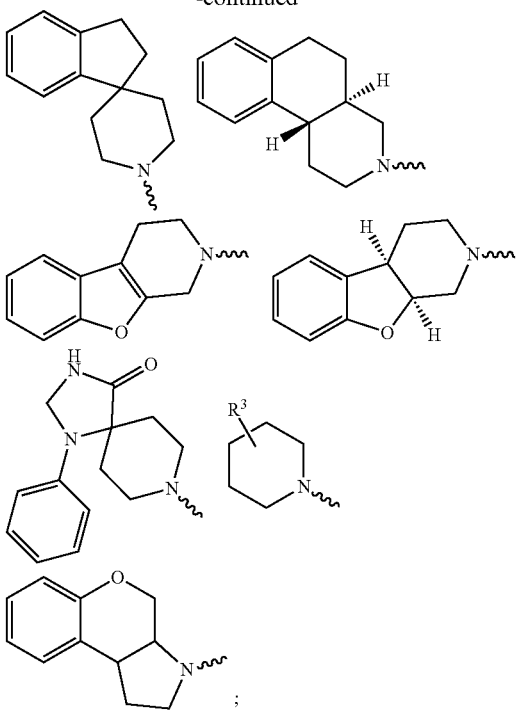

each occurrence of R¹ and R⁴ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, R² and R³ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

(ix) a compound of Formula (XII):

$$\text{(XII)}$$

wherein
R is selected from the group consisting of:

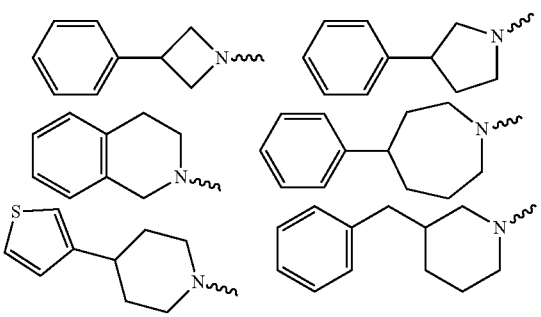

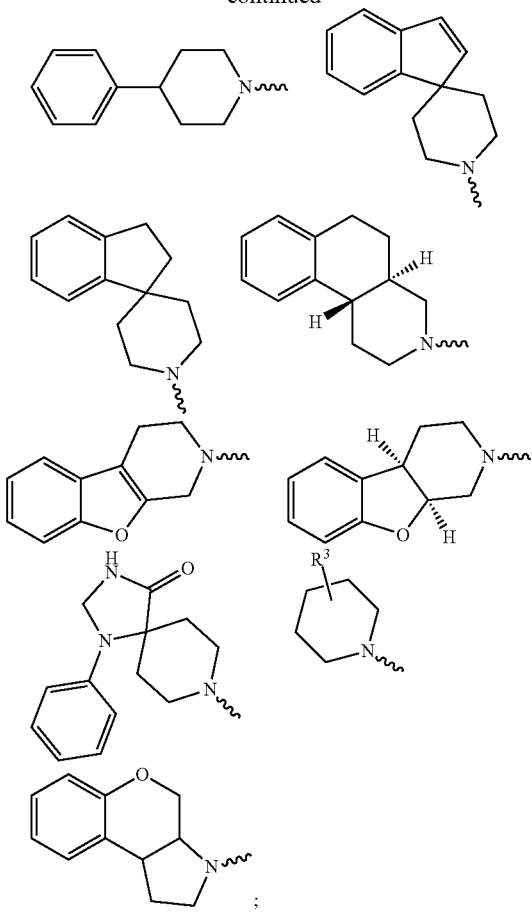

each occurrence of $R^1$ and R4 and $R^5$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

(x) a compound selected from the group:

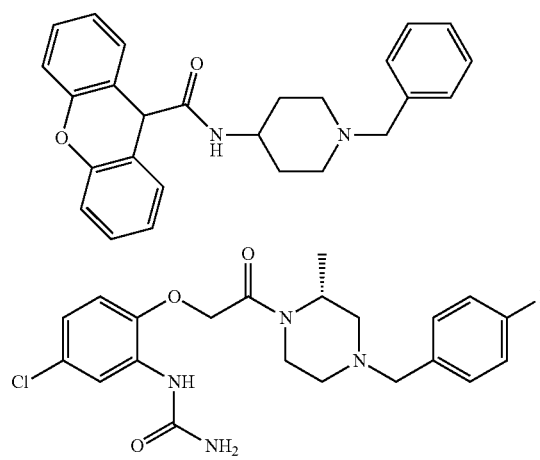

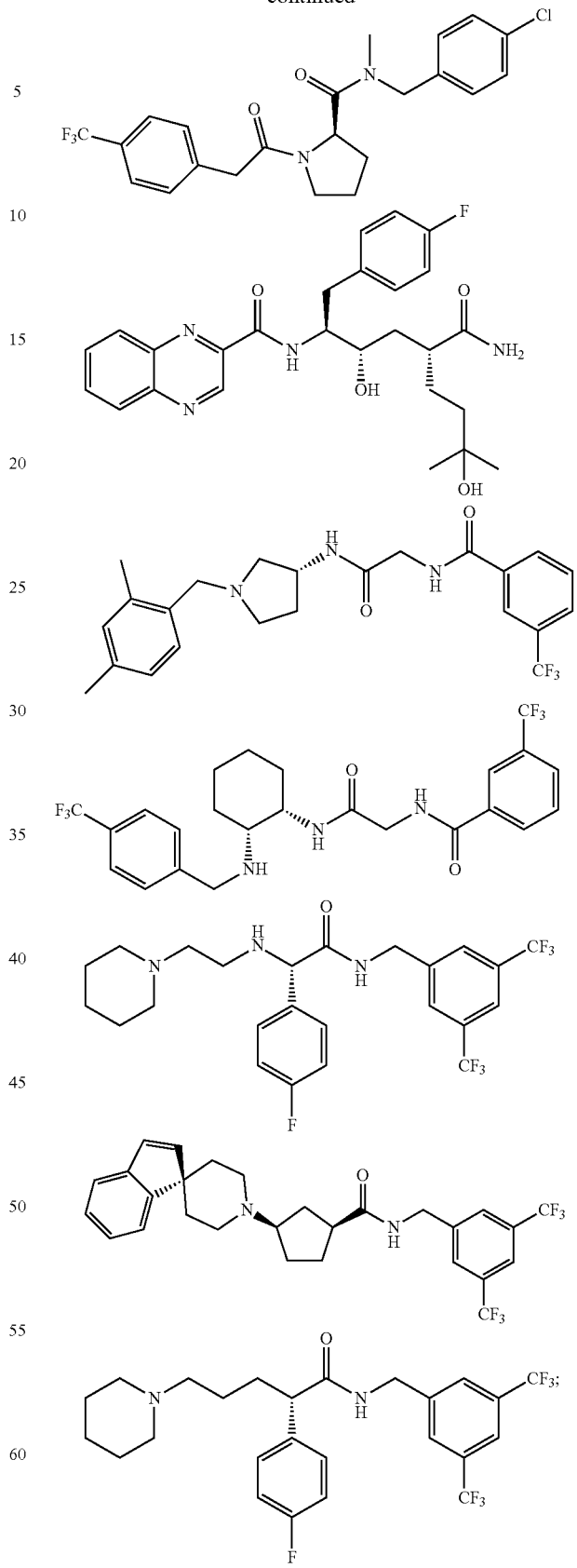

or a pharmaceutically acceptable salt thereof.

In one embodiment, the compound of Formula (I) is a compound of Formula (Ia):

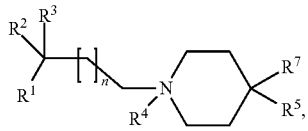
(Ia)

wherein in (Ia):
n is 0, 1, 2, 3, 4 or 5;
$R^1$ is H, CN, $CO_2R_6$, $(C_1-C_6)CH_2NH_2$, or $(C_1-C_6)CH_2NHC(=O)NH(4$-piperidinyl);
$R^2$ and $R^3$ are independently aryl or substituted aryl; or $R^2$ and $R^3$ combine to form a divalent fragment (a), wherein X is selected from the group consisting of S, O, $CH_2S$, $CH_2S(=O)$, $CH_2S(=O)_2$, $SCH_2$, $S(=O)CH_2$, $S(=O)_2CH_2$, $CH_2CH_2$, CH=CH, $CH_2O$, $OCH_2$, $N(CH_3)C(=O)$, and $C(=O)N(CH_3)$;

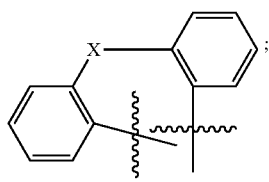
(a)

$R^4$ is no atom or $(C_1-C_6)$alkyl, wherein if $R^4$ is $(C_1-C_6)$alkyl, compound (I) is a quaternary ammonium salt;
$R^5$ is $(C_1-C_6)$alkyl, substituted $(C_1-C_6)$alkyl, phenyl, substituted phenyl, heteroaryl, substituted heteroaryl;
$R^6$ is H, $(C_1-C_6)$alkyl, substituted $(C_1-C_6)$alkyl, aryl or substituted aryl; and,
$R^7$ is OH, $CH_2OH$, or $C(=O)OR^6$.

In one embodiment, in Formula (I) $R^2$ and $R^3$ are independently phenyl, substituted phenyl, naphthryl or substituted naphthryl.

In one embodiment, the compound of Formula (II) is:
(i) a compound of Formula (III):

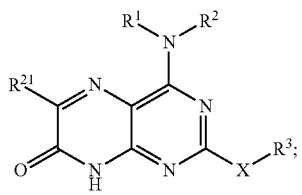
(III)

(b) a compound of Formula (IV):

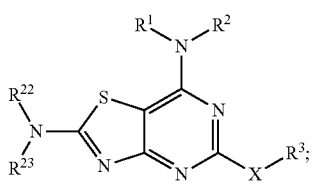
(IV)

(c) a compound of Formula (V):

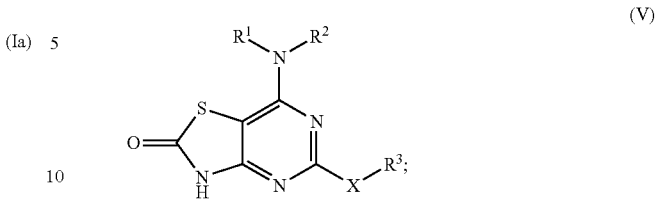
(V)

or a pharmaceutically acceptable salt thereof.

In one embodiment, in Formula (X) $R^1$ is n-hexyl, phenyl or cyclopentyl. In another embodiment, the small molecule is selected from the group consisting of: 5-(4-(4-chlorophenyl)-4-hydroxypiperidin-1-yl)-2,2-diphenylpentanenitrile, N-(1-benzylpiperidin-4-yl)-9H-xanthene-9-carboxamide, 5-(3-(4-(4-chlorophenyl)-4-hydroxypiperidin-1-yl)propyl) pyrrolo[1,2-a]quinoxalin-4(5H)-one, 5-(3-(4-(4-chlorophenyl) piperidin-1-yl)propyl)pyrrolo[1,2-a]quinoxalin-4(5H)-one, combinations thereof, and a pharmaceutically acceptable salt thereof. In another embodiment, the subject is a mammal. In yet another embodiment, the mammal is human. In yet another embodiment, the composition is administered by an administration route selected from the group consisting of inhalational, oral, rectal, vaginal, parenteral, topical, transdermal, pulmonary, intranasal, buccal, ophthalmic, intrathecal, and combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 is a set of pictures illustrating the immunohistochemistry detection of $CX_3CR1$ in human tissue arrays of breast cancer. Hematoxylin and eosin staining is illustrated on the left, and immune-histo-chemistry detection of $CX_3CR1$ in human mammary glands is illustrated on the right. Representative image of 172 malignant cores were analyzed. The BRC1502, BR722 and BR1002 arrays were obtained from US Biomax (Rockville, Md.) and the staining was performed using an antibody against $CX_3CR1$ (7201) obtained from Abcam (Cambridge, Mass.) and used at a 3.3 µg/ml concentration. Original magnification was ×50.

FIG. 18A: Calcium flux stimulated by CX3CL1 in HEK293T cells expressing the human CX3CR1 receptor. FIG. 18B: Calcium flux stimulated by Compound 3 (5-(3-(4-(4-chlorophenyl)-4-hydroxypiperidin-1-yl)propyl)pyrrolo[1,2-a]quinoxalin-4(5H)-one; JMS-16) and Compound 4 (5-(3-(4-(4-chlorophenyl)piperidin-1-yl)propyl)pyrrolo[1,2-a]quinoxalin-4(5H)-one; JMS-17) in HEK293T cells expressing the human CX3CR1 receptor. FIG. 18C: Calcium flux stimulated by EC80 concentration (0.04 µM) of CX3CL1 in cells pretreated with Compound 3 (JMS-16) and Compound 4 (JMS-17).

DETAILED DESCRIPTION OF THE INVENTION

Figure 1:
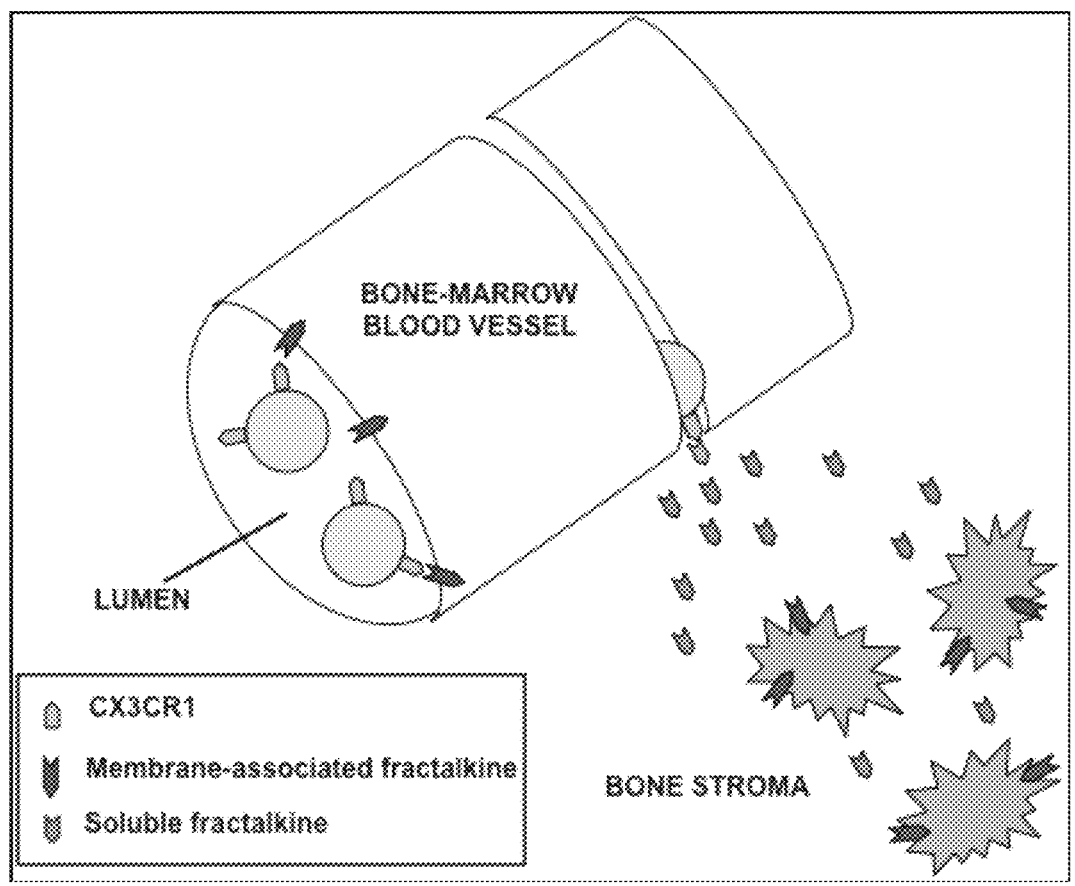
FIG. 1 is a drawing illustrating the proposed model of $CX_3CR1$-FKN interactions regulating the arrest of circulating cancer cells to the skeleton. The membrane-bound form of FKN, expressed on the surface of bone marrow endothelial cells, captures $CX_3CR1$-expressing cancer cells. Subsequently, the soluble form of the chemokine, produced by cells of the bone stroma, will attract adherent cells, thus allowing their extravasation.
Figure 2:
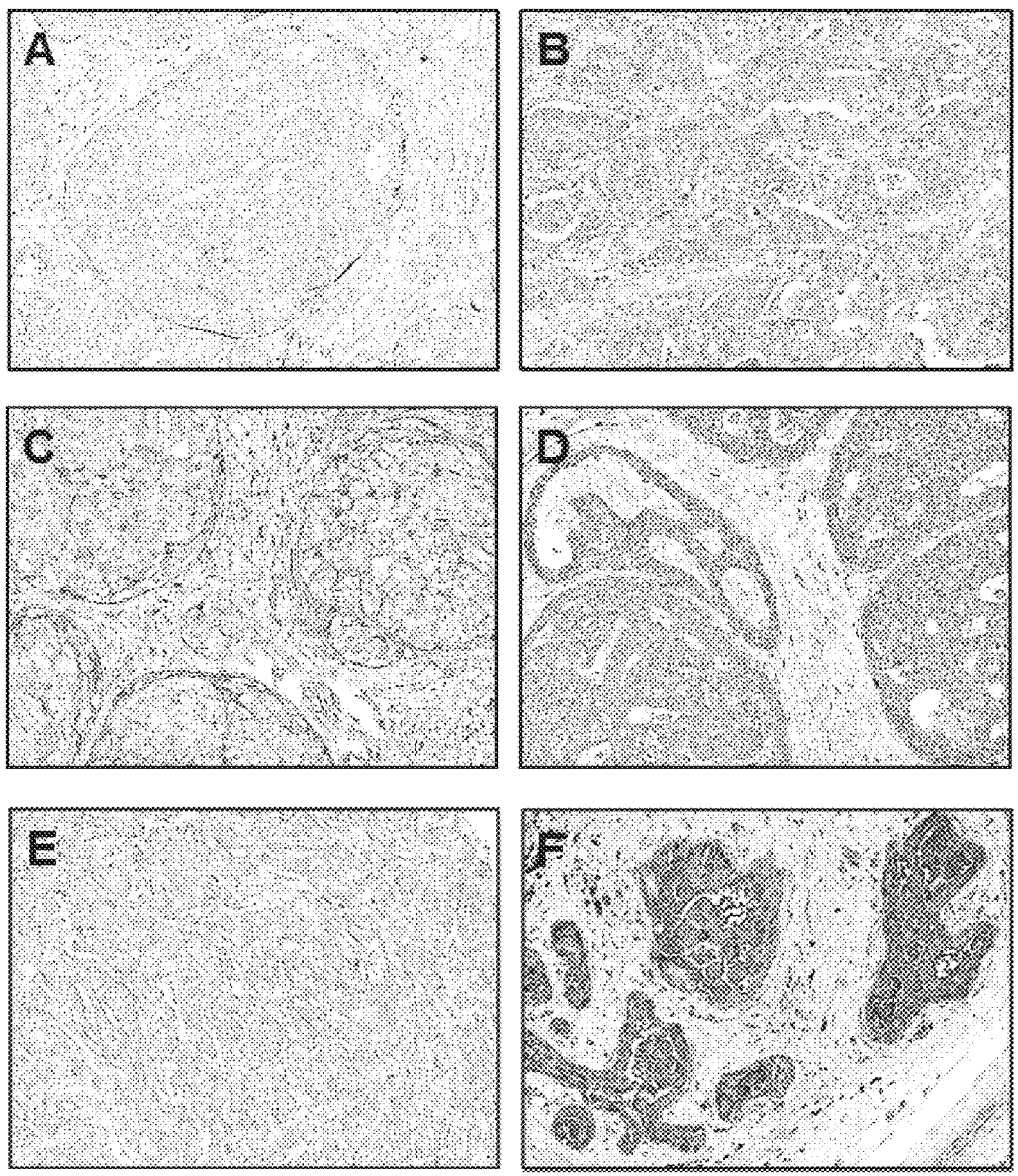
FIG. 2, comprising panels A-F, illustrates the expression of $CX_3CR1$ in human breast cancer tissue arrays. Panel A illustrates a representative sample that stained negative for $CX_3CR1$. The majority of samples examined showed different degrees of positive staining for the receptor in the epithelial cells (Panels B-D; see also Table 1). Panels E-F illustrate a negative and highly positive sample for $CX_3CR1$, respectively, at higher magnification. The stromal compartment stained uniformly negative for $CX_3CR1$. Representative images of 47 normal and 202 malignant tissue cores analyzed. The BRC1502, BR722 and BR1002 arrays were obtained from US Biomax (Rockville, Md.) and the staining was performed using an antibody against $CX_3CR1$ (7201) obtained from Abcam (Cambridge, Mass.) and used at a 3.3 µg/ml concentration. (Original magnification ×100 for Panels A-D, and ×200 for Panels E-F).
Figure 3:
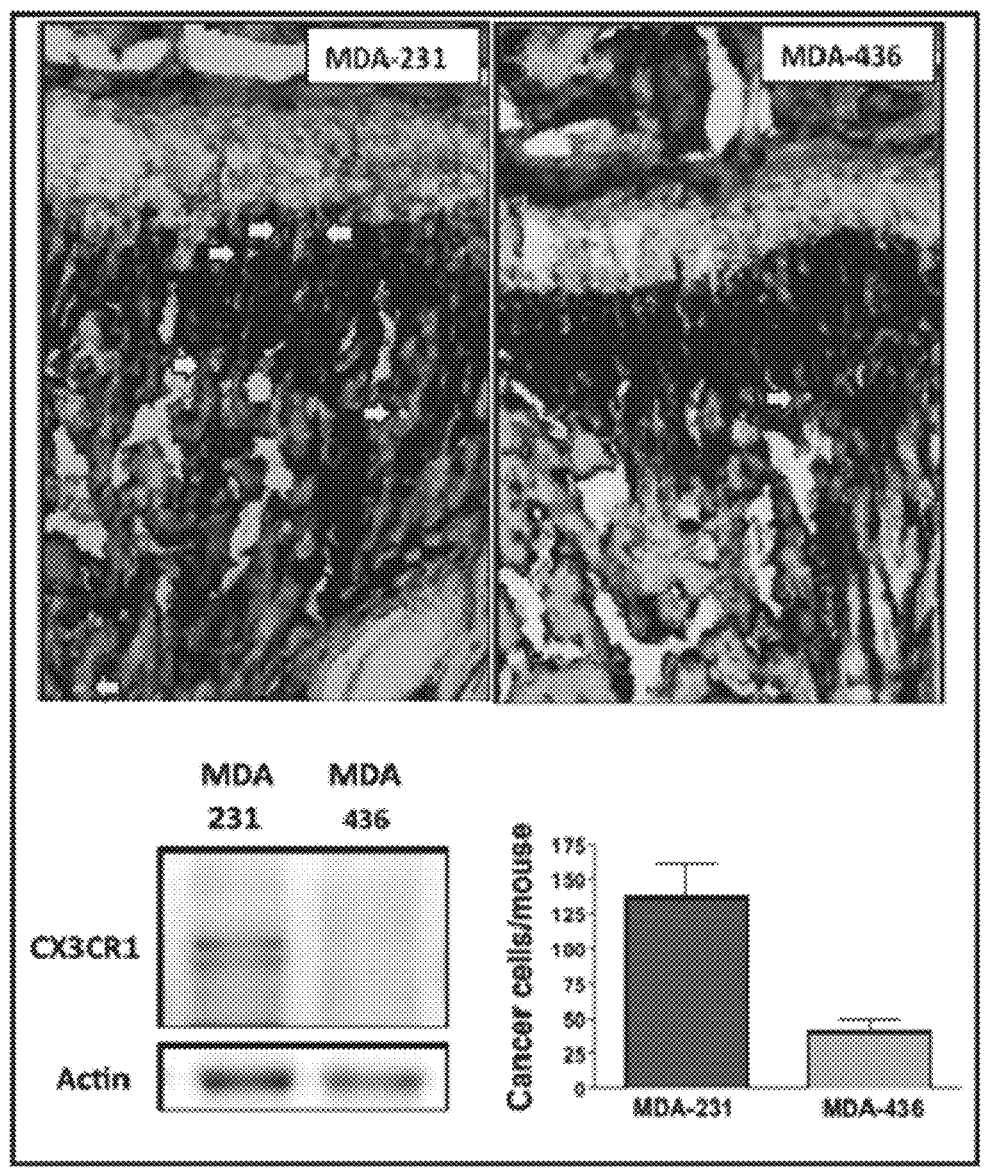
FIG. 3 is a set of figures and a graph illustrating the role of $CX_3CR1$ in the arrival of breast cancer cells to the skeleton. Human cancer cells were directly inoculated into the blood of SCID mice and found to significantly differ in their ability to arrest at the bone marrow. MDA-231 cells were detected in high number when serial cryo-sections of femora or tibiae of inoculated mice were inspected by fluorescence stereomicroscopy. In contrast, similar experiments showed that MDA-436 cells were detected in significantly lower numbers. When tested for $CX_3CR1$ expression, MDA-231 cells were found positive for this chemokine receptor whereas MDA-436 cells failed to express it. Previously both membrane-bound and soluble FKN had been detected in human bone marrow; mouse marrow was also found to contain 6.4 ng/ml of FKN. Thus, these results show a direct correlation between $CX_3CR1$ expression and the arrival of cancer cells to the skeleton and suggest a role for functional interactions between this receptor and its ligand FKN in the process. The two bands observed on the western blot are most likely the result of a previously described $CX_3CR1$ gene polymorphism

The present invention relates to the discovery that metastatic dissemination may take place after primary therapeutic intervention and be caused by cancer cells departing from either residual tumor or recurrences. Therefore, the existing concept that the emergence of metastatic disease is entirely determined by events already occurred when surgery is performed—and that are therefore no longer preventable—does not fully represent the actual clinical scenario. For instance, local surgery on the primary mammary tumor induces the production of a plethora of wound factors that profoundly affect the proliferation of cancer cells and could affect cells that were not eliminated by surgical excision. Prior to re-intervention, residual cancer cells in patients with positive resection margins may benefit from a fertile stromal environment that promotes dissemination. This process would produce secondary waves of micrometastases with at least equal probability of developing into macroscopic tumors as those seeded years earlier. Thus, the adoption of adjuvant measures aimed to interfere with the arrival of cancer cells to the skeleton protects cancer patients from post-surgery tumor dissemination. In one embodiment, the cancer considered within the invention is any kind of cancer or tumor. In another embodiment, the cancer is a solid cancer or tumor. In yet another embodiment, the cancer is breast or prostate cancer or tumor.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "arrest" refers to the recruitment and/or immobilization of circulating cancer cells to an immobilized biological target, such as an organ, for example, a bone.

A "subject", as used therein, can be a human or non-human mammal. Non-human mammals include, for example, livestock and pets, such as ovine, bovine, porcine, canine, feline and murine mammals. Preferably, the subject is human.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "Compound 1" refers to 5-(4-(4-chlorophenyl)-4-hydroxypiperidin-1-yl)-2,2-diphenylpentanenitrile or a salt thereof.

As used herein, the term "Compound 2" refers to N-(1-benzylpiperidin-4-yl)-9H-xanthene-9-carboxamide or a salt thereof.

As used herein, the term "Compound 3" refers to 5-(3-(4-(4-chlorophenyl)-4-hydroxypiperidin-1-yl)propyl)pyrrolo[1,2-a]quinoxalin-4(5H)-one or a salt thereof.

As used herein, the term "Compound 4" refers to 5-(3-(4-(4-chlorophenyl) piperidin-1-yl)propyl)pyrrolo[1,2-a]quinoxalin-4(5H)-one or a salt thereof.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (e.g., for diagnosis or ex vivo applications), who has cancer, a symptom of cancer or the potential to develop cancer, with the purpose to cure, heal, alleviate, relieve, alter, remedy, ameliorate, improve or affect cancer, the symptoms of cancer or the potential to develop cancer. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the terms "effective amount" or "therapeutically effective amount" or "pharmaceutically effective amount" of a compound are used interchangeably to refer to the amount of the compound which is sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation. By the term "specifically bind" or "specifically binds," as used herein, is meant that a first molecule (e.g., an antibody) preferentially binds to a second molecule (e.g., a particular antigenic epitope), but does not necessarily bind only to that second molecule.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, particularly ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, particularly cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—$N(CH_3)$—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein "endogenous" refers to any material from or produced inside an organism, cell, tissue or system. As used herein, the term "exogenous" refers to any material introduced from or produced outside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus. As used herein, a "peptidomimetic" is a compound containing non-peptidic structural elements that is capable of mimicking the biological action of a parent peptide. A peptidomimetic may or may not comprise peptide bonds.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In one aspect, the composition useful in the methods of the invention comprises a compound of Formula (I),

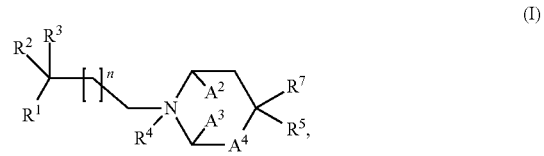

(I)

wherein in (I):

$A^1$ is $CH_2$ or cyclopentane-1,3-diyl;

n is 0, 1, 2, 3, 4 or 5 if A is $CH_2$, or n is 0, 1, or 2 if A is cyclopentane-1,3-diyl;

$A^2$ and $A^3$ are both H, or $A^2$ and $A^3$ combine to form a divalent radical selected from the group consisting of methanediyl, ethane-1,2-diyl, or propane-1,3-diyl;

$A^4$ is $CH_2$, $CH(CF_3)$, or $CF_2$;

$R^1$ is H, CN, $CO_2R_6$, $(C_1-C_6)CH_2NH_2$, or $(C_1-C_6)CH_2NHC(=O)NH(4$-piperidinyl);

$R^2$ and $R^3$ are independently aryl or substituted aryl; or $R^2$ and $R^3$ combine to form a divalent fragment (a), wherein X is selected from the group consisting of —S—, —O—, —$CH_2S$—, —$CH_2S(=O)$—, —$CH_2S(=O)_2$—, —$SCH_2$—, —$S(=O)CH_2$—, —$S(=O)_2CH_2$—, —$CH_2CH_2$—, —CH=CH—, —$CH_2O$—, —$OCH_2$—, —$N(CH_3)C(=O)$—, and —$C(=O)N(CH_3)$—;

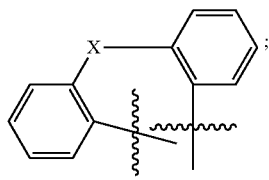

or R¹ and R² are both H, and R³ is selected from the group consisting of:

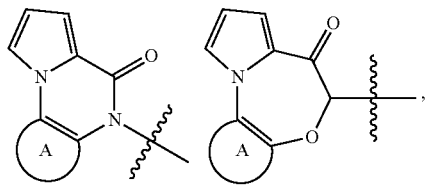

wherein ring A is selected from the group consisting of phenyl, substituted phenyl, pyridinyl, substituted pyridinyl, thiophenyl, substituted thiophenyl, 1H-pyrazole, and 1-($C_1$-$C_6$) alkyl-1H-pyrazole;

R⁴ is nil or ($C_1$-$C_6$)alkyl, wherein if R⁴ is ($C_1$-$C_6$)alkyl, compound of Formula (I) is a quaternary ammonium salt;

R⁵ is ($C_1$-$C_6$)alkyl, substituted ($C_1$-$C_6$)alkyl, phenyl, substituted phenyl, heteroaryl, substituted heteroaryl;

R⁶ is H, ($C_1$-$C_6$)alkyl, substituted ($C_1$-$C_6$)alkyl, aryl or substituted aryl; and, R⁷ is OH, CH₂OH, or C(=O)OR⁶;

or a salt thereof.

In one embodiment, the composition of the invention and/or useful in the methods of the invention comprises a compound of Formula (Ia),

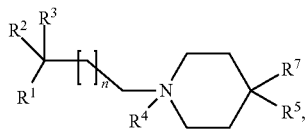
(Ia)

wherein in (Ia):

n is 0, 1, 2, 3, 4 or 5;

R¹ is H, CN, CO₂R⁶, ($C_1$-$C_6$)CH₂NH₂, or ($C_1$-$C_6$) CH₂NHC(=O)NH(4-piperidinyl);

R² and R³ are independently aryl or substituted aryl; or R² and R³ combine to form a divalent fragment (a), wherein X is selected from the group consisting of S, O, CH₂S, CH₂S(=O), CH₂S(=O)₂, SCH₂, S(=O)CH₂, S(=O)₂CH₂, CH₂CH₂, CH=CH, CH₂O, OCH₂, N(CH₃)C(=O), and C(=O)N(CH₃);

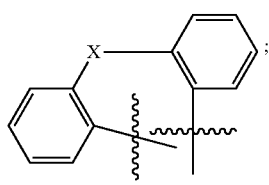
(a)

R⁴ is no atom or ($C_1$-$C_6$)alkyl, wherein if R⁴ is ($C_1$-$C_6$) alkyl, compound (I) is a quaternary ammonium salt;

R⁵ is ($C_1$-$C_6$)alkyl, substituted ($C_1$-$C_6$)alkyl, phenyl, substituted phenyl, heteroaryl, substituted heteroaryl;

R⁶ is H, ($C_1$-$C_6$)alkyl, substituted ($C_1$-$C_6$)alkyl, aryl or substituted aryl; and, R⁷ is OH, CH₂OH, or C(=O)OR⁶;

or a salt thereof.

In one embodiment, R² and R³ are independently phenyl, substituted phenyl, naphthryl or substituted naphthryl. In another embodiment, n is 2.

In one embodiment, R⁵ is phenyl, 2-chlorophenyl, 3-chlorophenyl, 4-chlorophenyl, 2-methoxyphenyl, 3-methoxyphenyl, or 4-methoxyphenyl.

In one embodiment, in Formula (I) R¹ and R² are H, and R³ is selected from the group consisting of:

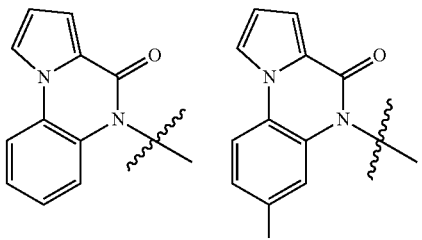

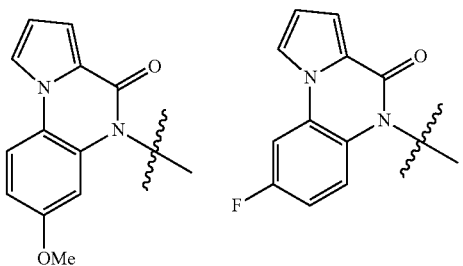

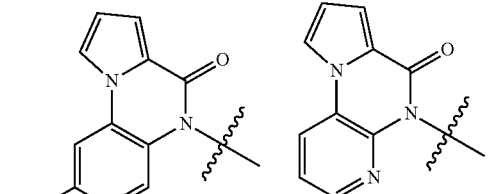

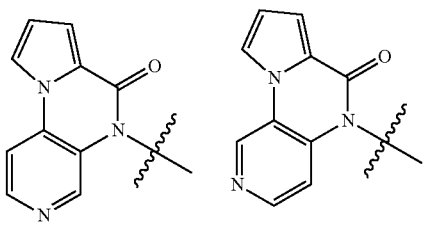

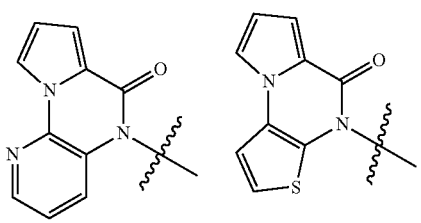

-continued

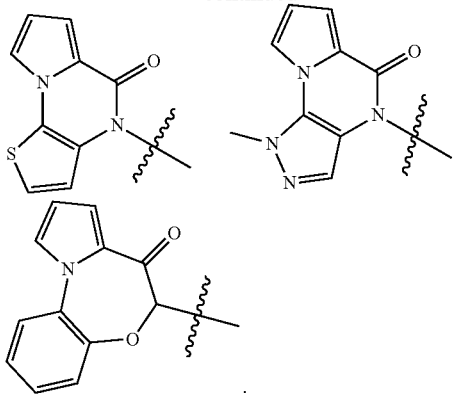

In one embodiment, the compound of formula (I) is selected from the group consisting of: 5-(3-(4-(4-chlorophenyl)-4-hydroxypiperidin-1-yl)propyl)pyrrolo[1,2-a]quinoxalin-4(5H)-one; 5-(3-(4-(4-chlorophenyl)-piperidin-1-yl)propyl)pyrrolo[1,2-a]quinoxalin-4(5H)-one; combinations thereof; or a salt thereof.

In another aspect, the composition useful in the methods of the invention comprises a compound of Formula (II),

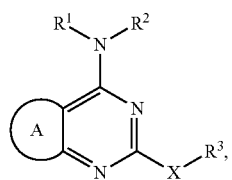
(II)

wherein:
A is a ring of formula (a), (b) or (c):

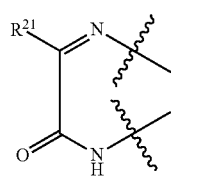
(a)

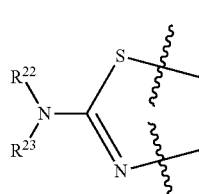
(b)

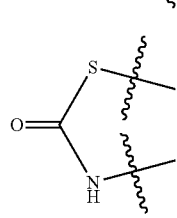
(c)

$R^1$ and $R^2$ independently represent H, $C_1$-$C_8$ alkyl, $C_2$-$C_8$ alkenyl, $C_2$-$C_8$ alkynyl or $C_3$-$C_7$ saturated or partially unsaturated cycloalkyl, wherein in $R^1$ or $R^2$ the alkyl, alkenyl, alkynyl and cycloalkyl groups are optionally and independently further substituted with one or more substituents selected independently from the group consisting of OH, $C_1$-$C_6$ alkoxy, $CH_2OR^4$, $NR^5R^6$, $CO_2R^7$ and $CONR^8R^9$;

$R^3$ is $C_1$-$C_6$ alkyl, $C_2$-$C_6$ alkenyl, $C_2$-$C_6$ alkynyl or $C_3$-$C_7$ saturated or partially unsaturated cycloalkyl;

wherein in $R^3$:
the alkyl, alkenyl and alkynyl chains independently and optionally include a O, $NR^{10}$ or S atom in the chain;
the alkyl, alkenyl, alkynyl and cycloalkyl groups are independently and optionally further substituted by phenyl or a 5- or 6-membered heteroaromatic ring containing 1 to 3 heteroatoms selected independently from the group consisting of O, S and N;
the phenyl or heteroaromatic groups are independently and optionally further substituted with one or more substituents selected from the group consisting of halogen, $C_1$-$C_4$ alkyl, OH, $C_1$-$C_4$ alkoxy, CN, $CO_2R^{11}$, $NR^{12}R^{13}$, $C(=O)NR^{14}R^{15}$, $SO_2R^{16}$, $NR^{17}R^{18}$ and $SO_2N^{19}R^{20}$;

X is O, S or S(O);
$R^{21}$ is H, $CH_2OR^{24}$, $CH^2NR^{24}R^{25}$, $CO_2R^{24}$ or $C(=O)NR^{24}R^{25}$;
n is 0, 1 or 2;
$R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently H or $C_1$-$C_6$ alkyl;
or a salt thereof.

In one embodiment, the compound of Formula (II) is a compound of Formula (III) or a salt thereof:

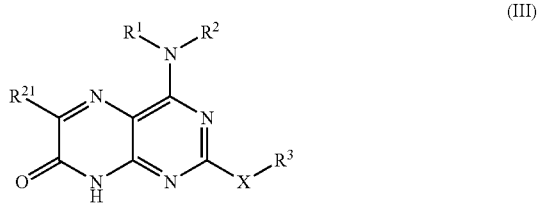
(III)

In one embodiment, the compound of Formula (II) is a compound of Formula (IV) or a salt thereof:

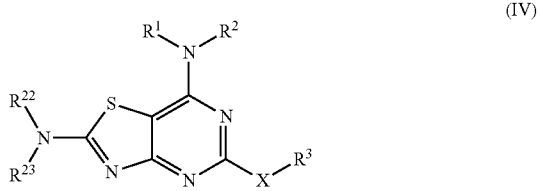
(IV)

In one embodiment, the compound of Formula (II) is a compound of Formula (V) or a salt thereof:

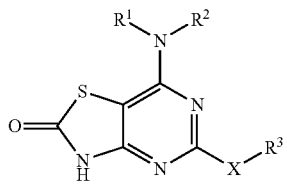

(V)

In one embodiment, the compound of Formula (II) is selected from the group consisting of:

(2R)-2-{[2-amino-5-(benzyloxy)[1,3]thiazolo[4,5-d]pyrimidin-7-yl]amino}-4-methylpentan-1-ol;
(2R)-2-({2-amino-5-[(3-methoxybenzyl)oxy][1,3]thiazolo[4,5-d]pyrimidin-7-yl}amino)-4-methylpentan-1-ol;
(2R)-2-{[2-amino-5-(2-phenylethoxy)[1,3]thiazolo[4,5-d]pyrimidin-7-yl]amino}-4-methylpentan-1-ol;
(2R)-2-{[2-amino-5-(2-phenoxyethoxy)[1,3]thiazolo[4,5-d]pyrimidin-7-yl]amino}-4-methylpentan-1-ol;
(2R)-2-[{2-amino-5-[(2-methylbenzyl)oxy][1,3]thiazolo[4,5-d]pyrimidin-7-yl} (methyl)amino]-4-methylpentan-1-ol;
(2R)-2-[{2-amino-5-[(4-chlorobenzyl)oxy][1,3]thiazolo[4,5-d]pyrimidin-7-yl}(methyl)amino]-4-methylpentan-1-ol;
(2R)-2-[{(2-amino-5-[(3-chlorobenzyl)oxy][1,3]thiazolo 4,5-d]pyrimidin-7-yl}(methyl)amino]-4-methylpentan-1-ol;
(2R)-2-[{2-amino-5-[(2-methoxybenzyl)oxy][1,3]thiazolo[4,5-d]pyrimidin-7-yl}(methyl)amino]-4-methylpentan-1-ol;
(2R)-2-[[2-amino-5-(benzyloxy)[1,3]thiazolo[4,5-d]pyrimidin-7-yl](methyl)amino]-4-methylpentan-1-ol;
(2R)-[{2-amino-5-[(4-bromo-2-fluorobenzyl)-($R_S,S_S$)-sulfinyl][1,3]thiazolo[4,5-d]pyrimidin-7-yl}(methyl)amino]-4-methylpentan-1-ol;
(2R)-2-[(2-amino-5-{[2-(4-bromophenyl)ethyl]($R_S,S_S$)-sulfinyl}[1,3]thiazolo[4,5-d]pyrimidin-7-yl)amino]4-methylpentan-1-ol;
(2R)-2-[(2-amino-5-{[2-(2-bromophenyl)ethyl]($R_S,S_S$)-sulfinyl}[1,3]thiazol[4,5-d]pyrimidin-7-yl)amino]4-methylpentan-1-ol;
(R)-2-[(2-amino-5-{[2-(2-bromophenyl)ethyl]($R_S,S_S$)-sulfinyl}[1,3]thiazolo[4,5-d]pyrimidin-7 yl)(methyl)amino]-4-methylpentan-1-ol;
2-[(2,3-difluorobenzyl)oxy]-4-{[(1R)-1-(hydroxymethyl)-3-methylbutyl]amino}pteridin-7(8H)-one;
4-[(1R)-1-(hydroxymethyl)-3-methylbutyl]amino}-2-[(3-methoxybenzyl)oxy]pteridin-7(8H)-one;
2-[(2-chloro-3-methoxybenzyl)oxy]-4-[(1R)-1-(hydroxymethyl)-3-methylbutyl]amino}pteridin-7(8H)one;
4-([(1R)-1-(hydroxymethyl)-3-methylbutyl]amino}-2-(2-phenylethoxy)pteridin-7(8H)-one;
4-{[(1R)-1-(hydroxymethyl)-3-methylbutyl]amino}-2-(2-phenoxyethoxy)pteridin-7(8H)-one;
2-[(2-chlorobenzyl)oxy]-4-{[(1R)-1-(hydroxymethyl)-3-methylbutyl]amino}pteridin-7(8H)-one;
2-[(4-chlorobenzyl)oxy]-4-{[(1R)-1-(hydroxymethyl)-3-methylbutyl]amino}pteridin-7(8H)-one;
4-{[(1R)-1-(hydroxymethyl)-3-methylbutyl]amino}-2-[(4-methylbenzyl)oxy]pteridin-7(8H)-one;
4-{[(1R)-1-(hydroxymethyl)-3-methylbutyl]amino}-2-[(3-methylbenzyl)oxy]pteridin-7(8H)-one;
2-[(3-chlorobenzyl)oxy]-4-{[(1S,2S)-2-hydroxyl-(hydroxymethyl)propyl]amino}-7-oxo-7,8-dihydropteridine-6-carboxamide;

2-[(2,3-difluorobenzyl)-($R_S,S_S$)-sulfinyl]-4-{[(1R)-1-(hydroxymethyl)-3-methylbutyl]amino}pteridin-7(8H)-one;
5-(benzyloxy)-7-{[(1R)-1-(hydroxymethyl)-3-methylbutyl]amino}[1,3]thiazolo[4,5-d]pyrimidin-2(3H)one;
7-{[(1R)-1-(hydroxymethyl)-3-methylbutyl]amino}-5-[(3-methoxybenzyl)oxy][1,3]thiazolo[4,5-d]pyrimidin-2(3H)-one;
7-{[(1R)-1-(hydroxymethyl)-3-methylbutyl]amino}-5-(2-phenylethoxy)[1,3]thiazolo[4,5-d]pyrimidin-2(3H)-one;
5-(benzyloxy)-7-{[(1R)-1-(hydroxymethyl)butyl]amino}[1,3]thiazolo[4,5-d]pyrimidin-2(3H)-one;
7-{[(1R)-1-(hydroxymethyl)butyl]amino}-5-{[(1S)-1-phenylethyl]oxy}[1,3]thiazolo[4,5-d]pyrimidin-2(3H)-one;
N-(3-{[(7-{[(1R)-1-(hydroxymethyl)butyl]amino}-2-oxo-2,3-dihydro[1,3]thiazolo[4.5-d]pyrimidin-5-yl)oxy]methyl}phenyl)-N-methylmethanesulfonamide;
N-(3-{[(7-{[(1R)-1-(hydroxymethyl)-2-methylpropyl]amino}-2-oxo-2,3-dihydro[1,3]thiazolo[4,5-d]pyrimidin-5-yl)oxy]methyl} phenyl)methanesulfonamide;
5-(benzyloxy)-7-{[1-(hydroxymethyl)cyclopentyl]amino}[1,3]thiazolo[4,5-d]pyrimidin-2(3H)-one;
7-{[1-(hydroxymethyl)cyclopentyl]amino}-5-[(2-methylbenzyl)oxy][1,3]thiazolo[4,5-d]pyrimidin-2(3H)one;
7-{[1-(hydroxymethyl)cyclopentyl])amino}-5-[(3-methylbenzyl)oxy][1,3]thiazolo[4,5-d]pyrimidin-2(3H)-one;
5-[(2-chlorobenzyl)oxy]-7-{[1-(hydroxymethyl)cyclopentyl)amino}[1,3]thiazolo[4,5-d]pyrimidin-2(3H)-one;
5-[(3-chlorobenzyl)oxy]-7-{[1-(hydroxymethyl)cyclopentyl]amino}[1,3]thiazolo[4,5-d]pyrimidin-2(3H)-one;
5-[(4-chlorobenzyl)oxy]-7-{[1-(hydroxymethyl)cyclopentyl]amino}[1,3]thiazolo[4,5-d]pyrimidin-2(3H)-one;
7-{[1-(hydroxymethyl)cyclopentyl]amino}-5-[(2-methoxybenzyl)oxy][1,3]thiazolo[4,5-d]pyrimidin-2(3H)-one;
7-{[1-(hydroxymethyl)cyclopentyl]amino}-5-[(3-methoxybenzyl)oxy][1,3]thiazolo[4,5-d]pyrimidin-2(3H)-one;
4-{[(7-{[1-(hydroxymethyl)cyclopentyl]amino}-2-oxo-2,3-dihydro[1,3]thiazolo[4,5-d]pyrimidin-5-yl)oxy]methyl}benzonitrile;
(R,S)-7-[[1-(hydroxymethyl)cyclopentyl]amino]-5-(1-phenylethoxy)-thiazolo[4.5-d]pyrimidin-2(3H)-one;
7-{[1-(hydroxymethyl)cyclopentyl]amino}-5-{[(1S)-1-phenylethyl]oxy} [1,3]thiazolo[4.5-d]pyrimidin-2(3H)-one;
5-{[2-(3-chlorophenyl)ethyl]-($R_S,S_S$)-sulfinyl}-7-{[(1R)-1-(hydroxymethyl)-3-methylbutyl]amino}[1,3]thiazolo[4,5-d]pyrimidin-2(3H)-one;
5-{[2-(2-bromophenyl)ethyl]-($R_S,S_S$)-sulfinyl}-7-{[(1R)-1-(hydroxymethyl)-3-methylbutyl]amino}[1,3]thiazolo[4,5-d]pyrimidin-2(3H)-one;
5-[(2,3-difluorobenzyl)-($R_S,S_S$)-sulfinyl]-7-{[(1R)-1-(hydroxymethyl)-3-methylbutyl]amino}[1,3]thiazolo[4,5-d]pyrimidin-2(3H)-one;
5-[benzyl-($R_S,S_S$)-sulfinyl]-7-{[(1R)-1-(hydroxymethyl)-3-methylbutyl]amino}[1,3]thiazolo[4,5-d]pyrimidin-2(3H)-one;
5-[(2-chlorobenzyl)-($R_S,S_S$)-sulfinyl]-7-{[(1R)-1-(hydroxymethyl)-3-methylbutyl]amino}[1,3]thiazolo[4,5-d]pyrimidin-2(3H)-one;
5-[(4-chlorobenzyl)-($R_S,S_S$)-sulfinyl]-7-{[(1R)-1-(hydroxymethyl)-3-methylbutyl]amino}[1,3]thiazolo[4,5-d]pyrimidin-2(3H)-one;
5-[benzyl-($R_S,S_S$)-sulfinyl]-7-{[(1R)-1-(hydroxymethyl)-2-methylpropyl]amino}[1,3]thiazolo[4,5-d]pyrimidin-2(3H)-one;
11-[3-[4-(4-Fluorophenyl)-4-hydroxy-1-piperidinyl]propyl]-6,11-dihydrodibenzo[b,e]thiepin-11-carbonitrile;
6,11-Dihydro-11-[3-(4-hydroxy-4-phenyl-1-piperidinyl)propyl]dibenzo[b,e]thiepin-11-carbonitrile;

11-[3-[4-Hydroxy-4-(2-methylphenyl)-1-piperidinyl]propyl]-6,11-dihydrodibenzo[b,e]thiepin-11-carbonitrile;
11-[3-[4-Hydroxy-4-(3-trifluoromethylphenyl)-1-piperidinyl]propyl]-6,11-dihydrodibenzo[b,e]thiepin-11-carbonitrile;
11-[3-[4-Hydroxy-4-(3-trifluoromethyl-4-chlorophenyl)-1-piperidinyl]propyl]-6,11-dihydrodibenzo[b,e]thiepin-11-carbonitrile;
11-[3-[4-(4-Bromophenyl)-4-hydroxy-1-piperidinyl]propyl]-6,11-dihydrodibenzo[b,e]thiepin-11-carbonitrile;
11-[3-[4-(4-Chlorophenyl)-4-hydroxy-1-piperidinyl]propyl]-6,11-dihydrodibenzo[b,e]thiepin-11-carbonitrile;
6,11-Dihydro-11-[3-(4-phenyl-1-piperidinyl)propyl]-dibenzo[b,e]thiepin-11-carbonitrile;
1-[3-(11-Cyano-6,11-dihydrodibenzo[b,e]thiepin-11-yl)propyl]-4-phenyl-4-piperidinecarbonitrile;
11-[3-(4-Acetyl-4-phenyl-1-piperidinyl)propyl]-6,11-dihydrodibenzo[b,e]thiepin-11-carbonitrile;
6,11-Dihydro-11-[3-[4-hydroxy-4-(phenylmethyl)-1-piperidinyl]propyl]dibenzo[b,e]thiepin-11-carbonitrile;
6,11-Dihydro-11-[3-[4-(hydroxydiphenylmethyl)-1-piperidinyl]propyl]dibenzo[b,e]thiepin-11-carbonitrile;
9-[3-[4-(4-Chlorophenyl)-4-hydroxy-1-piperidinyl]propyl]-9H-xanthene-9-carbonitrile;
5-[3-[4-(4-Chlorophenyl)-4-hydroxy-1-piperidinyl]propyl]-10,11-dihydro-5H-dibenzo[a,d]cycloheptene-5-carbonitrile;
5-[3-[4-(4-Chlorophenyl)-4-hydroxy-1-piperidinyl]propyl]-5H-dibenzo[a,d]cycloheptene-5-carbonitrile;
11-[3-[4-(4-Chlorophenyl)-4-hydroxy-1-piperidinyl]propyl]-6,11-dihydrodibenzo[b,e]oxepin-11-carbonitrile;
11-[3-[4-(4-Chlorophenyl)-4-hydroxy-1-piperidinyl]propyl]-6,11-dihydrodibenzo[b,e]thiepin-11-carbonitrile, 5-Oxide;
11-[3-[4-(4-Chlorophenyl)-4-hydroxy-1-piperidinyl]propyl]-6,11-dihydro-5-methyl-6-oxo-5H-dibenzo[b,e]azepine-11-carbonitrile;
4-(4-Chlorophenyl)-4-hydroxy-α,α-diphenyl-1-piperidinepentanenitrile;
4-(4-Fluorophenyl)-4-hydroxy-α,α-diphenyl-1-piperidinepentanenitrile;
4-(4-Bromophenyl)-4-hydroxy-α,α-diphenyl-1-piperidinepentanenitrile;
4-Hydroxy-α,α,4-triphenyl-1-piperidinepentanenitrile;
1-(4-Cyano-4,4-diphenylbutyl)-4-phenyl-4-piperidinecarboxylic acid, methyl ester;
1-(4-Cyano-4,4-diphenylbutyl)-4-phenyl-4-piperidinecarboxylic acid;
4-(Hydroxymethyl)-α,α-4-triphenyl-1-piperidinepentanenitrile;
4-Hydroxy-α,α-diphenyl-1-piperidinepentanenitrile;
4-Hydroxy-α,α-diphenyl-4-(2-thienyl)-1-piperidinepentanenitrile;
4-Hydroxy-α,α-diphenyl-4-(2-pyridinyl)-1-piperidinepentanenitrile;
4-Hydroxy-4-(2-naphthalenyl-α,α-diphenyl-1-piperidinepentanenitrile;
4-Hydroxy-r,r-diphenyl-4-(3-pyridinyl)-1-piperidinepentanenitrile;
4-[1,1'-Biphenyl]-4-yl-4-hydroxy-α,α-diphenyl-1-piperidinepentanenitrile;
4-Butyl-4-hydroxy-α,α-diphenyl-1-piperidinepentanenitrile;
4-Hydroxy-4-(4-iodophenyl)-α,α-diphenyl-1-piperidinepentanenitrile;
4-(3-Chlorophenyl)-4-hydroxy-α,α-diphenyl-1-piperidinepentanenitrile;
4-(3,5-Dichlorophenyl)-4-hydroxy-r,r-diphenyl-1-piperidinepentanenitrile;
4-Hydroxy-4-(4-methoxyphenyl-α,α-diphenyl-1-piperidinepentanenitrile;
4-Hydroxy-α,α-diphenyl-4-[4-(trifluoromethyl)phenyl]-1-piperidinepentanenitrile;
4-(4-Aminophenyl)-4-hydroxy-α,α-diphenyl-1-piperidinepentanenitrile;
4-[4-(Dimethylamino)phenyl]-4-hydroxy-α,α-diphenyl-1-piperidinepentanenitrile;
3-(4-Fluorophenyl)-α-(1,5-cyclohexadien-1-yl)-3-hydroxy-α-phenyl-1-piperidinehexanenitrile;
3-(4-Fluorophenyl)-α-(1,5-cyclohexadien-1-yl)-3-hydroxy-α-phenyl-1-pyrrolidinehexanenitrile;
4-(4-Chlorophenyl)-4-hydroxy-α,α-diphenyl-1-piperidinepentanenitrile, N-oxide;
4-(4-Chlorophenyl)-4-hydroxy-1-[5-cyano-5-(1,5-cyclohexadien-1-yl)-5-phenylpentyl]-1-methyl-piperidinium;
4-(4-Chlorophenyl)-4-hydroxy-1-[5-(1,5-cyclohexadien-1-yl)-5-phenylpentyl]-1-methyl-piperidinium;
4-(4-Chlorophenyl)-4-hydroxy-1-[5-cyano-5-(2-naphthalenyl)pentyl]-1-methyl-piperidinium;
4-(4-Chlorophenyl)-4-hydroxy-α-(2-naphthalenyl)-1-piperidinepentanenitrile;
4-(4-Chlorophenyl)-4-hydroxy-α,α-diphenyl-1-piperidinebutanenitrile;
4-(4-Chlorophenyl)-4-hydroxy-α,α-diphenyl-1-piperidinehexanenitrile;
4-(4-Chlorophenyl)-4-hydroxy-α,α-diphenyl-1-piperidineheptanenitrile;
4-(4-Chlorophenyl)-4-hydroxy-α-phenyl-1-piperidinepentanenitrile;
α-(3-Bromo-4-methoxyphenyl)-4-(4-chlorophenyl)-4-hydroxy-1-piperidinepentanenitrile;
4-(4-Chlorophenyl)-α-(2-cyanophenyl)-4-hydroxy-1-piperidinepentanenitrile;
4-(4-Chlorophenyl)-4-hydroxy-α-(2,3,4,5,6-pentafluorophenyl)-1-piperidinepentanenitrile;
4-(4-Chlorophenyl)-4-hydroxy-α-(3-hydroxyphenyl)-1-piperidinepentanenitrile;
4-(4-Chlorophenyl)-α-(2-fluorophenyl)-4-hydroxy-1-piperidinepentanenitrile;
4-(4-Chlorophenyl)-α-(4-fluorophenyl)-4-hydroxy-1-piperidinepentanenitrile;
α-(2-Bromophenyl)-4-(4-chlorophenyl)-4-hydroxy-1-piperidinepentanenitrile,
α,4-Bis(4-chlorophenyl)-4-hydroxy-1-piperidinepentanenitrile;
α-(2-Chlorophenyl)-4-(4-chlorophenyl)-4-hydroxy-1-piperidinepentanenitrile;
4-(4-Chlorophenyl)-4-hydroxy-α-[2-(trifluoromethyl)-phenyl]-1-piperidinepentanenitrile;
4-(4-Chlorophenyl)-4-hydroxy-α-[2-(phenylmethoxy)-phenyl]-1-piperidinepentanenitrile;
4-(4-Chlorophenyl)-4-hydroxy-α-[3-(phenylmethoxy)-phenyl]-1-piperidinepentanenitrile;
4-(4-Chlorophenyl)-4-hydroxy-α-[4-(phenylmethoxy)-phenyl]-1-piperidinepentanenitrile;
4-(4-Chlorophenyl)-4-hydroxy-α-(3-phenoxyphenyl)-1-piperidinepentanenitrile;
4-(4-Chlorophenyl)-4-hydroxy-α-(2-hydroxyphenyl)-1-piperidinepentanenitrile;
4-(4-Chlorophenyl)-4-hydroxy-α-(4-hydroxyphenyl)-1-piperidinepentanenitrile;
4-(4-Chlorophenyl)-4-hydroxy-α-(3,4,5-trimethoxyphenyl)-1-piperidinepentanenitrile;

4-(4-Chlorophenyl)-4-hydroxy-α-(3-nitrophenyl)-1-piperidinepentanenitrile;
4-(4-Chlorophenyl)-4-hydroxy-α-(4-methoxyphenyl)-1-piperidinepentanenitrile;
4-(4-Chlorophenyl)-4-hydroxy-α-(4-ethoxyphenyl)-1-piperidinepentanenitrile;
4-(4-Chlorophenyl)-4-hydroxy-α-(2-thienyl)-1-piperidinepentanenitrile;
4-(4-Chlorophenyl)-4-hydroxy-α-(3-thienyl)-1-piperidinepentanenitrile;
4-(4-Chlorophenyl)-4-hydroxy-α-(1-naphthalenyl)-1-piperidinepentanenitrile;
4-(4-Chlorophenyl)-4-hydroxy-α-(2-pyridinyl)-1-piperidinepentanenitrile;
4-(4-Chlorophenyl)-4-hydroxy-α-(3-pyridinyl)-1-piperidinepentanenitrile;
4-(4-Chlorophenyl)-4-hydroxy-α-(1-methyl-1H-pyrrol-2-yl)-1-piperidinepentanenitrile;
4-(4-Chlorophenyl)-α-cyano-4-hydroxy-α-phenyl-1-piperidinepentanoic acid, ethyl ester;
4-(4-Chlorophenyl)-α-cyano-4-hydroxy-α-phenyl-1-piperidinepentanoic acid, Methyl Ester;
4-(4-Chlorophenyl)-α-(3-chloropropyl)-4-hydroxy-α-phenyl-1-piperidinepentanenitrile;
4-(4-Chlorophenyl)-4-hydroxy-α-methyl-α-phenyl-1-piperidinepentanenitrile;
4-(4-Chlorophenyl)-α-ethyl-4-hydroxy-α-phenyl-1-piperidinepentanenitrile;
2-[3-[4-(4-Chlorophenyl)-4-hydroxy-1-piperidinyl]propyl]-2-phenylbutanedinitrile;
4-(4-Chlorophenyl)-α-cyclohexyl-4-hydroxy-α-phenyl-1-piperidinepentanenitrile;
4-(4-Chlorophenyl)-4-hydroxy-α-phenyl-α-(1-piperidinyl)-1-piperidinepentanenitrile;
4-(4-Chlorophenyl)-4-hydroxy-α,α-diphenyl-1-piperidinepentanoic acid, methyl ester;
1-(5-Amino-4,4-diphenylpentyl)-4-(4-chlorophenyl)-4-piperidinol;
4-(4-Chlorophenyl)-4-hydroxy-1-[5-(1,5-cyclohexadien-1-yl)-5-phenylpentyl]piperidine;
and pharmaceutically acceptable salts thereof.

In yet another aspect, the composition useful in the methods of the invention comprises a compound of Formula (VI):

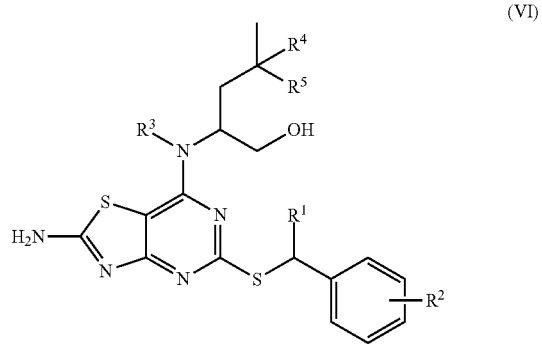

wherein:
R¹ is CH₃ or CH₃CH₂;
R² is H, 2-F, 2-Cl, 3-F, 3-OCH₃, 3-CN, 3-CF₃, 3-CONH₂ or 3-SO₂CH₃;

R³ is H or CH₃;
R⁴ is H or CH₃ and
R⁵ is H; or, when R⁴ is CH₃, R⁵ is H or F;
or a pharmaceutically acceptable salt thereof.

In one embodiment, the compound of Formula (VI) is selected from the group consisting of:
(2R)-2-[(2-amino-5-{[(1S)-1-(2-fluorophenyl)ethyl]thio}[1,3]thiazolo[4,5-d]pyrimidin-7-yl)amino]pentan-1-ol;
(2R)-2-[(2-amino-5-{[(1S)-1-(2-fluorophenyl)ethyl]thio}[1,3]thiazolo[4,5-d]pyrimidin-7-yl)amino]-4-methylpentan-1-ol;
(2R)-2-({2-amino-5-[(1-phenylethyl)thio][1,3]thiazolo[4,5-d]pyrimidin-7-yl}amino)-4-methylpentan-1-ol;
(2R)-2-[(2-amino-5-{[(1R)-1-phenylethyl]thio}[1,3]thiazolo[4,5-d]pyrimidin-7-yl)amino]-4-methylpentan-1-ol;
3-{(1S)-1-[(2-amino-7-{[(1R)-1-(hydroxymethyl)butyl]amino}[1,3]thiazolo[4,5-d]pyrimidin-5-yl)thio]ethyl}benzonitrile;
(2R)-2-{[2-amino-5-({(1S)-1-[3-(methyl sulfonyl)phenyl]ethyl}thio)[1,3]thiazolo[4,5-d]pyrimidin-7-yl]amino}-4-methylpentan-1-ol;
(2R)-2-[(2-amino-5-{[(1S)-1-phenylethyl]thio}[1,3]thiazolo[4,5-d]pyrimidin-7-yl)amino]pentan-1-ol;
3-{(1S)-1-[(2-amino-7-{[(1R)-1-(hydroxymethyl)-3-methylbutyl]amino} [1,3]thiazolo[4,5-d]pyrimidin-5-yl)thio]ethyl}benzonitrile;
(2R)-2-({2-amino-5-[(1-phenylpropyl)thio][1,3]thiazolo[4,5-d]pyrimidin-7-yl}amino)-4-methylpentan-1-ol;
3-{1-[(2-amino-7-{[(1R)-1-(hydroxymethyl)-3-methylbutyl] amino}[1,3]thiazolo[4,5-d]pyrimidin-5-yl)thio]ethyl}benzamide;
(2R)-2-{[2-amino-5-({1-[3-(trifluoromethyl)phenyl]ethyl}thio)[1,3]thiazolo[4,5-d]pyrimidin-7-yl]amino}-4-methylpentan-1-ol;
(2R)-2-[{2-amino-5-[(1-phenylethyl)thio][1,3]thiazolo[,5-d]pyrimidin-7-yl}(methyl)amino]-4-methylpentan-1-ol:
(2R)-2-[(2-amino-5-{[1-(2-chlorophenyl)ethyl]thio}[1,3]thiazolo[4,5-d]pyrimidin-7-yl)amino]-4-methylpentan-1-ol;
(2R)-2-[(2-amino-5-{[1-(3-methoxyphenyl)ethyl]thio}[1,3]thiazolo[4,5-d]pyrimidin-7-yl)amino]-4-111ethylpentan-1-ol;
(2R)-2-[(2-amino-5-{[(1S)-I-phenylethyl]thio}[1,3]thiazolo[4,5-d]pyrimidin-7-yl)amino]-4-methylpentan-1-ol;
(2R)-2-[(2-amino-5-{[(1S)-1-phenylethyl]thio}[1,3]thiazolo[4,5-d]pyrimidin-7-yl)amino]-4-fluoro-4-methylpentan-1-ol;
(2R)-2-[(2-amino-5-{[(1S)-I-(2-fluorophenyl)ethyl]thio}[1,3]thiazolo[4,5-d]pyrimidin-7-yl)amino]-4-fluoro-4-methylpentan-1-ol;
(2R)-2-[(2-amino-5-{[(1S)-1-(3-fluorophenyl)ethyl]thio}[1,3]thiazolo[4,5-d]pyrimidin-7-yl)amino]-4-methylpentan-1-ol;
and pharmaceutically acceptable salts thereof.

In yet another aspect, the composition useful in the methods of the invention comprises a compound of Formula (VII):

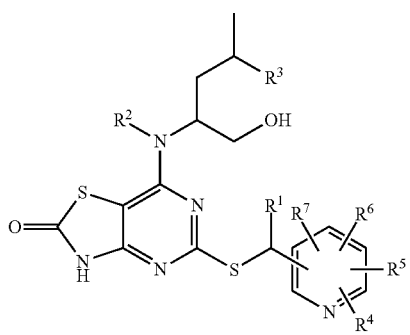

(VII)

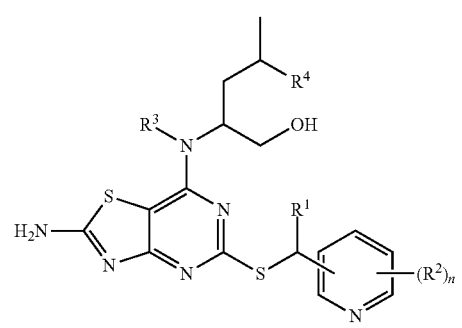

(VIII)

wherein:
R$^1$ is CH$_3$ or CH$_3$CH$_2$;
R$^2$ is H or CH$_3$;
R$^3$ is H or CH$_3$;
R$^4$, R$^5$, R$^6$ and R$^7$ are independently H, CH$_3$ or CH$_2$CH$_3$;
or a pharmaceutically acceptable salt thereof.

In one embodiment, the compound of Formula (VII) is selected from the group consisting of:
7-[(R)-1-hydroxy-4-methylpentan-2-ylamino]-5-[1-(pyridin-2-yl)ethylthio]thiazolo[4,5-d]pyrimidin-2(3H)-one;
7-[(R)-1-hydroxy-4-methylpentan-2-ylamino]-5-[1-(2,4-dimethylpyridin-2-yl)ethylthio]thiazolo[4,5-d]pyrimidin-2(3H)-one;
7-[(R)-1-hydroxy-4-methylpentan-2-ylamino]-5-[1-(2-methylpyridin-2-yl)ethylthio]thiazolo[4,5-d]pyrimidin-2(3H)-one;
7-[(R)-1-hydroxy-4-methylpentan-2-ylamino]-5-[1-(3-methylpyridin-2-yl)ethylthio]thiazolo[4,5-d]pyrimidin-2(3H)-one;
7-[(R)-1-hydroxy-4-methylpentan-2-ylamino]-5-[1-(2-ethylpyridin-2-yl)ethylthio]thiazolo[4,5-d]pyrimidin-2(3H)-one;
7-[(R)-1-hydroxy-4-methylpentan-2-ylamino]-5-[1-(3-ethylpyridin-2-yl)ethylthio]thiazolo[4,5-d]pyrimidin-2(3H)-one;
7-[(R)-1-hydroxy-4-methylpentan-2-ylamino]-5-[1-(3,5-dimethylpyridin-2-yl)ethylthio]thiazolo[4,5-d]pyrimidin-2(3H)-one;
7-[(R)-1-hydroxy-4-methylpentan-2-ylamino]-5-[1-(2,4-dimethylpyridin-2-yl)propylthio]thiazolo[4,5-d]pyrimidin-2(3H)-one;
7-[(R)-1-hydroxy-4-methylpentan-2-ylamino]-5-[1-(2-methylpyridin-2-yl)propylthio]thiazolo[4,5-d]pyrimidin-2(3H)-one;
7-[(R)-1-hydroxy-4-methylpentan-2-ylamino]-5-[1-(3-methylpyridin-2-yl)propylthio]thiazolo[4,5-d]pyrimidin-2(3H)-one;
7-[(R)-1-hydroxy-4-methylpentan-2-ylamino]-5-[1-(3,5-dimethylpyridin-2-yl)propylthio]thiazolo[4,5-d]pyrimidin-2(3H)-one;
7-[(R)-1-hydroxy-4-methylpentan-2-ylamino]-5-[(1S/R)-(pyridin-2-yl)ethylthio]thiazolo[4,5-d]pyrimidin-2(3H)-one;
7-[(R)-1-hydroxy-4-methylpentan-2-ylamino]-5-[(1R/S)-(pyridin-2-yl)ethylthio]thiazolo[4,5-d]pyrimidin-2(3H)-one;
and a pharmaceutically acceptable salt thereof.

In yet another aspect, the composition useful in the methods of the invention comprises a compound of Formula (VIII):

wherein:
R$^1$ is CH$_3$ or CF$_3$;
R$^2$ is halo, CN or C$_1$-C$_6$ alkyl;
R$^3$ and R$^4$ are independently H or CH$_3$;
n is 0, 1 or 2;
or a pharmaceutically acceptable salt thereof.

In one embodiment, the compound of Formula (VIII) is selected from the group consisting of:
(2R)-2-[(2-amino-5-{[1-(5-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-l-(5-chloropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(5-fluoropyridin-2-yl)ethyl]thio}[1,3]thiazolo[4,5-d]pyrimidin-7-yl)amino]-4-methylpentan-1-ol;
(2R)-2-[(2-amino-5-{[1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1R)-1-(3-chloropyridin-4-yl)ethyl]thio}[1,3]thiazolo[4,5-d]pyrimidin-7-yl)amino]-4-methylpentan-1-ol;
(2R)-2-[(2-amino-5-{[(1S)-1-(3-fluoropyridin-2-yl)ethyl]thio}[1,3]thiazolo[4,5-d]pyrimidin-7-yl)amino]-4-methylpentan-1-ol;
(2R)-2-[(2-amino-5-{[(1S)-1-(6-chloropyridin-3-yl)ethyl]thio}[1,3]thiazolo[4,5-d]pyrimidin-7-yl)(methyl)amino]pentan-1-ol;
(2R)-2-[(2-amino-5-{[(1S)-1-(6-chloropyridin-3-yl)ethyl]thio}[1,3]thiazolo[4,5-d]pyrimidin-7-yl)amino]pentan-1-ol; and
2-{(1S)-1-[(2-amino-7-{[(1R)-1-(hydroxymethyl)-3-methylbutyl]amino}[1,3]thiazolo[4,5-d]pyrimidin-5-yl)thio]ethyl}isonicotinonitrile;
and a pharmaceutically acceptable salt thereof.

In yet another aspect, the composition useful in the methods of the invention comprises a compound of Formula (IX):

$$R^A\text{—}R^B \qquad (IX)$$

wherein:
R^A is a group selected from the group consisting of:
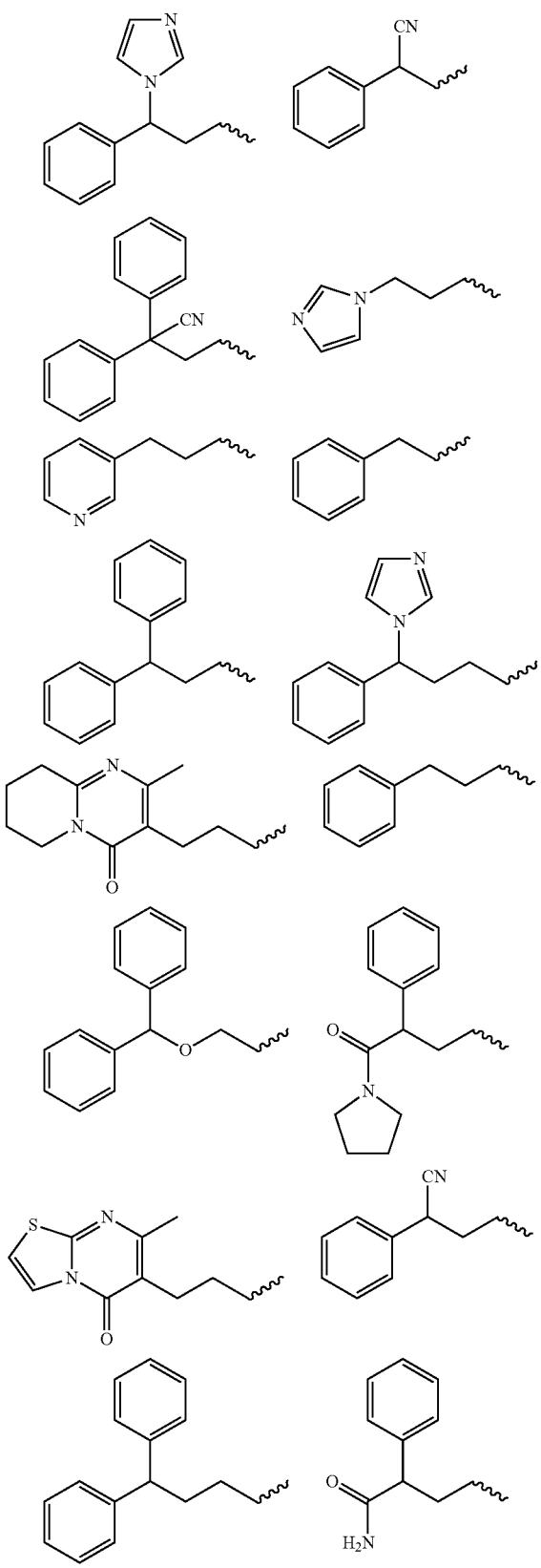
and,
R^B is a group selected from the group consisting of:
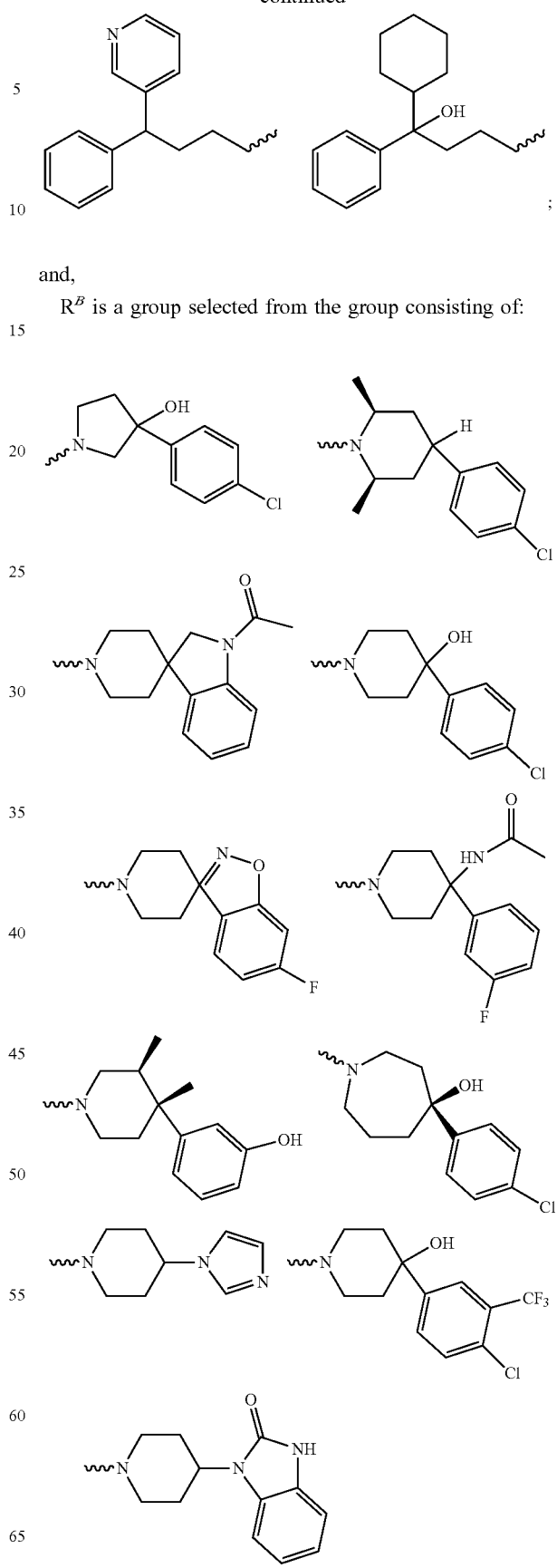

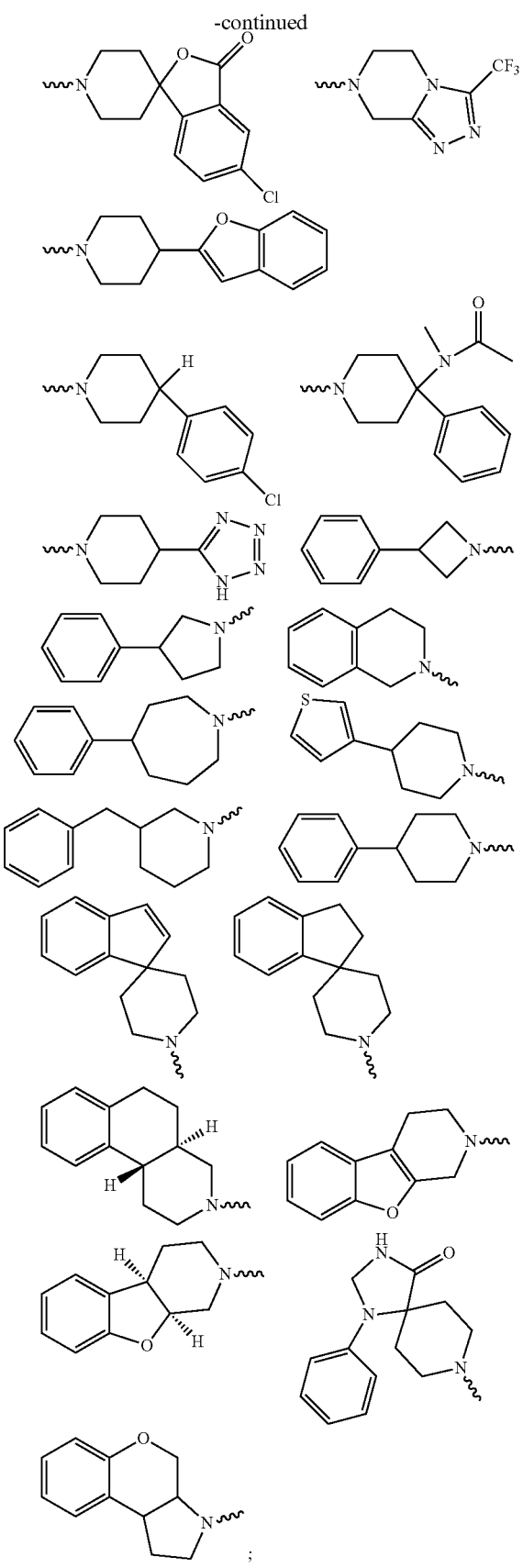

; or a pharmaceutically acceptable salt thereof.

In yet another aspect, the composition useful in the methods of the invention comprises a compound of Formula (X):

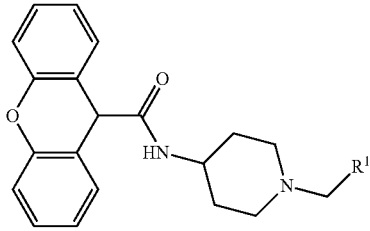

(X)

wherein $R^1$ is $(C_1-C_8)$ alkyl, substituted $(C_1-C_8)$ alkyl, phenyl, substituted phenyl, $(C_1-C_8)$ cycloalkyl or substituted $(C_1-C_8)$ cycloalkyl, or a pharmaceutically acceptable salt thereof.

In one embodiment, in Formula (X) $R^1$ is n-hexyl, phenyl or cyclopentyl.

In yet another aspect, the composition useful in the methods of the invention comprises a compound of (XI):

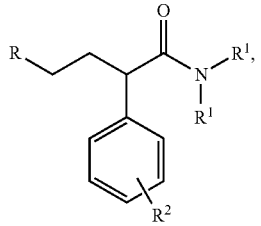

(XI)

wherein

R is selected from the group consisting of:

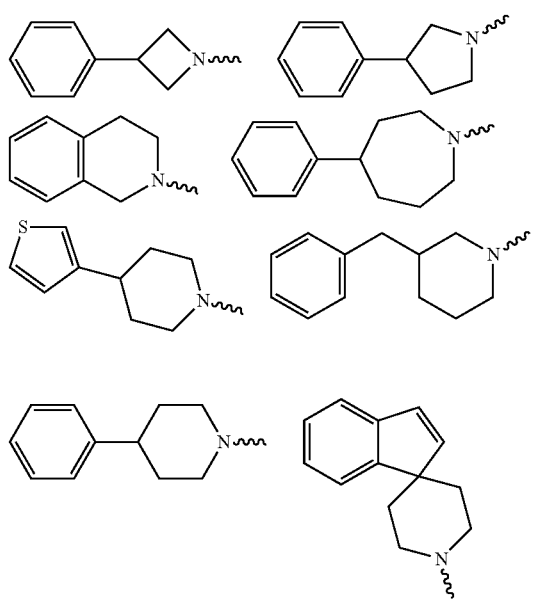

-continued

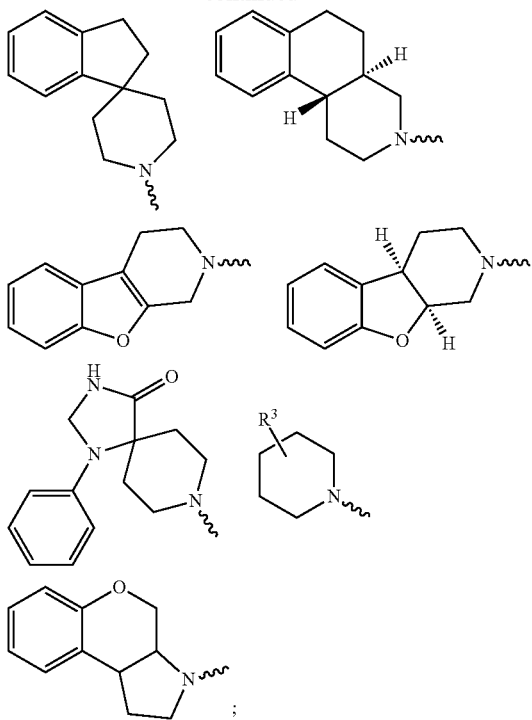

each occurrence of $R^1$ and $R^4$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

or a pharmaceutically acceptable salt thereof.

In yet another aspect, the composition useful in the methods of the invention comprises a compound of Formula (XII):

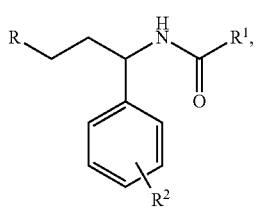

(XII)

wherein

R is selected from the group consisting of:

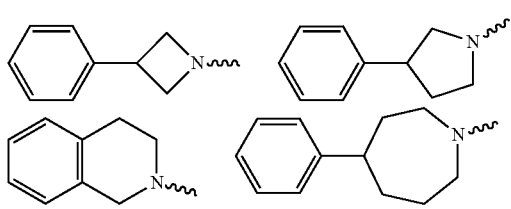

-continued

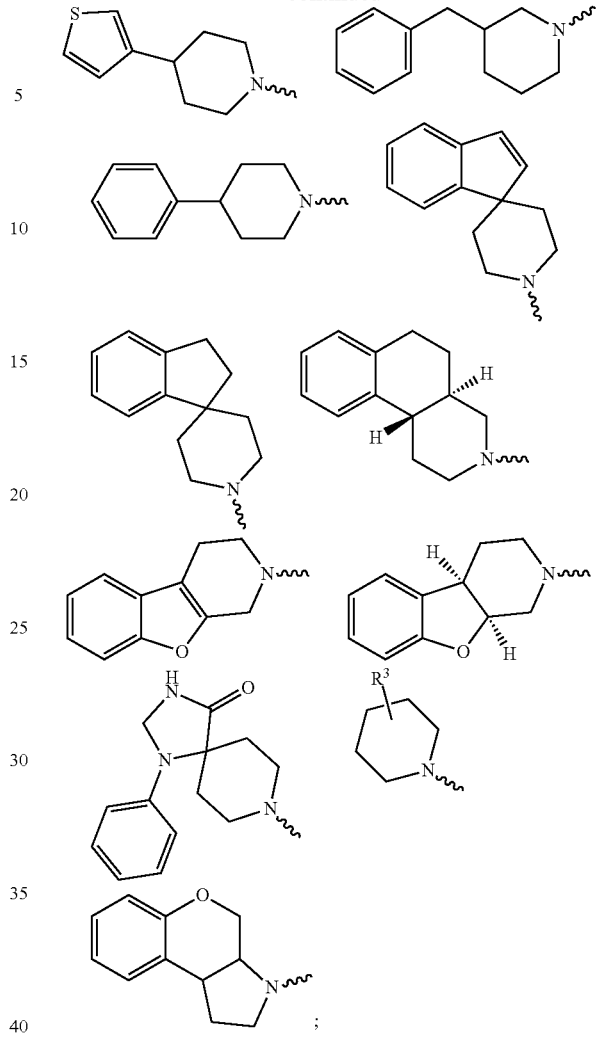

each occurrence of $R^1$ and R4 and $R^5$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

or a pharmaceutically acceptable salt thereof.

In yet another aspect, the composition useful in the methods of the invention comprises a compound selected from the group consisting of:

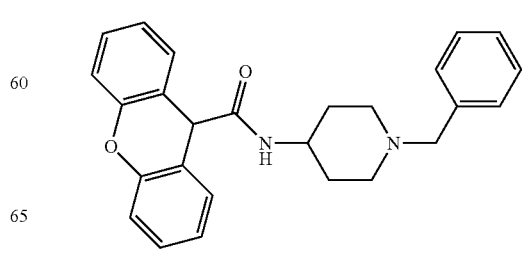

-continued

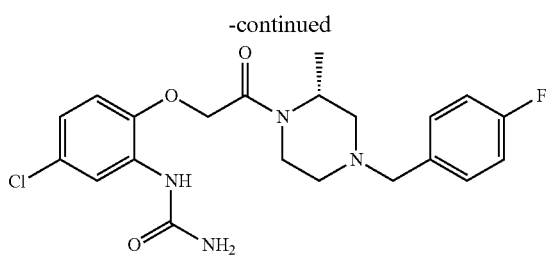
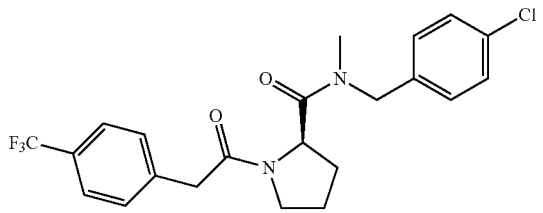
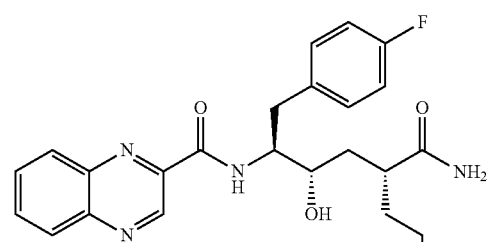
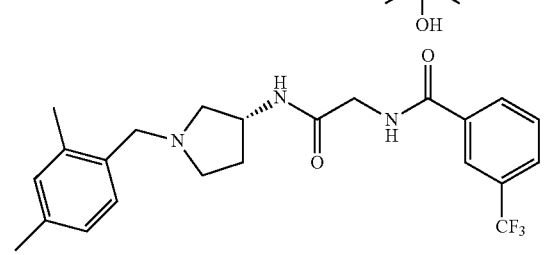
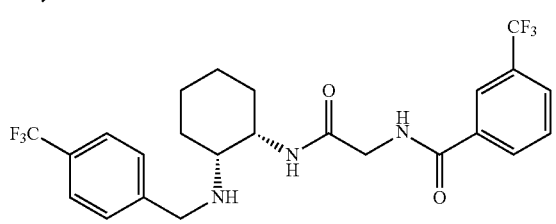
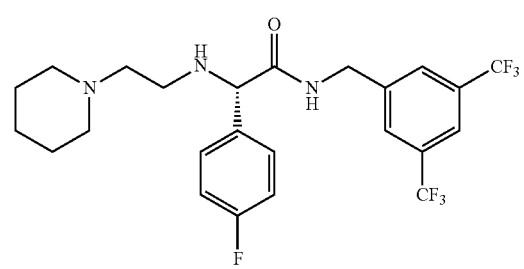
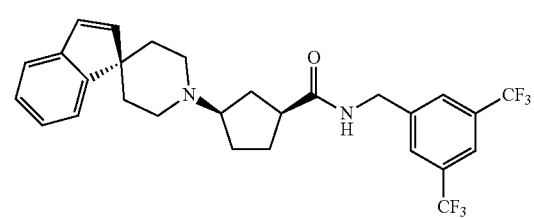

-continued

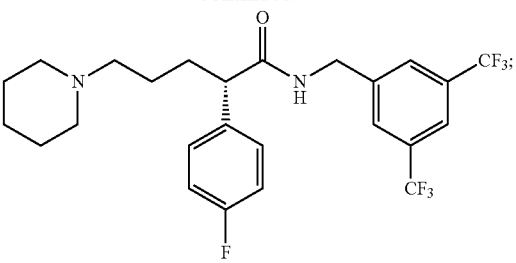

or a pharmaceutically acceptable salt thereof.

Preparation of Compounds

The compounds useful within the methods of the invention may be prepared using methods known to those skilled in the art.

In a non-limiting example, exemplar compounds of Formula (I) may be prepared using the methodology illustrated in Ng et al., 1999, J. Med. Chem. 42:4680-94.

In a non-limiting example, exemplar compounds of Formula (I) may be prepared using the chemistry illustrated below:

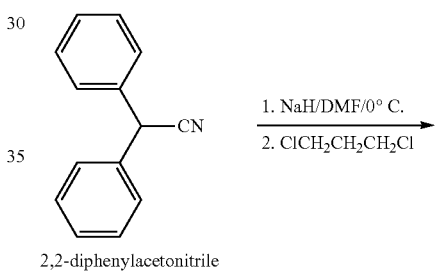
2,2-diphenylacetonitrile

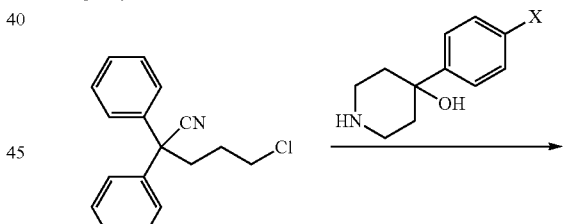

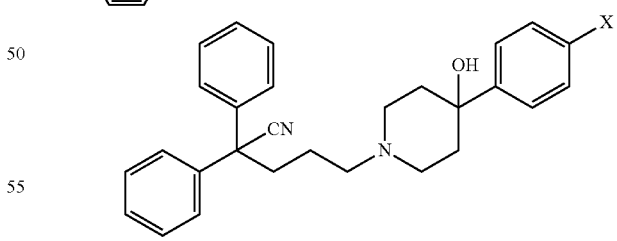

X = H or Cl

In a non-limiting example, exemplar compounds of Formula (I) may be prepared using the chemistry illustrated below. The intermediate pyrrolo[1,2-a] quinoxalin-4(5H)-one may be obtained from commercial sources or synthesized according to literature procedures (Campiani et al., 1991, Synth. Commun. 21:1567-1576; Prunier et al., 1997, J. Med. Chem. 40:1808-1819).

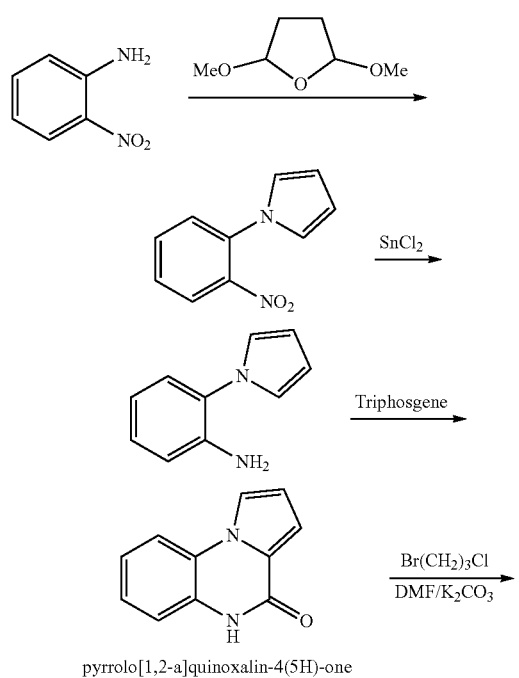

pyrrolo[1,2-a]quinoxalin-4(5H)-one

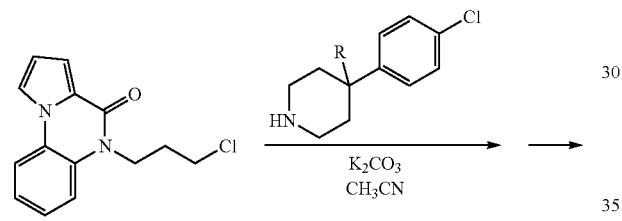

R = OH
R = H

The starting material pyrido[3,4-e]pyrrolo[1,2-a]pyrazin-6(5H)-one may be prepared according to the following procedure (Prunier et al., 1997, J. Med. Chem. 40:1808; Guilon, 2004, J. Med. Chem. 47:1997):

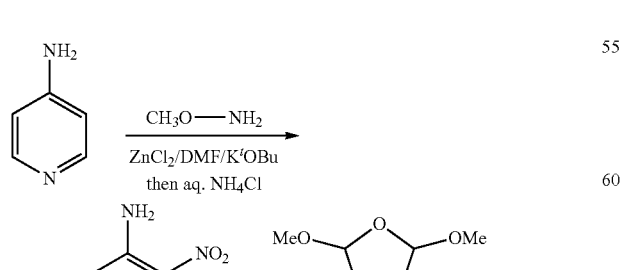

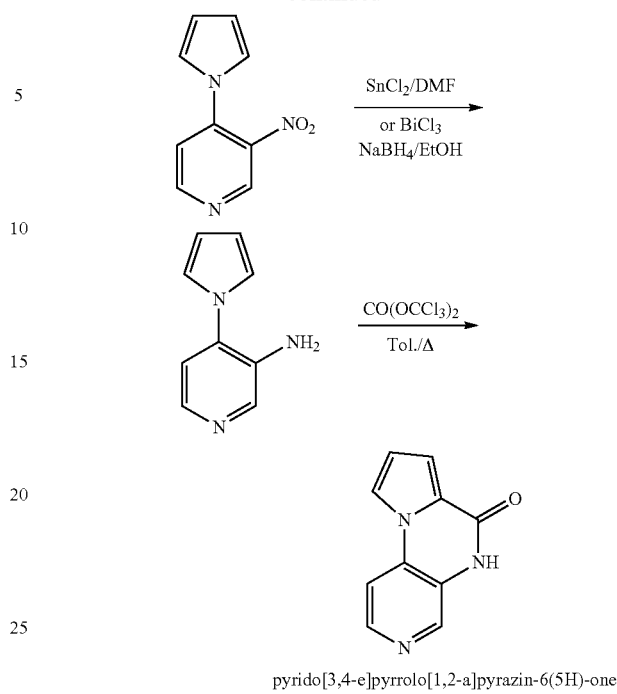

pyrido[3,4-e]pyrrolo[1,2-a]pyrazin-6(5H)-one

The starting material pyrido[3,4-e]pyrrolo[1,2-a]pyrazin-6(5H)-one may also be prepared according to the following procedure (Prunier et al., 1997, J. Med. Chem. 40:1808):

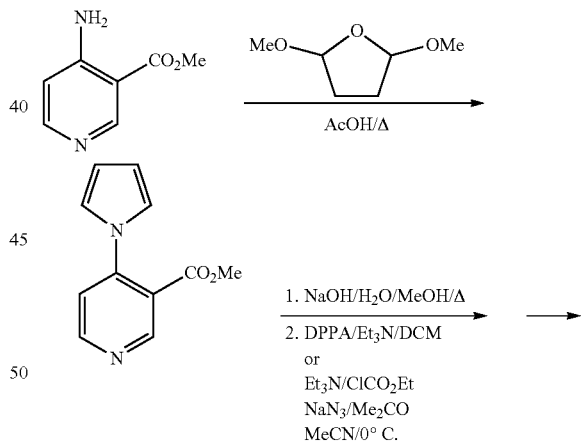

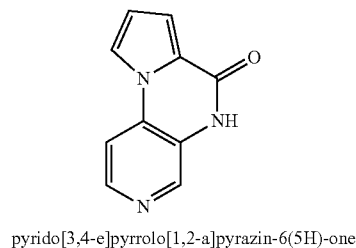

pyrido[3,4-e]pyrrolo[1,2-a]pyrazin-6(5H)-one

The starting material pyrrolo[1,2-a]thieno[3,2-e]pyrazin-5(4H)-one may be prepared according to the following procedure (Rault et al., 1996, J. Med. Chem. 39:2068):

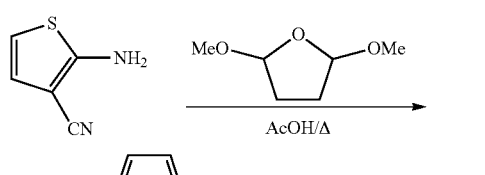
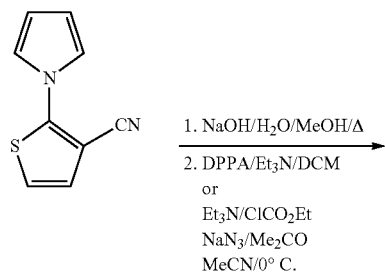
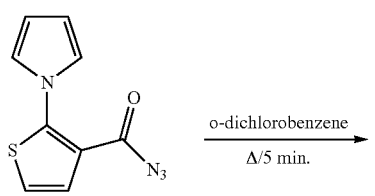
pyrrolo[1,2-a]thieno[3,2-e]pyrazin-5(4H)-one
The starting material 1-methyl-1H-pyrazolo[4,3-e]pyrrolo[1,2-a]pyrazin-5(4H)-one may be prepared according to the following procedure (PCT Appl. Publ. No. WO 2011/074709):
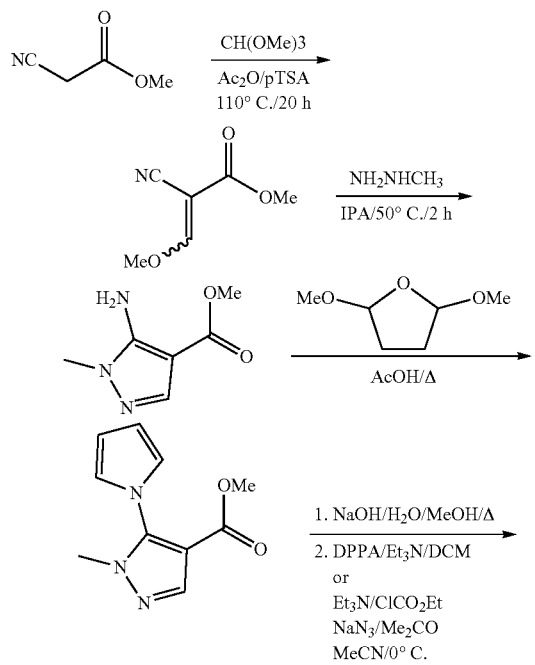
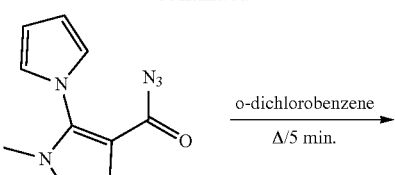
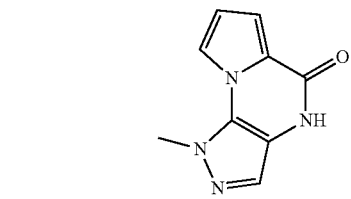
1-methyl-1H-pyrazolo[4,3-e]pyrrolo[1,2-a]pyrazin-5(4H)-one
The following intermediates may be prepared according to the reaction schemes outlined:
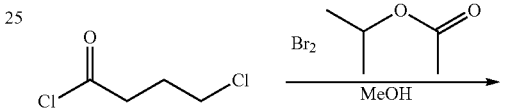
U.S. Pat. No. 6,506,907
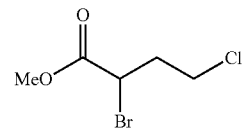
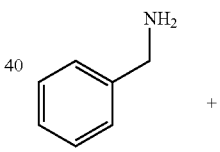
+
WO2008/84300
US2007/117796
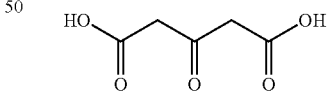
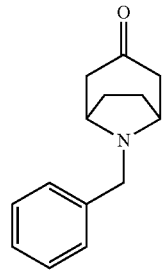

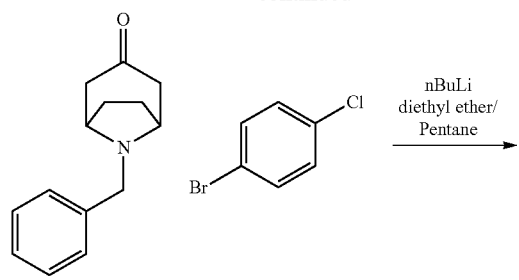
WO2010/23161 A1 US2007/179158 A1
WO2007/25978 A1 US2009/62334 A1
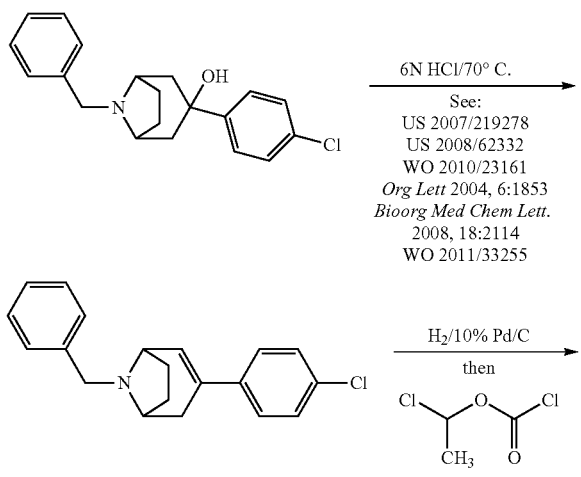
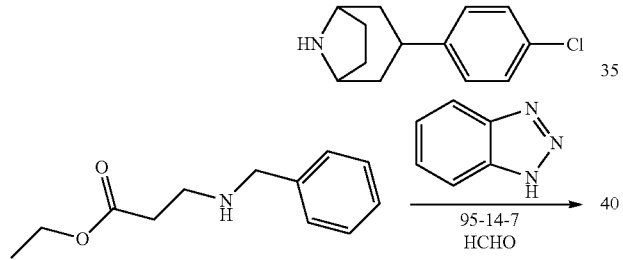
WO 2005040120
WO 2010090875
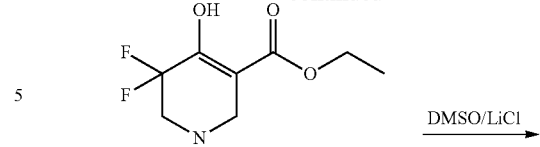
EP 2123651
BMCL 2009, 6762
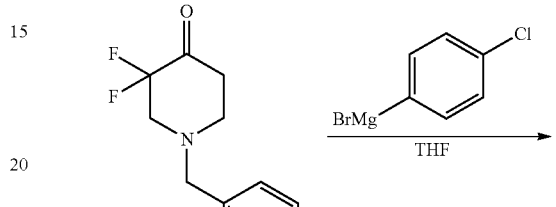
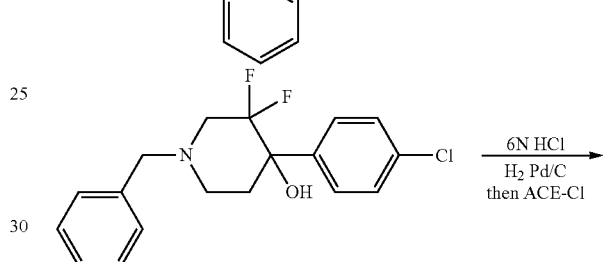
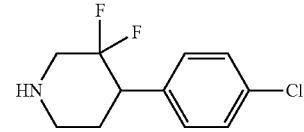 [SMILES: FC1(F)CNCCC1c1ccc(Cl)cc1]
In a non-limiting example, the compound of Formula (I) 5-(3-(4-(4-chlorophenyl) piperidin-1-yl)cyclopentyl)pyrrolo[1,2-a]quinoxalin-4(5H)-one may be prepared according to the following synthetic scheme:
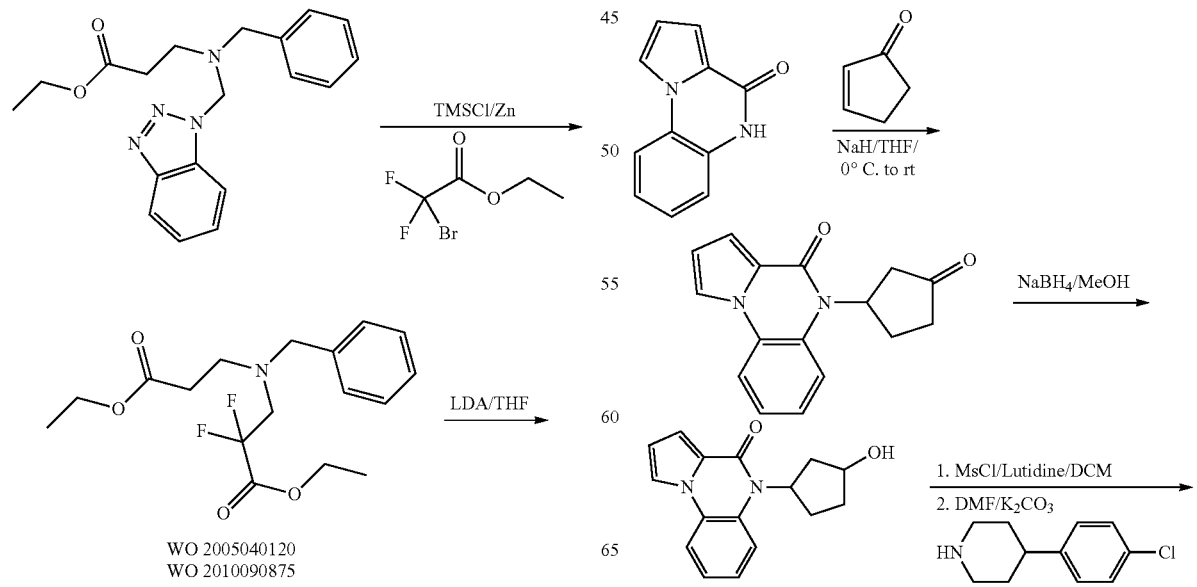

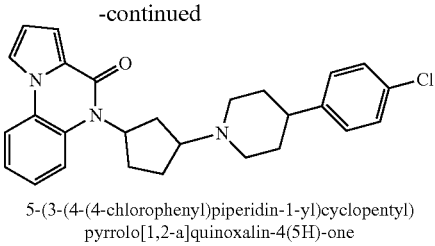

5-(3-(4-(4-chlorophenyl)piperidin-1-yl)cyclopentyl) pyrrolo[1,2-a]quinoxalin-4(5H)-one In a non-limiting example, the compound of Formula (I) 6-(2-(4-(4-chlorophenyl)piperidin-1-yl)ethyl)benzo[b]pyrrolo[1,2-d][1,4]oxazepin-7(6H)-one may be prepared according to the following synthetic scheme:

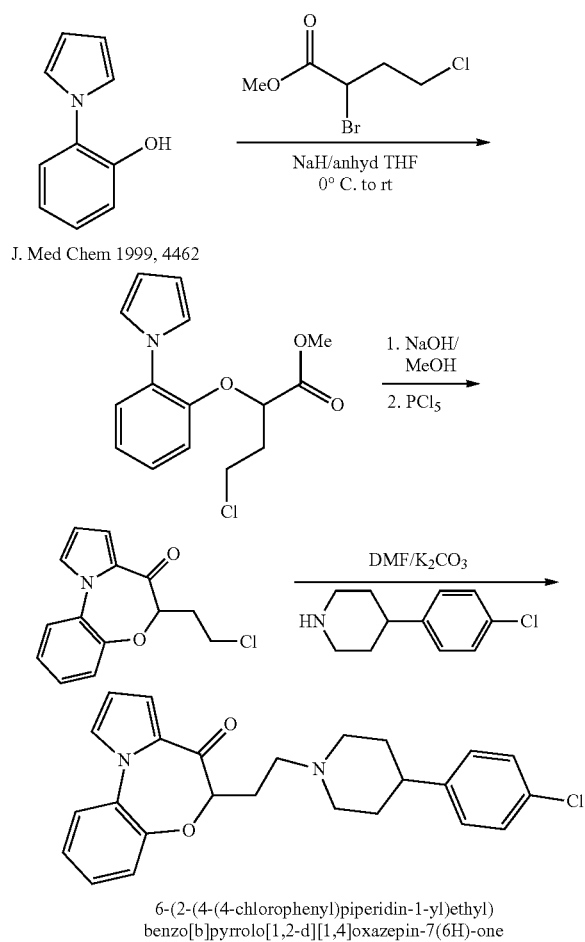

6-(2-(4-(4-chlorophenyl)piperidin-1-yl)ethyl) benzo[b]pyrrolo[1,2-d][1,4]oxazepin-7(6H)-one In a non-limiting example, the compounds of Formula (II)-(V) may be prepared using the methodology illustrated in U.S. Patent Application Publication No. US 20070142386, hereby incorporated in its entirety by reference.

In a non-limiting example, the compounds of Formula (VI) may be prepared using the methodology illustrated in U.S. Patent Application Publication No. US 20080214578, hereby incorporated in its entirety by reference.

In a non-limiting example, the compounds of Formula (VII) may be prepared using the methodology illustrated in International Patent Application Publication No. WO 20091201490, hereby incorporated in its entirety by reference.

In a non-limiting example, the compounds of Formula (VIII) may be prepared using the methodology illustrated in International Patent Application Publication No. WO 2008039139, hereby incorporated in its entirety by reference, and Walters et al., 2008, Bioorg. Med. Chem. Lett. 18:798-803.

In a non-limiting example, the compounds of Formula (IX) may be prepared using the methodology illustrated in the scheme below:

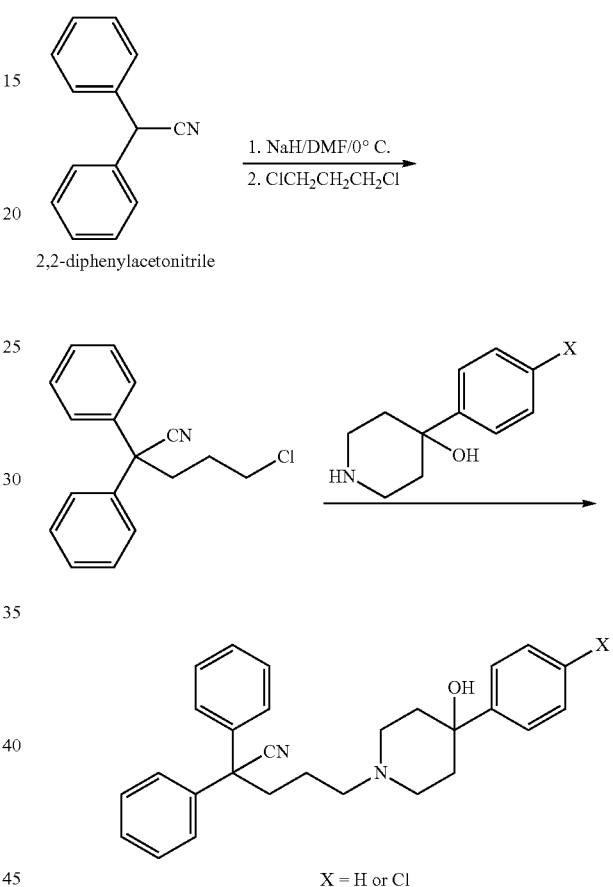

X = H or Cl

In a non-limiting example, the compounds of Formula (X) may be prepared using the methodology illustrated in the scheme below:

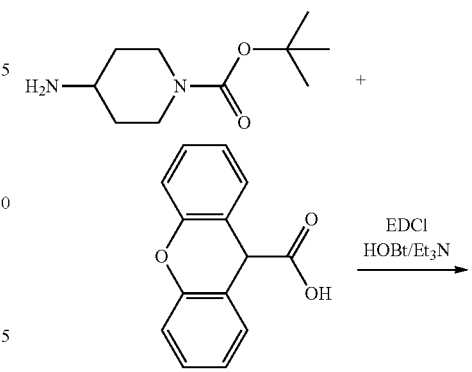

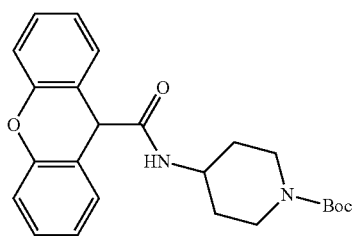
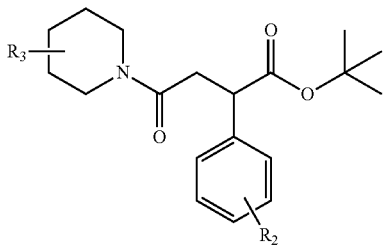
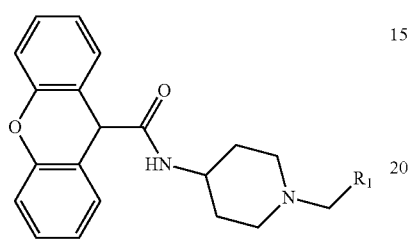
In a non-limiting example, the compounds of Formula (XI) may be prepared using the methodology illustrated in the scheme below:
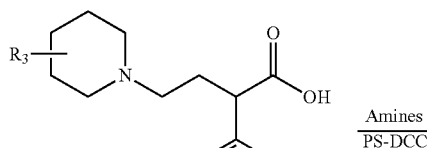
In a non-limiting example, the compounds of Formula (XII) may be prepared using the methodology illustrated in the scheme below:
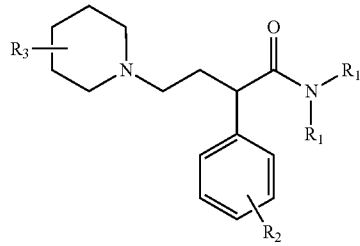
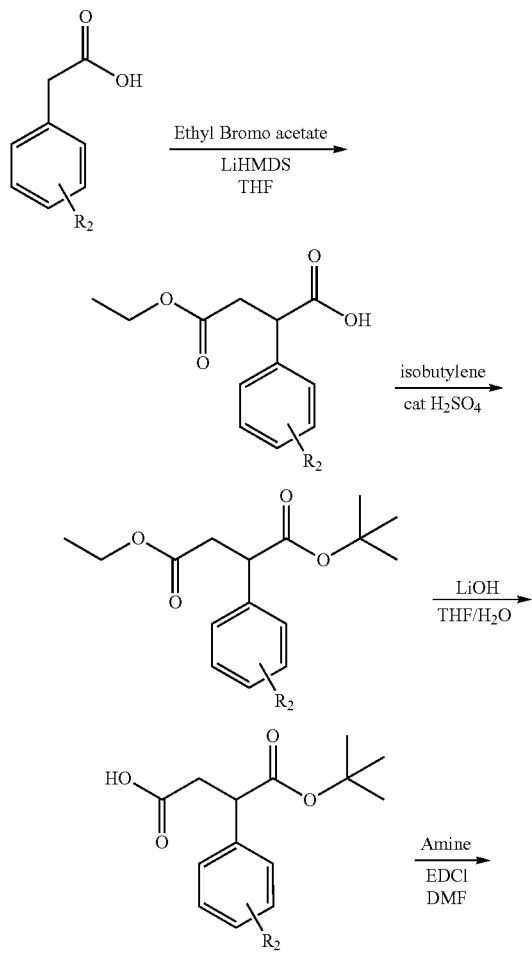
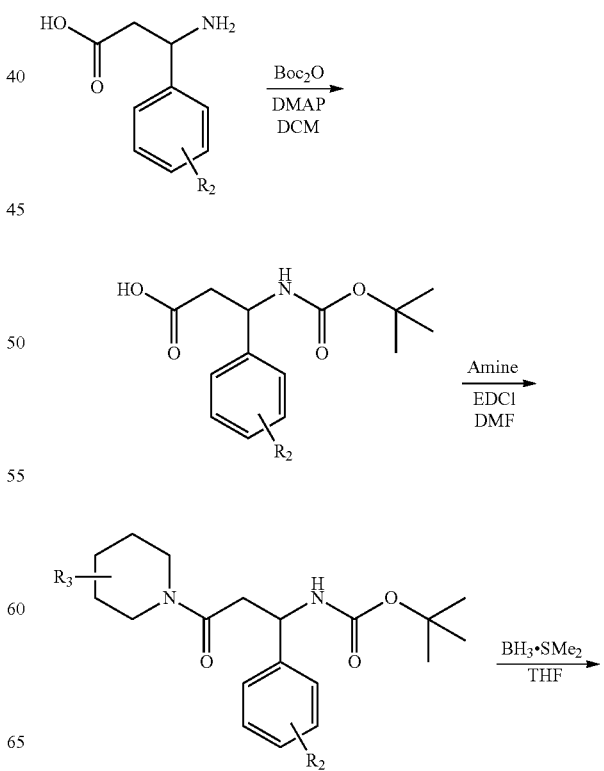

-continued

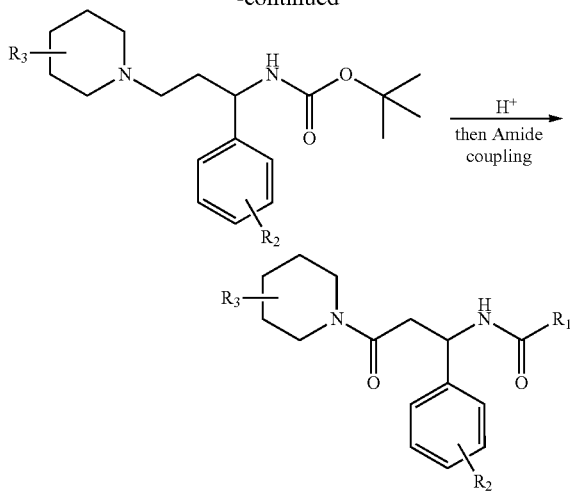

Salts

The compounds described herein may form salts with acids, and such salts are included in the present invention. In one embodiment, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Compositions

The invention includes a composition comprising:
(i) a compound of formula (I)

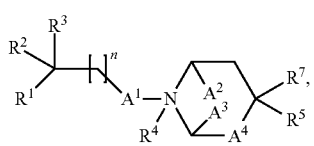

(I)

wherein:
A$^1$ is CH$_2$ or cyclopentane-1,3-diyl;
n is 0, 1, 2, 3, 4 or 5 if A is CH$_2$, or n is 0, 1, or 2 if A is cyclopentane-1,3-diyl;

A$^2$ and A$^3$ are both H; or A$^2$ and A$^3$ combine to form a divalent radical selected from the group consisting of methanediyl, ethane-1,2-diyl, or propane-1,3-diyl;
A$^4$ is CH$_2$, CH(CF$_3$), or CF$_2$;
R$^1$ and R$^2$ are both H, and R$^3$ is selected from the group consisting of:

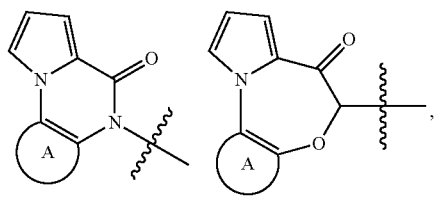

wherein ring A is selected from the group consisting of phenyl, substituted phenyl, pyridinyl, substituted pyridinyl, thiophenyl, substituted thiophenyl, 1H-pyrazole, and 1-(C$_1$-C$_6$) alkyl-1H-pyrazole;

R$^4$ is nil or (C$_1$-C$_6$)alkyl, wherein if R$^4$ is (C$_1$-C$_6$)alkyl, compound (I) is a quaternary ammonium salt;

R$^5$ is (C$_1$-C$_6$)alkyl, substituted (C$_1$-C$_6$)alkyl, phenyl, substituted phenyl, heteroaryl, substituted heteroaryl;

R$^6$ is H, (C$_1$-C$_6$)alkyl, substituted (C$_1$-C$_6$)alkyl, aryl or substituted aryl; and, R$^7$ is OH, CH$_2$OH, or C(=O)OR$^6$;
or a salt thereof.

(ii) a compound of Formula (IX):

$$R^A—R^B \qquad (IX)$$

wherein:
R$^A$ is a group selected from the group consisting of:

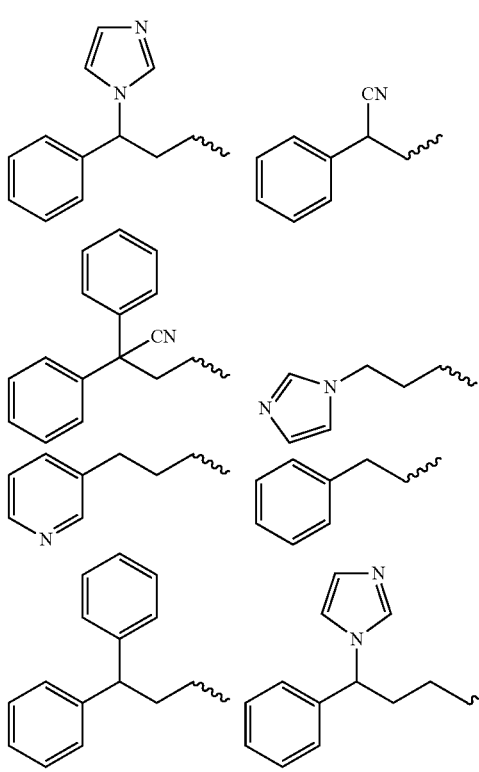

-continued
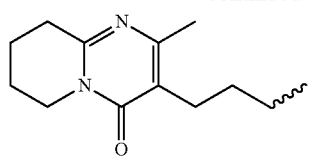
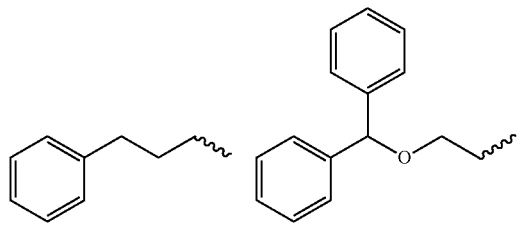
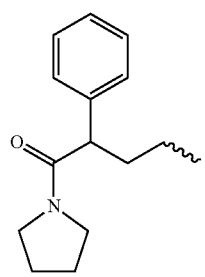
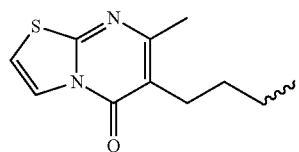
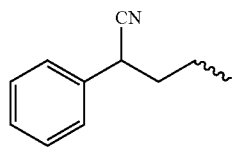
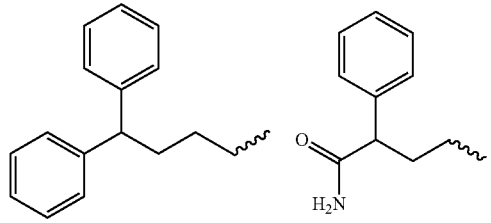
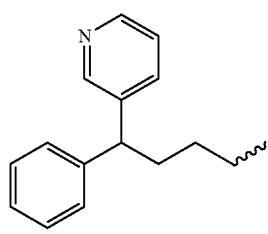
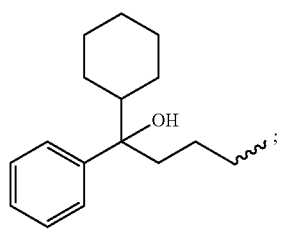
$R^B$ is a group selected from the group consisting of:
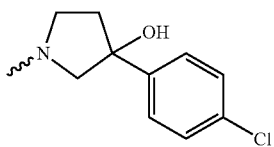
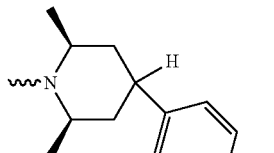
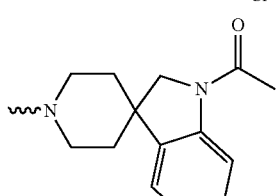
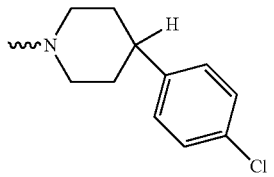
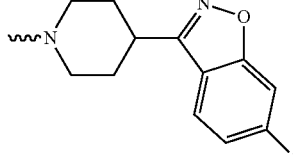
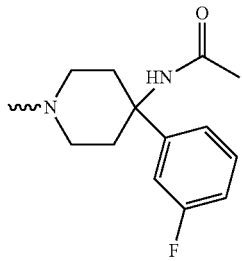
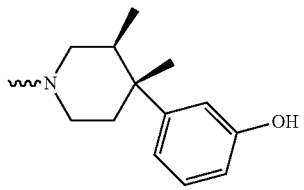
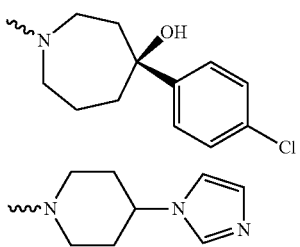

-continued
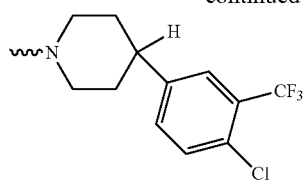
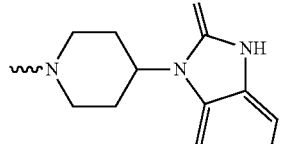
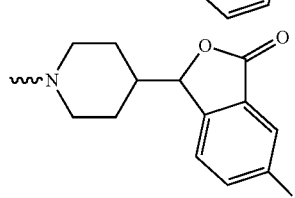
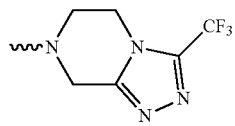
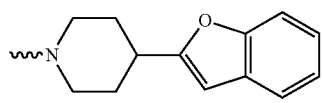
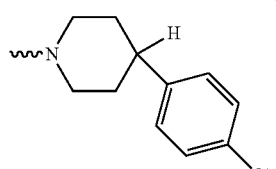
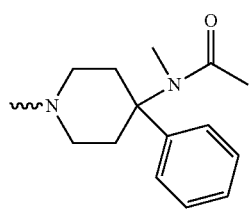
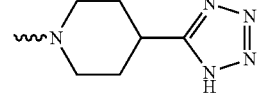
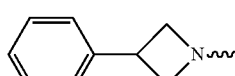
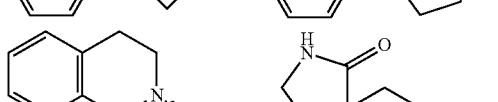
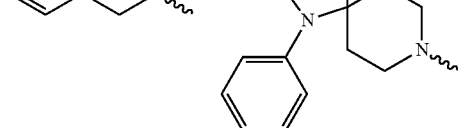
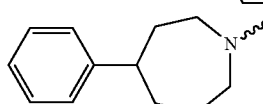
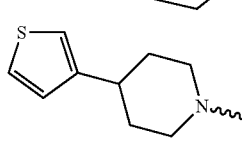
-continued
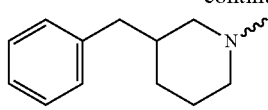
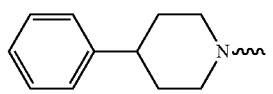
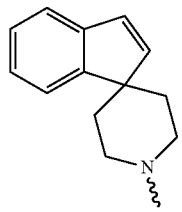
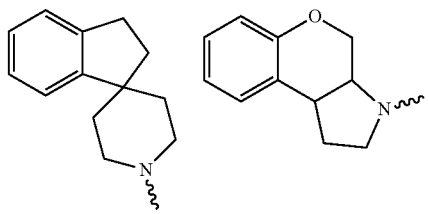
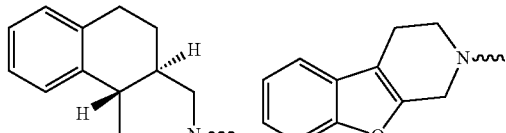
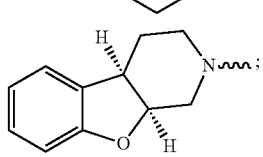
(iii) a compound of Formula (X):
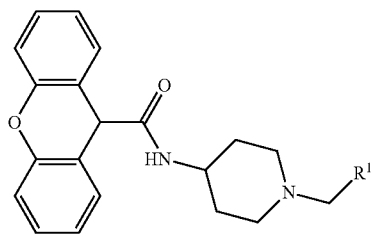
(X)
wherein $R^1$ is $(C_1-C_8)$ alkyl, substituted $(C_1-C_8)$ alkyl, phenyl, substituted phenyl, $(C_1-C_8)$ cycloalkyl or substituted $(C_1-C_8)$ cycloalkyl;
(iv) a compound of Formula (XI):
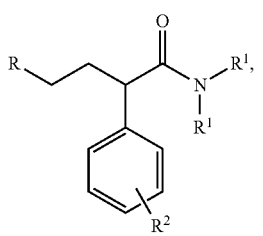
(XI)

wherein
R is selected from the group consisting of:

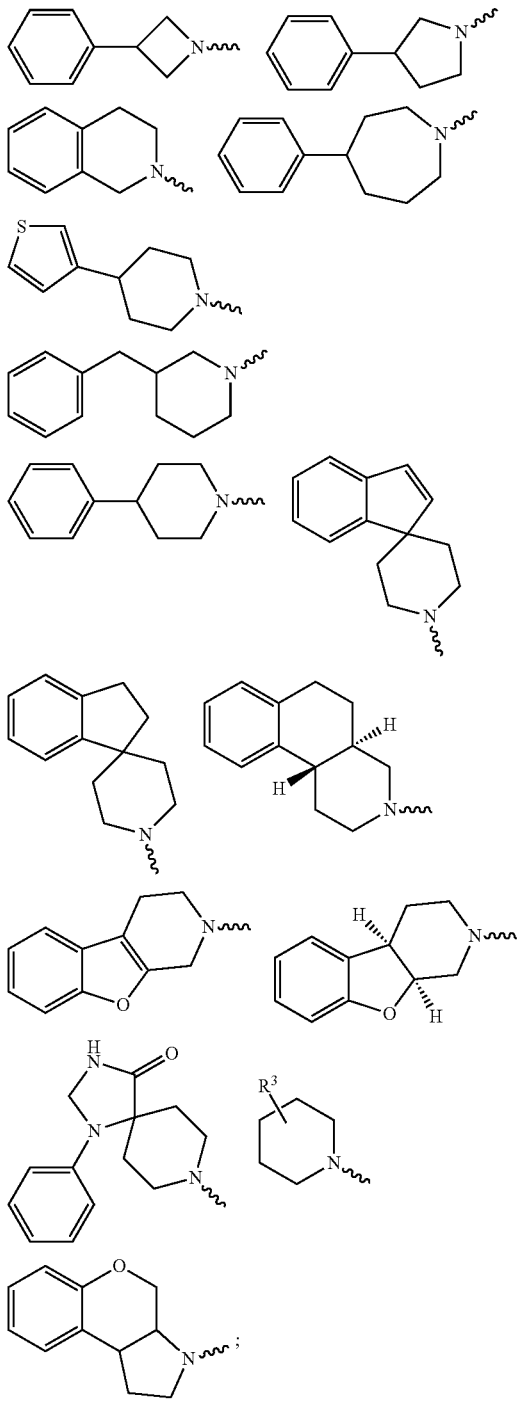

each occurrence of $R^1$ and $R^4$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

(v) a compound of Formula (XII):

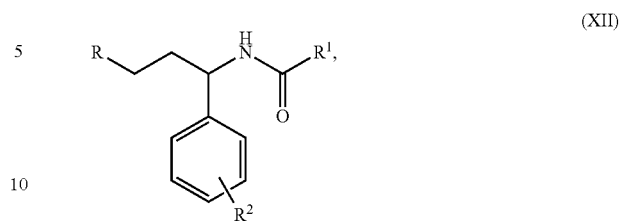

wherein
R is selected from the group consisting of:

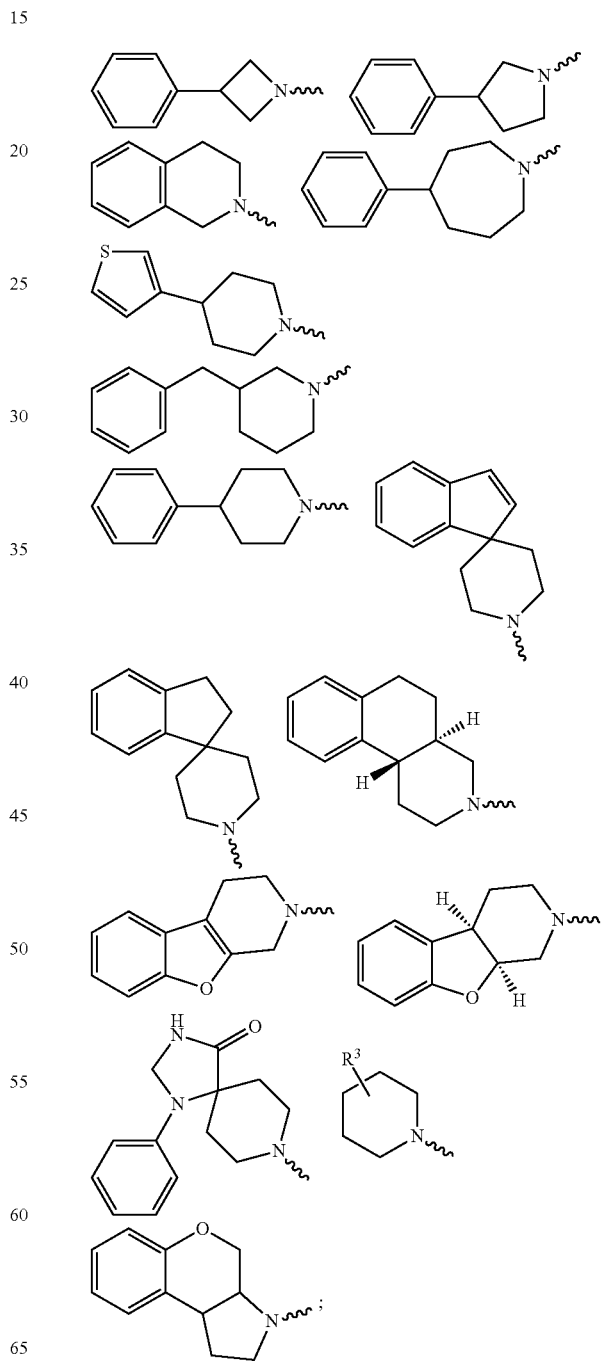

each occurrence of $R^1$, $R^4$ and $R^5$ is independently H, ($C_1$-$C_6$) alkyl, substituted ($C_1$-$C_6$) alkyl, phenyl, substituted phenyl, ($C_1$-$C_6$) cycloalkyl, or substituted ($C_1$-$C_6$) cycloalkyl; and, $R^2$ and $R^3$ are independently H, ($C_1$-$C_6$) alkyl, substituted ($C_1$-$C_6$) alkyl, phenyl, substituted phenyl, ($C_1$-$C_6$) cycloalkyl, substituted ($C_1$-$C_6$) cycloalkyl, halo, $OR^4$, $N(R^4)$ ($R^4$), $NO_2$, or NHAc;

or a pharmaceutically acceptable salt thereof.

Antibodies of the Invention

The invention also includes a composition comprising a $CX_3CR1$ antibody. The invention also includes a composition comprising a fractalkine antibody. In one embodiment, the fractalkine antibody is directed to soluble fractalkine. In another embodiment, the fractalkine antibody is directed to membrane associated fractalkine. In yet one embodiment, the antibody comprises an antibody selected from a polyclonal antibody, a monoclonal antibody, a humanized antibody, a synthetic antibody, a heavy chain antibody, a human antibody, and a biologically active fragment of an antibody.

It will be appreciated by one skilled in the art that an antibody comprises any immunoglobulin molecule, whether derived from natural sources or from recombinant sources, which is able to specifically bind to an epitope present on a target molecule.

In one aspect of the invention, $CX_3CR1$ is directly inhibited by an antibody that specifically binds to an epitope on $CX_3CR1$. In another aspect of the invention, the effects of $CX_3CR1$ are blocked by an antibody that specifically binds to an epitope on a downstream effector. In still another aspect of the invention, the effects of $CX_3CR1$ are blocked by an antibody that binds to an epitope of an upstream regulator of $CX_3CR1$.

When the $CX_3CR1$ inhibitor used in the compositions and methods of the invention is a polyclonal antibody (IgG), the antibody is generated by inoculating a suitable animal with a peptide comprising full length $CX_3CR1$ protein, or a fragment thereof, an upstream regulator, or fragments thereof. These polypeptides, or fragments thereof, may be obtained by any methods known in the art, including chemical synthesis and biological synthesis, as described elsewhere herein. In this regard, an exemplary $CX_3CR1$ sequence is SEQ ID NO:1. Antibodies produced in the inoculated animal which specifically bind to $CX_3CR1$, or fragments thereof, are then isolated from fluid obtained from the animal.

In one aspect of the invention, fractalkine is directly inhibited by an antibody that specifically binds to an epitope on fractalkine. In another aspect of the invention, the effects of fractalkine are blocked by an antibody that specifically binds to an epitope on a downstream effector. In still another aspect of the invention, the effects of fractalkine are blocked by an antibody that binds to an epitope of an upstream regulator of fractalkine.

When the fractalkine inhibitor used in the compositions and methods of the invention is a polyclonal antibody (IgG), the antibody is generated by inoculating a suitable animal with a peptide comprising full length fractalkine protein, or a fragment thereof, an upstream regulator, or fragments thereof. These polypeptides, or fragments thereof, may be obtained by any methods known in the art, including chemical synthesis and biological synthesis, as described elsewhere herein. In this regard, an exemplary fractalkine sequence is SEQ ID NO:2. Antibodies produced in the inoculated animal which specifically bind to fractalkine, or fragments thereof, are then isolated from fluid obtained from the animal.

Antibodies may be generated in this manner in several non-human mammals such as, but not limited to goat, sheep, horse, camel, rabbit, and donkey. Methods for generating polyclonal antibodies are well known in the art and are described, for example in Harlow, et al. (1998, In: Antibodies, A Laboratory Manual, Cold Spring Harbor, N.Y.).

Monoclonal antibodies directed against a full length $CX_3CR1$ or fractalkine, or fragments thereof, may be prepared using any well-known monoclonal antibody preparation procedures, such as those described, for example, in Harlow et al. (1998, In: Antibodies, A Laboratory Manual, Cold Spring Harbor, N.Y.) and in Tuszynski et al. (1988, Blood, 72:109-115). Human monoclonal antibodies may be prepared by the method described in U.S. Patent Publication No. 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al. (1992, Critical Rev. Immunol. 12(3,4):125-168) and the references cited therein.

When the antibody used in the methods of the invention is a biologically active antibody fragment or a synthetic antibody corresponding to antibody to a full length CX3CR1 or fractalkine, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3,4):125-168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen et al. (U.S. Pat. No. 6,180,370), Wright et al., (1992, Critical Rev. Immunol. 12(3,4):125-168) and in the references cited therein, or in Gu et al. (1997, Thrombosis & Hematocyst 77(4):755-759), or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well-known procedures. Preferably, the human constant region DNA sequences are isolated from immortalized B-cells as described in International Patent Application Publication No. WO 198702671. CDRs useful in producing the antibodies of the present invention may be similarly derived from DNA encoding monoclonal antibodies capable of binding to the target molecule. Such humanized antibodies may be generated using well-known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al. (1998, Antibodies: A Laboratory Manual, Cold Spring Harbor, N.Y.).

$V_H$ proteins isolated from other sources, such as animals with heavy chain disease (Seligmann et al., 1979, Immunological Rev. 48:145-167, incorporated herein by reference in its entirety), are also useful in the compositions and methods of the invention. The present invention further comprises variable heavy chain immunoglobulins produced from mice and other mammals, as detailed in Ward et al. (1989, Nature 341:544-546, incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as $CX_3CR1$ or fractalkine inhibitors in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage that encode the desired antibody may be engineered such that the protein is displayed on the surface thereof in such a manner that it is available for binding to its corresponding binding protein, e.g., the antigen against which the antibody is directed. Thus, when bacteriophage that express a specific antibody are incubated in the presence of a cell which expresses the corresponding antigen, the bacteriophage will bind to the cell. Bacteriophage that do not express the antibody will not bind to the cell. Such panning techniques are well known in the art and are described for example, in Wright et al. (1992, Critical Rev. Immunol. 12(3,4): 125-168).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used to practice the method of the invention, or to prepare a pharmaceutical composition useful in practicing the method of the invention.

The antibodies of the present invention can be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Current Protocols in Molecular Biology, (Ausubel et al., eds.), Greene Publishing Associates and Wiley-Interscience, New York (2002)). Exemplary immunoassays are described briefly below (but are not intended to be in any way limiting).

Methods of the Invention

The invention includes a method of preventing or treating metastasis in a subject diagnosed with cancer. The method comprises the step of administering to the subject in need thereof an effective amount of a pharmaceutical formulation comprising at least one pharmaceutically acceptable carrier and at least one $CX_3CR1$ or fractalkine antagonist.

In one embodiment, the subject is subjected to primary surgery related to the cancer. In another embodiment, administration of the pharmaceutical formulation takes place before, during or after the primary surgery. In yet another embodiment, the cancer includes breast cancer or prostate cancer. In yet another embodiment, the metastasis includes bone metastasis. In yet another embodiment, the administration starts at least 6 months before the primary surgery. In yet another embodiment, the administration starts at least 3 months before the primary surgery. In yet another embodiment, the administration starts at least 1 month before the primary surgery. In yet another embodiment, the administration starts within 1 week after the surgery.

In yet one embodiment, the at least one $CX_3CR1$ or fractalkine inhibitor comprises an antibody, siRNA, a ribozyme, an antisense, an aptamer, a peptidomimetic, a small molecule, or any combination thereof. In another embodiment, the antibody comprises an antibody selected from a polyclonal antibody, a monoclonal antibody, a humanized antibody, a synthetic antibody, a heavy chain antibody, a human antibody, and a biologically active fragment of an antibody.

In one embodiment, the small molecule is selected from the following:
(i) a compound of Formula (I),

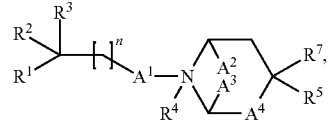

(I)

wherein in (I):
$A^1$ is $CH_2$ or cyclopentane-1,3-diyl;
n is 0, 1, 2, 3, 4 or 5 if A is $CH_2$, or n is 0, 1, or 2 if A is cyclopentane-1,3-diyl;
$A^2$ and $A^3$ are both H, or $A^2$ and $A^3$ combine to form a divalent radical selected from the group consisting of methanediyl, ethane-1,2-diyl, or propane-1,3-diyl;
$A^4$ is $CH_2$, $CH(CF_3)$, or $CF_2$;
$R^1$ is H, CN, $CO_2R_6$, $(C_1-C_6)CH_2NH_2$, or $(C_1-C_6)CH_2NHC(=O)NH(4\text{-piperidinyl})$;
$R^2$ and $R^3$ are independently aryl or substituted aryl; or $R^2$ and $R^3$ combine to form a divalent fragment (a), wherein X is selected from the group consisting of —S—, —O—, —$CH_2S$—, —$CH_2S(=O)$—, —$CH_2S(=O)_2$—, —$SCH_2$—, —$S(=O)CH_2$—, —$S(=O)_2CH_2$—, —$CH_2CH_2$—, —CH=CH—, —$CH_2O$—, —$OCH_2$—, —$N(CH_3)C(=O)$—, and —$C(=O)N(CH_3)$—;

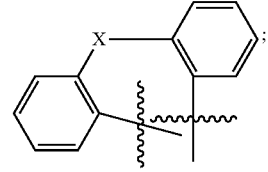

(a)

or $R^1$ and $R^2$ are both H, and $R^3$ is selected from the group consisting of:

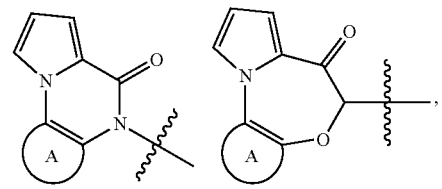

wherein ring A is selected from the group consisting of phenyl, substituted phenyl, pyridinyl, substituted pyridinyl, thiophenyl, substituted thiophenyl, 1H-pyrazole, and 1-($C_1$-$C_6$) alkyl-1H-pyrazole;
$R^4$ is nil or ($C_1$-$C_6$)alkyl, wherein if $R^4$ is ($C_1$-$C_6$)alkyl, compound of Formula (I) is a quaternary ammonium salt;
$R^5$ is ($C_1$-$C_6$)alkyl, substituted ($C_1$-$C_6$)alkyl, phenyl, substituted phenyl, heteroaryl, substituted heteroaryl;
$R^6$ is H, ($C_1$-$C_6$)alkyl, substituted ($C_1$-$C_6$)alkyl, aryl or substituted aryl; and,
$R^7$ is OH, $CH_2OH$, or $C(=O)OR^6$;

(ii) a compound of Formula (II):

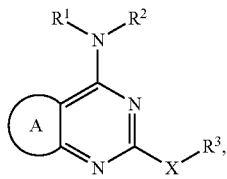
(II)

wherein:
A is a ring of formula (a), (b) or (c):

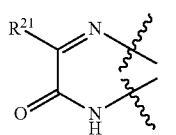
(a)

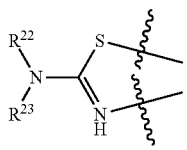
(b)

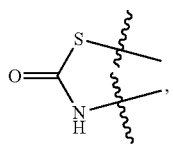
(c)

$R^1$ and $R^2$ independently represent H, $C_1$-$C_8$ alkyl, $C_2$-$C_8$ alkenyl, $C_2$-$C_8$ alkynyl or $C_3$-$C_7$ saturated or partially unsaturated cycloalkyl,
wherein in $R^1$ or $R^2$ the alkyl, alkenyl, alkynyl and cycloalkyl groups are optionally and independently further substituted with one or more substituents selected independently from the group consisting of OH, $C_1$-$C_6$ alkoxy, $CH_2OR^4$, $NR^5R^6$, $CO_2R^7$ and $CONR^8R^9$;
$R^3$ is $C_1$-$C_6$ alkyl, $C_2$-$C_6$ alkenyl, $C_2$-$C_6$ alkynyl or $C_3$-$C_7$ saturated or partially unsaturated cycloalkyl;
wherein in $R^3$:
the alkyl, alkenyl and alkynyl chains independently and optionally include a O, $NR^{10}$ or S atom in the chain;
the alkyl, alkenyl, alkynyl and cycloalkyl groups are independently and optionally further substituted by phenyl or a 5- or 6-membered heteroaromatic ring containing 1 to 3 heteroatoms selected independently from the group consisting of O, S and N;
the phenyl or heteroaromatic groups are independently and optionally further substituted with one or more substituents selected from the group consisting of halogen, $C_1$-$C_4$ alkyl, OH, $C_1$-$C_4$ alkoxy, CN, $CO_2R^{11}$, $NR^{12}R^{13}$, $C(=O)NR^{14}R^{15}$, $SO_2R^{16}$, $NR^{17}R^{18}$ and $SO_2N^{19}R^{20}$;
X is O, S or S(O);
$R^{21}$ is H, $CH_2OR^{24}$, $CH_2NR^{24}R^{25}$, $CO_2R^{24}$ or $C(=O)NR^{24}R^{25}$;
n is 0, 1 or 2;
$R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently H or $C_1$-$C_6$ alkyl;

(iii) a compound of Formula (VI):

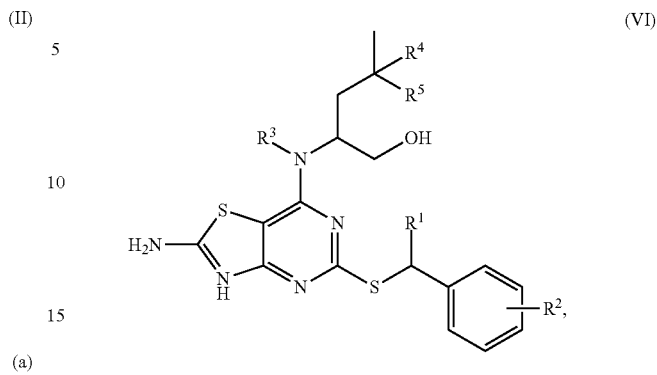
(VI)

wherein:
$R^1$ is $CH_3$ or $CH_3CH_2$;
$R^2$ is H, 2-F, 2-Cl, 3-F, 3-$OCH_3$, 3-CN, 3-$CF_3$, 3-$CONH_2$ or 3-$SO_2CH_3$;
$R^3$ is H or $CH_3$;
$R^4$ is H or $CH_3$ and
$R^5$ is H; or, when $R^4$ is $CH_3$, $R^5$ is H or F;
(iv) a compound of Formula (VII):

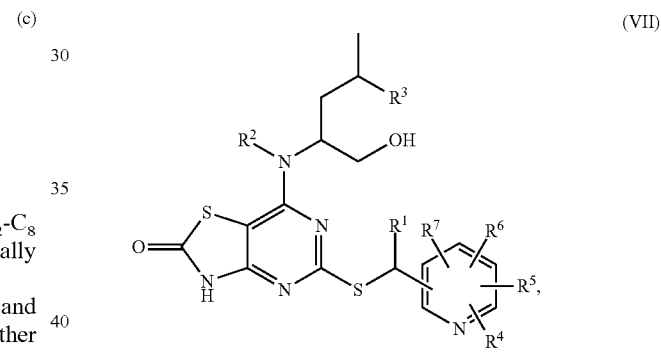
(VII)

wherein:
$R^1$ is $CH_3$ or $CH_3CH_2$;
$R^2$ is H or $CH_3$;
$R^3$ is H or $CH_3$;
$R^4$, $R^5$, $R^6$ and $R^7$ are independently H, $CH_3$ or $CH_2CH_3$;
(v) a compound of Formula (VIII):

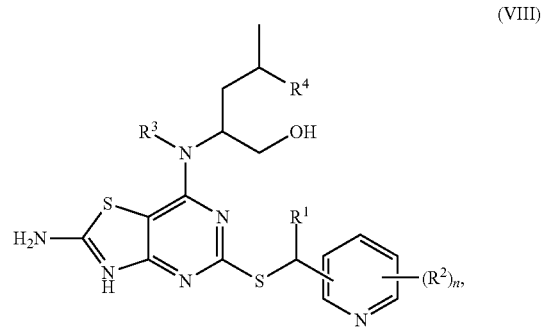
(VIII)

wherein:
$R^1$ is $CH_3$ or $CF_3$;
$R^2$ is halo, CN or $C_1$-$C_6$ alkyl;

$R^3$ and $R^4$ are independently H or $CH_3$;
n is 0, 1 or 2;
(vi) a compound of Formula (IX):
$$R^A\text{—}R^B \qquad (IX),$$
wherein:
$R^A$ is a group selected from the group consisting of:
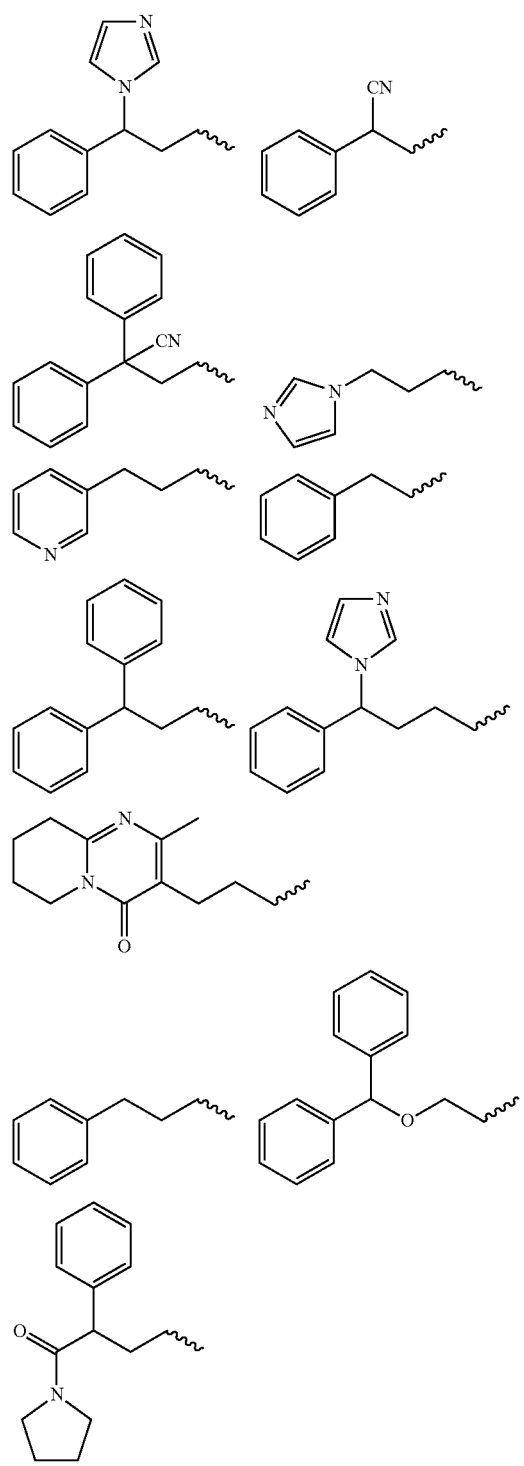
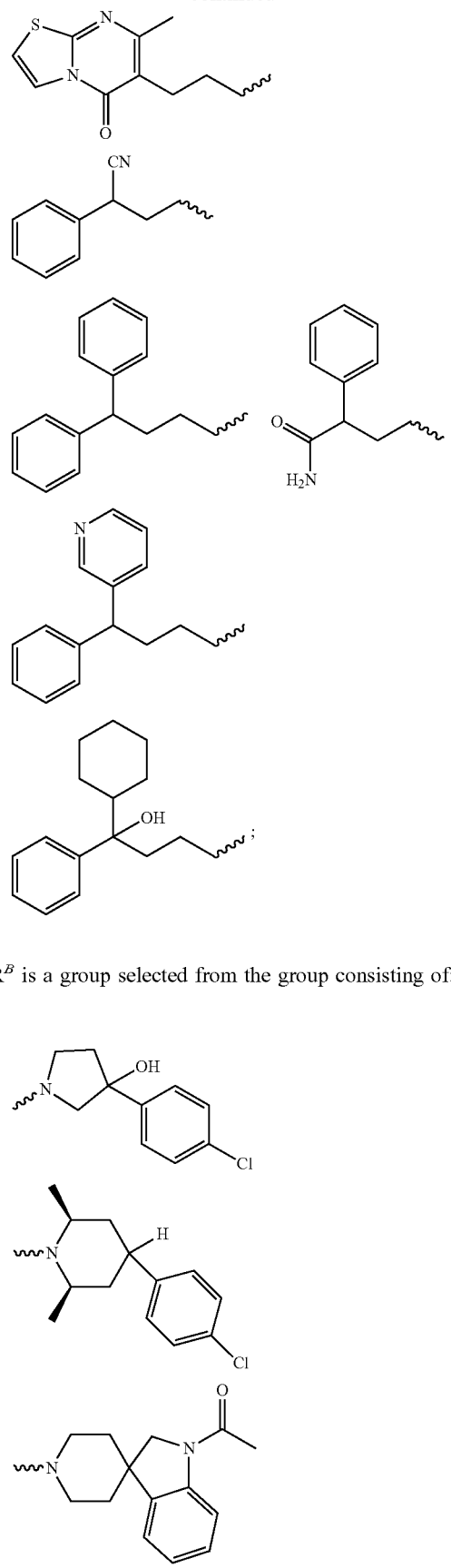
$R^B$ is a group selected from the group consisting of:
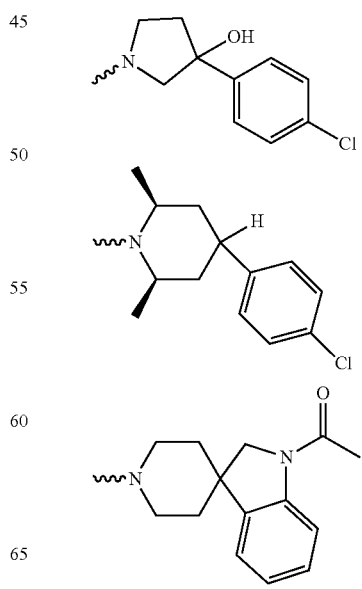

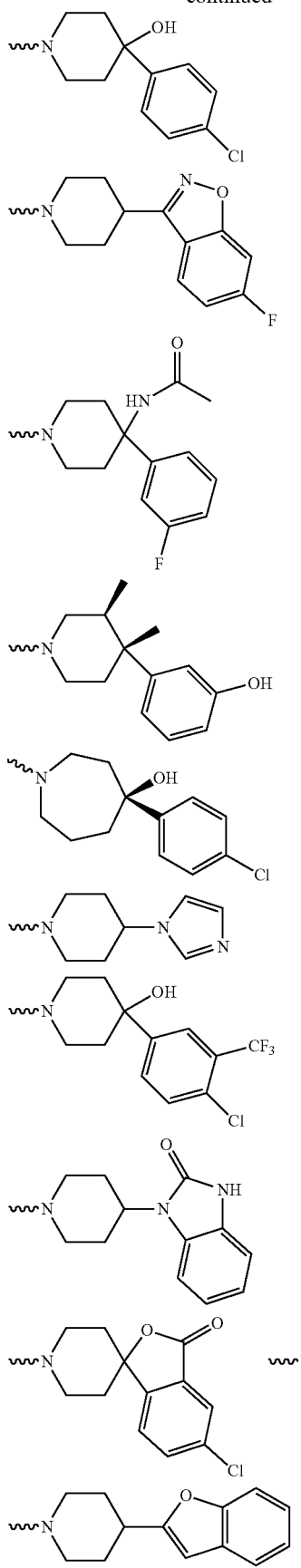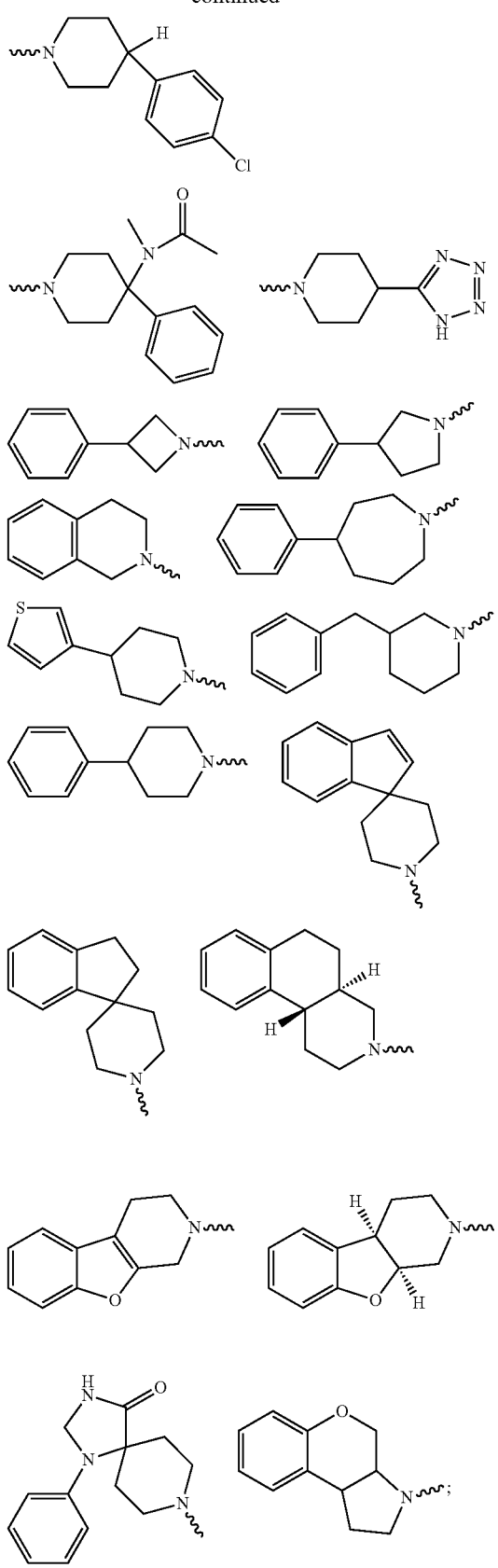

(vii) a compound of Formula (X):

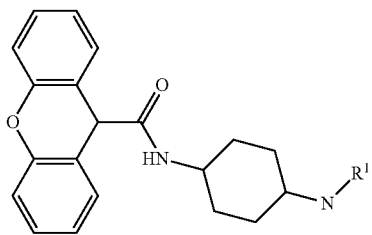

(X)

wherein R¹ is $(C_1-C_8)$ alkyl, substituted $(C_1-C_8)$ alkyl, phenyl, substituted phenyl, $(C_1-C_8)$ cycloalkyl or substituted $(C_1-C_8)$ cycloalkyl;

(viii) a compound of Formula (XI):

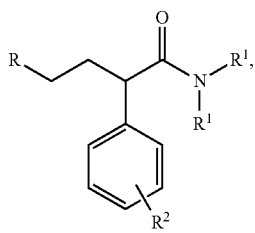

(XI)

wherein
R is selected from the group consisting of:

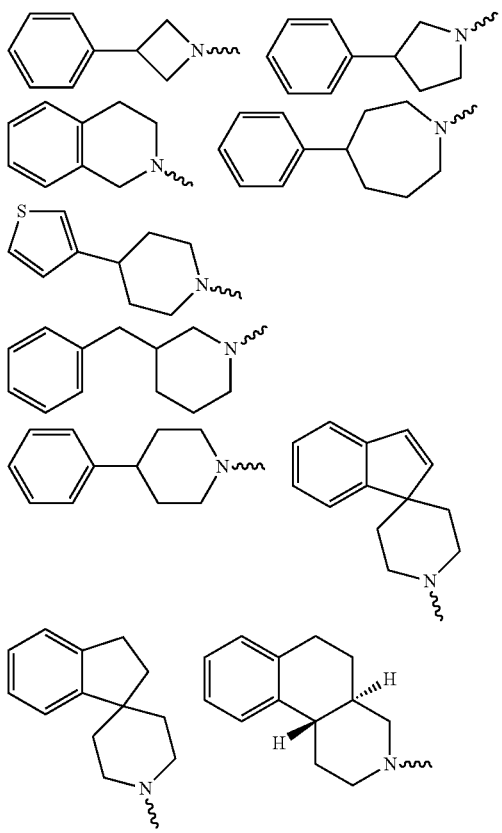

-continued

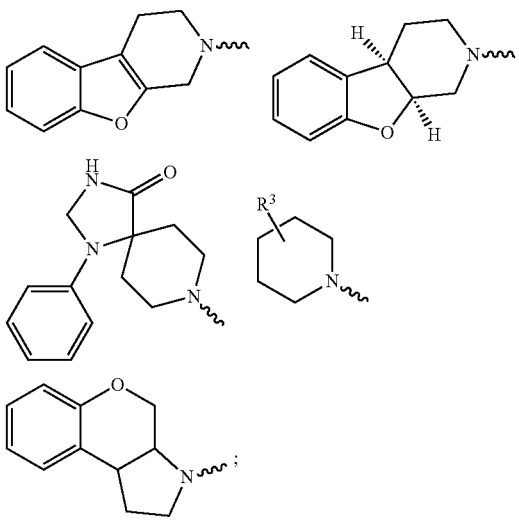

each occurrence of R¹ and R⁴ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, R² and R³ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, OR⁴, $N(R^4)(R^4)$, $NO_2$, or NHAc;

(ix) a compound of Formula (XII):

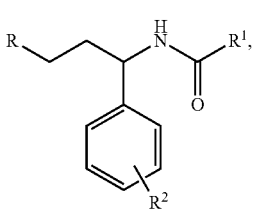

(XII)

wherein
R is selected from the group consisting of:

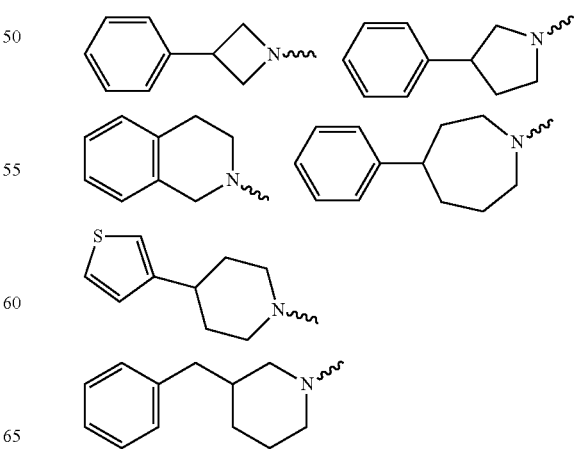

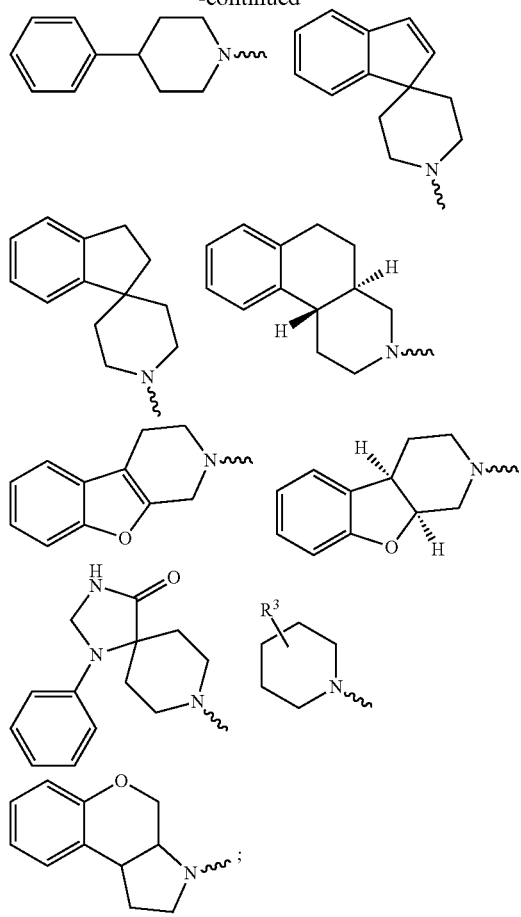

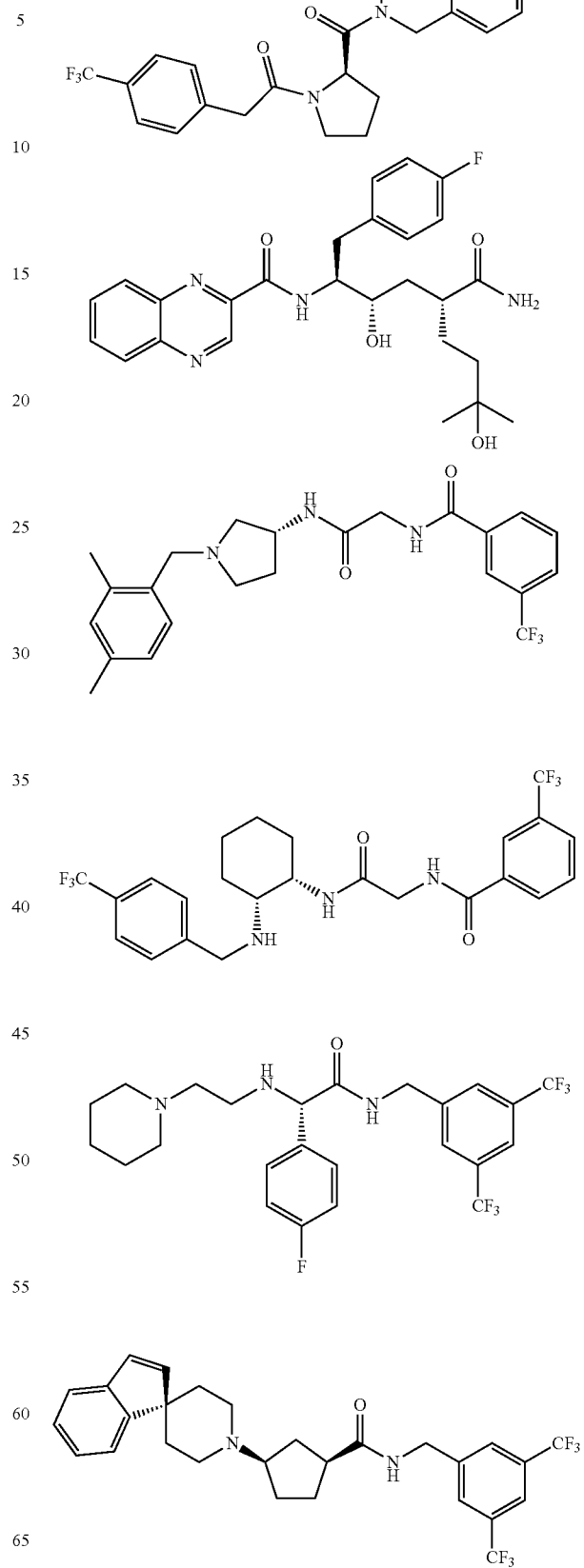

each occurrence of $R^1$ and R4 and $R^5$ is independently H, $(C_1-C_6)$ alkyl, substituted $(C_1-C_6)$ alkyl, phenyl, substituted phenyl, $(C_1-C_6)$ cycloalkyl, or substituted $(C_1-C_6)$ cycloalkyl; and, $R^2$ and $R^3$ are independently H, $(C_1-C_6)$ alkyl, substituted $(C_1-C_6)$ alkyl, phenyl, substituted phenyl, $(C_1-C_6)$ cycloalkyl, substituted $(C_1-C_6)$ cycloalkyl, halo, $OR^4$, $N(R^4)(R^4)$, $NO_2$, or NHAc;

(x) a compound selected from the group:

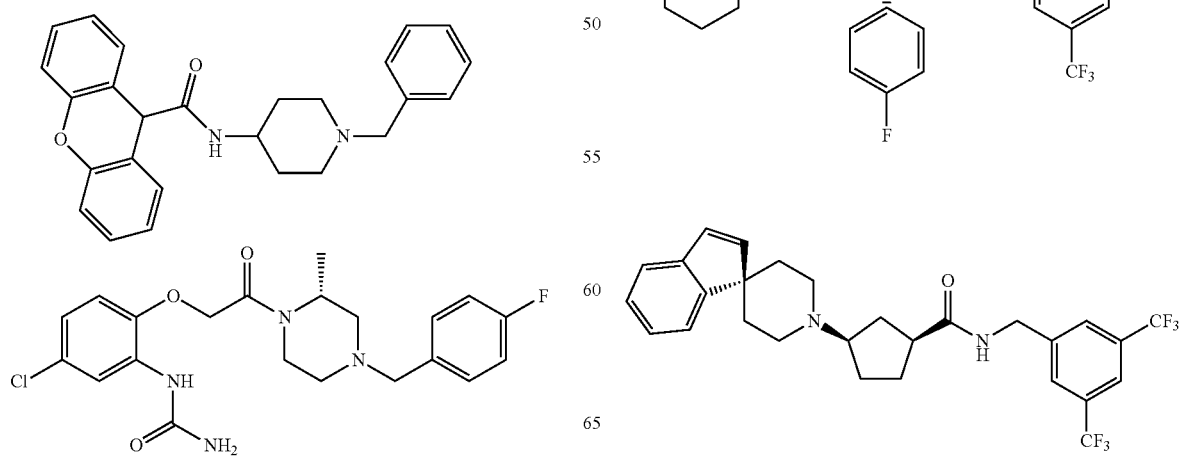

-continued

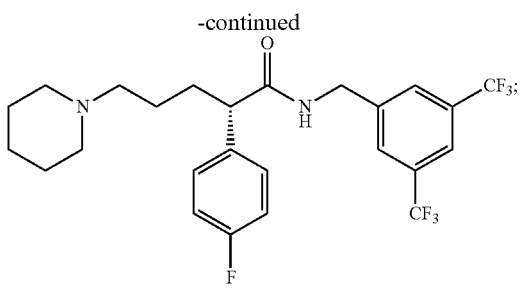

or a pharmaceutically acceptable salt thereof.

In one embodiment, in Formula (I) $R^2$ and $R^3$ are independently phenyl, substituted phenyl, naphthryl or substituted naphthryl.

In one embodiment, the compound of Formula (II) is:
(a) a compound of Formula (III):

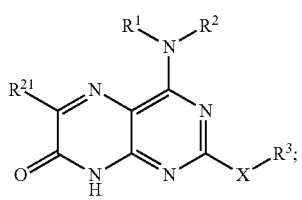

(b) a compound of Formula (IV):

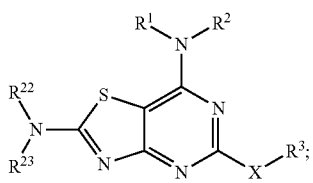

(c) a compound of Formula (V):

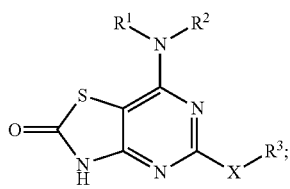

or a pharmaceutically acceptable salt thereof.

In one embodiment, in Formula (X) $R^1$ is n-hexyl, phenyl or cyclopentyl.

In one embodiment, the small molecule is 5-(4-(4-chlorophenyl)-4-hydroxypiperidin-1-yl)-2,2-diphenylpentanenitrile, N-(1-benzylpiperidin-4-yl)-9H-xanthene-9-carboxamide, or a pharmaceutically acceptable salt thereof.

In one embodiment, the subject is a mammal. In another embodiment, the mammal is human. In yet another embodiment, the composition is administered by an inhalational, oral, rectal, vaginal, parenteral, topical, transdermal, pulmonary, intranasal, buccal, ophthalmic, intrathecal, or intravenous route of administration.

Combination Therapies

The compounds identified using the methods described here are useful in the methods of the invention in combination with one or more additional compounds useful for treating cancer. These additional compounds may comprise compounds identified herein or compounds, e.g., commercially available compounds, known to treat, prevent, or reduce the symptoms of cancer and/or metastasis.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Formulations

The invention also encompasses the use of pharmaceutical compositions of at least one compound of the invention or a salt thereof to practice the methods of the invention.

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the patient either prior to or after the a surgical intervention related to cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of cancer in a patient.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing cancer in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials:

Unless otherwise noted, all starting materials and resins were obtained from commercial suppliers and used without purification.
ERK/Akt Assay Protocol On Day One, cells were split ($1.5 \times 10^4$ cells per well) in complete F12 media ($2.5 \times 10^5$ cells per mL) into black 96 well plates. Cells were incubated for 4-6 hours to attach. Fluid in plates was changed (SERUM FREE media ~100 µL per well) and plates were returned to 37° C. incubator overnight.

On Day Two, TBS, BSA, 0.25% TritonX100/TBS, and 4% formaldehyde/TBS were removed from the refrigerator, and allowed to warm to room temperature. Fluid in plates was changed ("SF" media-90 µL per well), and plate warmer was turned on to 37° C. Compounds were diluted: for a final starting concentration of 10 µM: 2 uL of 10 mM stock+200 uL of SF media. Solutions were well mixed and, using 96 well round bottomed plates, serially diluted across the plate: 20 µL of previous dilution+90 µL SF media. Compound was added to plate (10 µL per well), and incubated on plate warmer for 5 minutes. After 5 minutes, the media was removed and 50 µL per well of 4% formaldehyde/TB S were added. The system was incubated at room temperature on shaker for 10 minutes. The fixative was removed, and 50 µL per well 0.25% triton X 100/TB S were added. The system was incubated at room temperature on shaker for 15 minutes. PE assay buffer and 1×PE buffer were removed from refrigerator and allowed to warm to room temperature. Plates were washed 2× with 100-200 µL per well of 1×TBS, and blotted on paper towel. 2% BSA/TBS-20 mg/mL was made fresh for each day—500 mg BSA per 25 mL TBS. 50 µl 2% BSA/TBS were added per well, and system was incubated at room temperature on shaker for 45 minutes. Each well was washed 1× 100-200 uL TBS, followed by blotting. Primary Ab was prepared by dilutions in PE assay buffer: CST pERK 1/2; 1:400; and CST pAkt; 1:400. 50 µL primary Ab were added per well, and the system was incubated at room temperature for 1-1.5 h with shaking. The system was washed 4× with 150-200 µL per well with PE wash buffer, with blotting between washes. First wash was a quick rinse, and subsequent washes were 3-5 minutes each. Secondary Ab (PE DELFIA Eu-labeled anti rabbit) was prepared, using dilution as labeled. 100 µL of PE Enhancement solution was added per well, and cover plate was immediately covered with another black plate. The system was incubated for 5-15 minutes at room temperature on shaker, and plates were read on Packard Fusion.

A plate based phos-ERK and Akt assay may be developed using DELPHIA assay methodology. With standard fluorescent detection, reagent and microplate interference can contribute to high background and reduced sensitivity. DELFIA uses the principle of time-resolved fluorometry to remove background interference. Lanthanide chelates possess both long fluorescence decay times and large Stoke's shifts, properties that allow delayed signal measurement at a wavelength with little background interference. In addition, lanthanides emit a stable fluorescent signal that exhibits a sharp emission peak and high fluorescence intensity. The DELFIA assay principle is virtually identical to that of a standard sandwich ELISA. Analyte is first captured on a coated microplate, followed by addition of detection antibody to complete the sandwich. Unlike ELISA, DELFIA utilizes a lanthanide chelate-labeled detection antibody, which exhibits minimal fluorescence by itself. An enhancement step unique to DELFIA releases the lanthanide from the antibody complex, producing a new, highly fluorescent lanthanide chelate contained within a protective micelle. 4. The amplified fluorescent signal is detected using time-resolved fluorometry. This detection method removes non-specific interfering fluorescent background signal and provides DELFIA superior sensitivity it is known for.
Cell Lines and Cell Cultures.

MDA-MB-231 (MDA-231) and MDA-MB-436 (MDA-436) human breast cancer cells were purchased from ATCC (Manassas, Va.). The PC3-ML sub-line was derived from the parental PC-3 cells as previously described (Wang & Sterns, 1991, Differntiation 48:115-25). All cells were grown in DMEM containing 10% fetal bovine serum (Hyclone, Logan, Utah) and 0.1% gentamicin (Invitrogen, Carlsbad, Calif.) and kept at 37° C. and 5% $CO_2$. For the experiments performed in vivo, cells were engineered to stably express enhanced Green Fluorescent Protein (eGFP) using a lentiviral vector from America Pharma Source (Bethesda, Md.).
Transfection and Selection of Stable Cell Lines.

The cDNAs for wild type and mutant $CX_3CR1$ isoforms were inserted in the pEGFP-N1 vector (Clontech, Inc., Mountain View, Calif.). MDA-436 were transfected with 3 µg of plasmid DNA using the Lipofectamine 2000 transfection system according to manufacturer's instructions (Invitrogen). Stable transfected cells were selected using geneticin (Invitrogen).

Immunohistochemistry and Tissue Array Analysis.

Breast tissue microarrays (BRC1502, BR1002) were obtained from US Biomax (Rockville, Md.) and the staining for $CX_3CR1$ was performed as described previously (Jamieson et al., 2008, Cancer Res. 68:1715-22), with an antibody against CX3CR1 (7201) obtained from Abcam (Cambridge, Mass.) and used at a 3.3 µg/ml concentration. In total, 106 tissue cores of breast cancer and 36 tissue cores of normal breast were examined.

Animal Models of Metastasis.

Five week-old female CB17-SCID, C57Bl/6 and Balb/c mice were obtained from Taconic (Germantown, N.Y.) and housed in a germ-free barrier. C57Bl/6-FKN−/− transgenic mice were obtained from Schering-Plough (now Merck-Schering Plough, Whitehouse Station, N.J.) and bred in house. Balb/c and CB17-SCID mice were used for the detection of bone-disseminated breast cancer cells at 24 and 72 hours post-inoculation, respectively. C57Bl/6 mice were used as same-strain controls for the C57Bl/6-FKN−/− transgenic mice to detect cancer cells disseminated to the skeleton at 24 hours post-inoculation. At 6-8 weeks of age, mice were anesthetized with ketamine (80 mg/kg) and xylazine (10 mg/kg) and inoculated in the left cardiac ventricle with human cancer cells ($5 \times 10^5$ for MDA-436 and PC3-ML cells and $1 \times 10^5$ for MDA-231 cells in a total volume of 100 ml of DMEM/F12). Blue-fluorescent polystyrene beads (10 µm diameter, Invitrogen-Molecular Probes) were co-injected to confirm successful delivery in the blood circulation. All experiments were performed in accordance with NIH guidelines for the humane use of animals. All protocols involving the use of animals were approved by the Drexel University College of Medicine Committee for the Use and Care of Animals.

Tissue Preparation and Cancer Cell Detection.

Animals were sacrificed and tissues were fixed, decalcified in 0.5M EDTA if necessary and frozen in O.C.T. embedding medium (Electron Microscopy Sciences, Hatfield, Pa.) as previously described (Russell et al., 2009, Oncogene 28:412-21). Serial tissue sections of 80 µm in thickness were obtained using a Microm HM550 cryostat (Mikron, San Marcos, Ca.). Sections of each hind leg and soft-tissue organs were transferred on glass slides, stored at −20° C. and examined for cancer cells using either an Olympus IX70 fluorescence inverted microscope or an Olympus SZX12 fluorescence stereomicroscope. Bright field and fluorescence images were acquired with an Olympus DT70 CCD color camera.

Detection of Soluble FKN in Murine Bone Marrow.

Bone marrow was flushed from the hind legs of wild type C57Bl/6 mice or FKN-null mice. The cellular component was removed by centrifugation at 2000 r.p.m. for 10 minutes at 4° C. Soluble FKN was detected using an ELISA DuoSet kit for murine FKN (R&D Systems) as previously described (Jamieson et al., 2008, Cancer Res. 68:1715-22).

In Vitro Experimental Protocol.

Cells were serum starved for 4 hours and then exposed to 50 nM recombinant human FKN (R&D systems, Minneapolis, Minn.) for indicated time points.

SDS-PAGE and Western Blotting.

Cell lysates were obtained and SDS-polyacrylamide gel electrophoresis and western blot analysis were performed as previously described (Shulby et al., 2004, Cancer Res. 64:4393-98), with few modifications. Membranes were probed with an antibody against $CX_3CR1$ (0.5 µg/ml, Torrey Pines Biolabs, East Orange, N.J.) and actin (Sigma, St. Louis, Mo.) using 5% milk as a blocking reagent. Membranes were also probed with antibodies targeting phospho-p44/42 MAPK (Thr202/Tyr204, Cell Signaling) and total p44/42 MAPK (Cell Signaling). All primary antibody incubations were performed overnight at 4° C. Primary antibody binding was detected using horseradish peroxidase-conjugated anti-rabbit secondary antibody (Pierce, Rockford, Ill.). Chemiluminescent signals were obtained using SuperSignal West Femto reagents (Pierce) and detected with the Fluorochem 8900 imaging system and relative software (Alpha Innotech, San Leandro, Calif.).

Immunofluorescence and Confocal Microscopy.

Cells were grown on 15 mm glass coverslips and fixed with 4% formaldehyde at 4° C., not permeabilized and incubated with an antibody against $CX_3CR1$ (Torrey Pines Biolabs) in blocker for 30 minutes and at room temperature. A CY3-conjugated secondary antibody (Jackson Immunoresearch, West grove, Pa.) was used to detect the primary antibody and incubated for 30 minutes at room temperature. Nuclear staining was obtained with Hoechst 33343. Samples were imaged using a LSMS exciter confocal system (Carl Zeiss, Usa) connected to a Axio Imager.Z1m microscope mounting a Plan Apochromat 20× objective with a 0.8 numerical aperture. Images were collected using a step size of 2 µm along the z axis using the version 4.2 of the dedicated software.

$CX_3CR1$ Signaling in Vitro.

Cells were serum starved for 4 hours and then exposed to 50 nM recombinant human FKN (R&D systems, Minneapolis, Minn.) for indicated time points.

Cell Surface $CX_3CR1$ Protein Isolation.

The amount of either wild-type or functional mutant forms of $CX_3CR1$ that were expressed by MDA-436 breast cancer cells at the plasma membrane level were measured by cell surface biotinylation, using a dedicated kit (cat. #89881) obtained from Pierce (Rockford, Ill.), according to the protocol provided by the manufacturer.

Statistics.

Statistical significance for the in vivo studies was determined using a one-tailed Student's T-test using GraphPad Prism version 3.0 for Windows (GraphPad Software, San Diego, Calif.) and data are presented as mean±standard error of the mean (S.E.M.).

Example 1: Involvement of $CX_3CR1$ Receptor in Cancer Metastasis

Skeletal metastases from breast adenocarcinoma are responsible for most of the morbidity and mortality associated with this tumor and represent a significant and unsolved problem for therapy. The arrival of circulating cancer cells to the skeleton depends first on the adhesive interactions with the endothelial cells lining the bone marrow sinusoids, and then the extravasation toward chemoattractant molecules produced by the surrounding bone stroma.

The studies described herein provide compelling evidence for the adhesive and chemotactic interactions between the $CX_3CR1$ receptor expressed by breast cancer cells and fractalkine in the bone tissue. $CX_3CR1$ protein was detected in tissue microarrays of normal and malignant mammary glands. Using a pre-clinical animal model of hematogenous metastasis breast cancer cells expressing high levels of this receptor were shown to have higher propensity to disseminate to the skeleton. Furthermore, studies with fractalkine-null transgenic mice demonstrated that the ablation of the adhesive and chemotactic ligand of $CX_3CR1$ dramatically impairs the skeletal dissemination of breast cancer cells. Finally, cells that were engineered to express exogenous wild type or functional mutants of $CX_3CR1$ were employed to conclusively confirm the determinant role of this receptor in the arrest of breast cancer cells to the skeleton.

Figure 4:
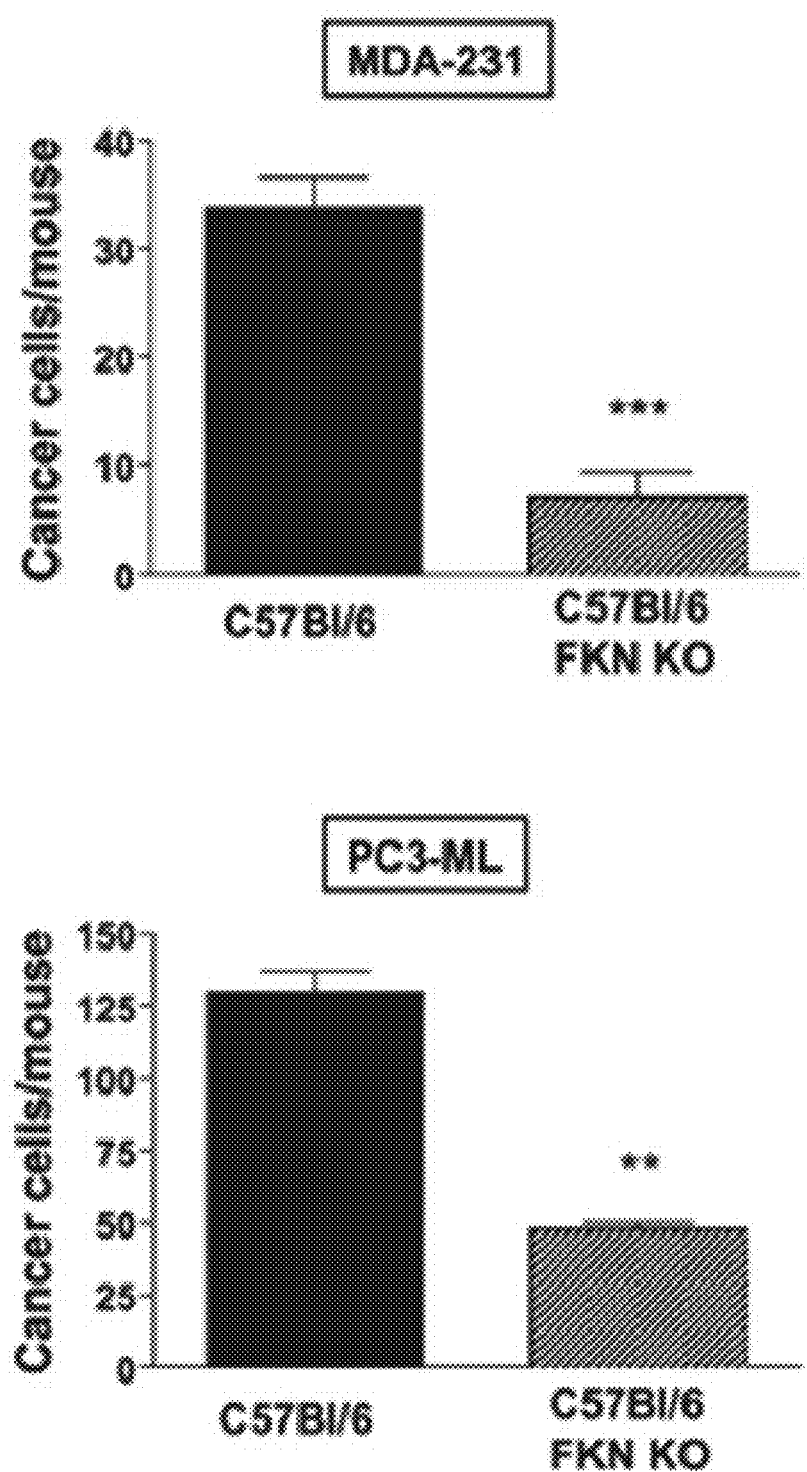
FIG. 4 is a graph summarizing data illustrating that both breast and prostate cancer cells are impaired in their arrival to the bone of mice null for FKN. Between 3 and 5 mice per group were used. The number of tumor cells detected is shown as mean±SEM. (p=0.0002, *p=0.0001).

Direct interference with $CX_3CR1$-FKN functional interactions was studied. To this end, the impact exerted by the absence of FKN on cancer cell arrival to the bone was studied by using a transgenic mouse model null for the chemokine. When these mice received MDA-231 cells in the blood circulation the inspection of targeted bones showed a dramatic reduction in the number of disseminated cancer cells, which were decreased by 60-70% as compared to FKN-expressing animals. To further establish the role of $CX_3CR1$ in this process, similar experiments were conducted using PC3-ML prostate cancer cells, which had previously been shown to express high levels of this chemokine receptor and are highly bone metastatic (Russell et al., 2009, Oncogene 28:412). As seen for MDA-231 cells, also PC3-ML cells were significantly impaired in their arrival to bone when inoculated in FKN-null mice (FIG. 4).

It should be emphasized that, although the involvement of other chemokine receptors in the dissemination of breast cancer cells has been proposed, transgenic models null for the chemokine ligands have never been used to date. In particular, the role of CXCR4 could not be investigated in this fashion, as mice knockout for its chemokine ligand CXCL12-SDF-1 display a lethal phenotype.

Thus, these studies represent the first pre-clinical investigation to conclusively establish the role of a chemokine receptor in the metastatic abilities of cancer cells by genetically removing the partnering chemokine.

Taken together, these observations suggest that blocking $CX_3CR1$-FKN interactions by selective and potent pharmacological compounds could replicate the results provided by genetic manipulation of FKN expression in animal models and effectively interfere with the skeletal dissemination of breast cancer cells. These antagonists would be the first available to be tested using a preventative strategy in clinical trials conducted with breast cancer patients at risk for metastatic dissemination.

Despite the relevant number of studies devoted to the characterization of $CX_3CR1$ signaling and the understanding of its functional role in immunology and rheumatology processes among others, pharmacological tools to impair its activation and signaling have been lacking.

Figure 5:
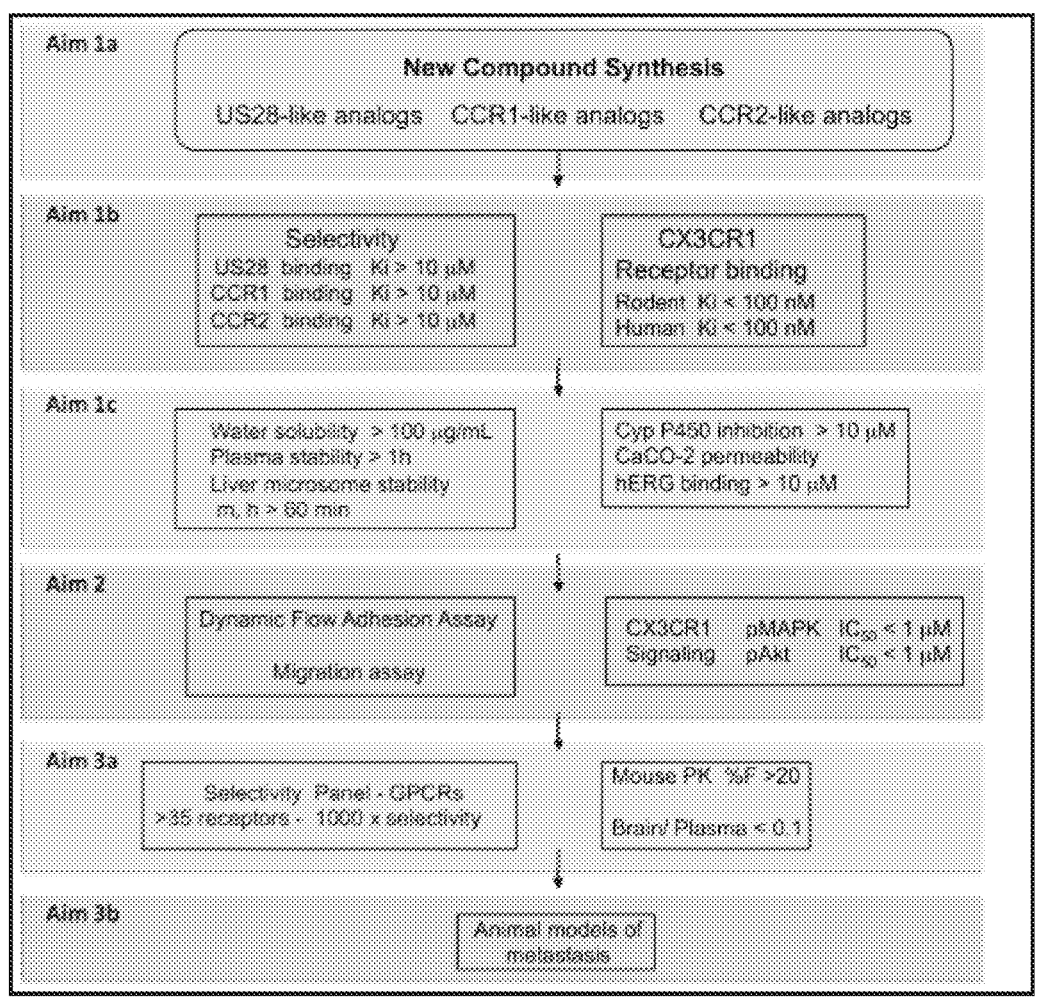
FIG. 5 is a fluxogram illustrating the multiple stages of the planned research.

In one aspect, the present invention includes the identification of novel non-peptide, small molecule antagonists of the chemokine receptor $CX_3CR1$, which inhibit or reduce the arrival of circulating cancer cells to different organs, particularly the skeleton. The strategy is illustrated in FIG. 5.

Example 2: Synthesis of Novel Antagonists of $CX_3CR1$

Using non-selective chemokine antagonists which bind to chemokine receptors homologous to $CX_3CR1$ as starting points, analogs from three distinct chemical series are synthesized and optimized using medicinal chemistry to generate novel and specific $CX_3CR1$ antagonists.

Chemokine receptors belong to class A G protein-coupled receptors (GPCR) super family (gerard & Rollins, 2001, Nat. Immunol. 2:108). Structure activity relationships and mutagenesis studies suggest the presence of a generic binding pocket inside the seven transmembrane bundles (Allen et al., 2007, Annu. Rev. Immunol. 25:787).

Identification of a non-peptide small molecule antagonist for $CX_3CR1$ is based on a pharmacophore approach where privileged structure motifs and non-selective ligands of homologous receptors are screened for binding and inhibition of functional activity. The molecular interaction of the chemokine FKN and its receptor $CX_3CR1$ has been extensively studied through mutagenesis. A cluster of basic residues and one aromatic residue define the key hotspots important for receptor interaction (Mizoue et al., 2001, J. Biol. Chem. 276:33906).

Basic residues near the N-terminus suggest binding to an acidic residue on the receptor, presumably the conserved glutamic acid (Glu) residue in TM7 common to chemokine receptors (Rosenkilde & Schwartz, 2006, Curr. Top. Med. Chem. 6:1319). The requirement for a phenylalanine residue (Phe) suggests an engagement with an aromatic pocket in the receptor. Membrane bound FKN binds the 7-transmembrane human cytomegalovirus receptor US28 with nanomolar affinity. US28 not only interacts with FKN but also binds CC chemokines such as MCP-1 (CCL2) with nanomolar affinity (Kledal et al., 1998, FEBS Lett. 441:209).

Interestingly, non-peptide small molecule ligands are known for CCR2 and US28, which possess common pharmacophoric features such as a basic amine and an aromatic moiety, both important for receptor affinity. Based on this evidence two initial compounds were synthesized.

Figure 6:
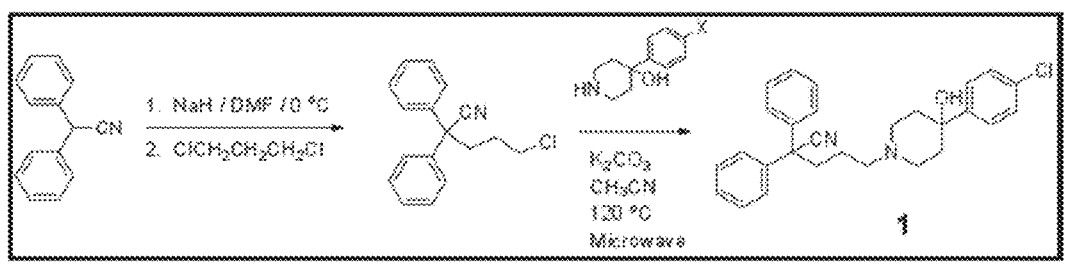
FIG. 6 is a synthetic scheme illustrating the synthesis of Compound 1 (5-(4-(4-chlorophenyl)-4-hydroxypiperidin-1-yl)-2,2-diphenylpentanenitrile).
Figure 7:
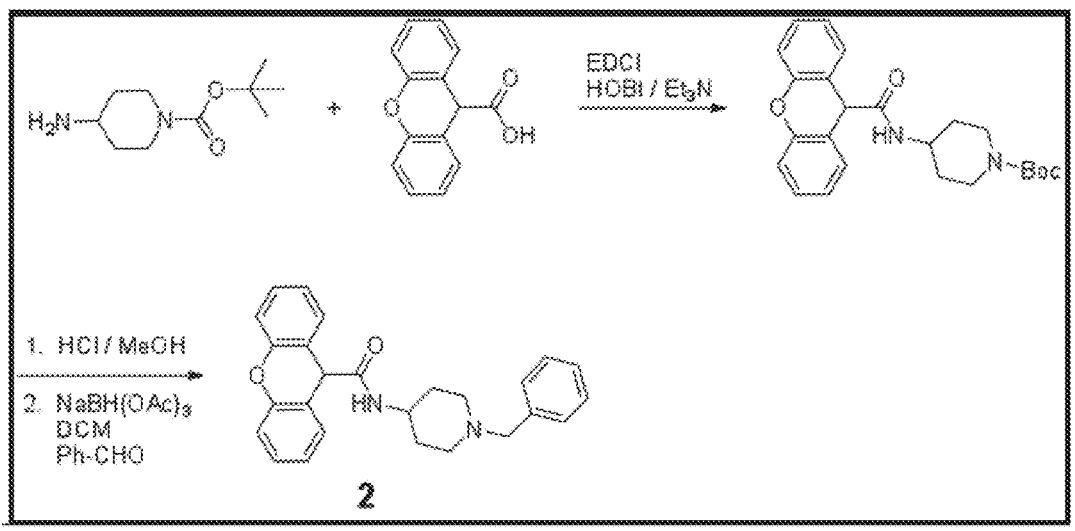
FIG. 7 is a synthetic scheme illustrating the synthesis of Compound 2 (N-(1-benzylpiperidin-4-yl)-9H-xanthene-9-carboxamide).

Compound 1, previously reported to be an inverse agonist of US28, was synthesized according to FIG. 6. As compound 1 was also reported to function as an antagonist of CCR1 compound 2, a well-know CCR1 antagonist, was synthesized according to FIG. 7.

Figure 8:
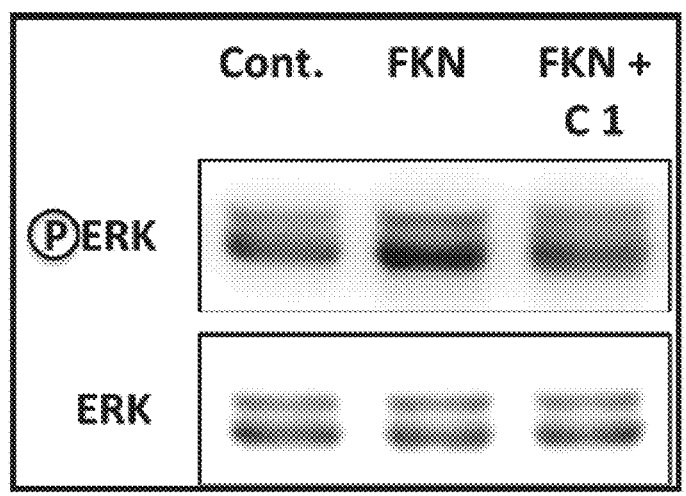
FIG. 8 is a set of pictures of electrophoretic gels, illustrating the finding that Compound 1 used at 10 µM inhibits ERK phosphorylation induced by exposure of MDA-436 breast cancer cells over-expressing $CX_3CR1$ to 50 nM FKN for 5 minutes.

Compound 1 was then evaluated for its ability to inhibit the activation of downstream intracellular pathways by $CX_3CR1$ upon stimulation with soluble FKN. In these experiments, MDA-MB 436 human breast cancer cells, engineered to over-express $CX_3CR1$, were treated with 50 nM FKN for 5 minutes after being incubated with compound 1 for 30 minutes. FIG. 8 illustrates that compound 1 was able to inhibit the activation of the MAPK pathway by blocking phosphorylation of ERKs induced by FKN.

Compound 1 represents the first small molecule $CX_3CR1$ antagonist, albeit weakly potent, found based on a rational pharmacophore based approach which holds promise for the discovery of other new leads for optimization into a specific $CX_3CR1$ antagonist.

The non-peptide US28 inverse agonist, 1, and the CCR1 antagonist, 2, provide starting points as $CX_3CR1$ antagonists. Various analogs of Compounds 1 and 2 are synthesized and evaluated for affinity, selectivity, and functional efficacy. The resulting structure activity relationships will guide improvement of potency and drug-like properties and selectivity. Chemical synthesis provides three distinct chemical series for lead optimization, based on CCR1, US28, and CCR2 antagonists or inverse agonists. The key basic amine common to most small molecule chemokine antagonists and shown to be critical in FKN affinity to $CX_3CR1$ is retained. An aromatic motif shown to be critical in FKN and a common feature in small molecule chemokine antagonists is also be incorporated into the design. Construction of new analogs is based on a modular approach allowing a mix and match strategy of a right hand aryl piperidine core containing a basic amine, the central core consisting of an alkyl, cycloalkyl, or an amide bond linker, and the left hand aromatic motif typically substituted with a halogen or trifluoromethyl group.

Figure 9:
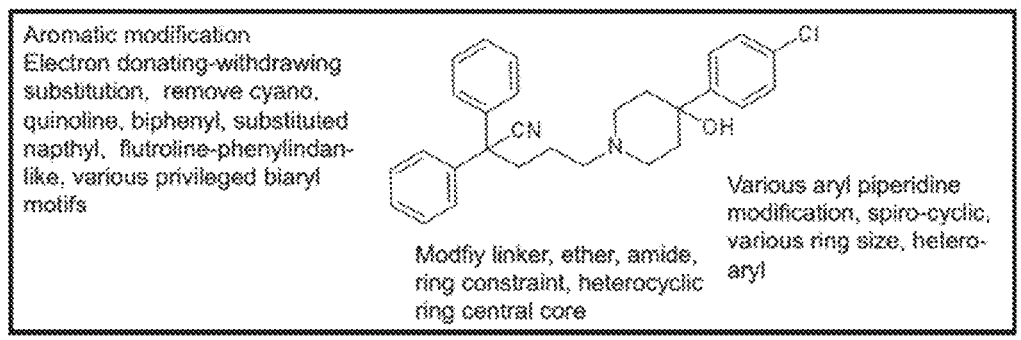
FIG. 9 is a scheme illustrating various types of modification planned for Compound 1, a US28/CCR1 antagonist with inhibitory activity on $CX_3CR1$.

There are numerous examples of small molecule CCR1 receptor antagonists in the literature, which also bear the common pharmacophoric features of an aromatic moiety and a basic amine. The US28 inverse agonist compound 1 demonstrated weak CX$_3$CR1 antagonism and thus is the focus of further optimization following the general strategy highlighted in FIG. 9.

A series of analogs includes various changes to the left hand side of the molecule such as substitution to the aromatic ring, linker modifications to explore chain length and conformational constraints to the central core, and aromatic substitution and ring size modifications to the aryl piperidine ring on the right hand side on the molecule.

Figure 10:
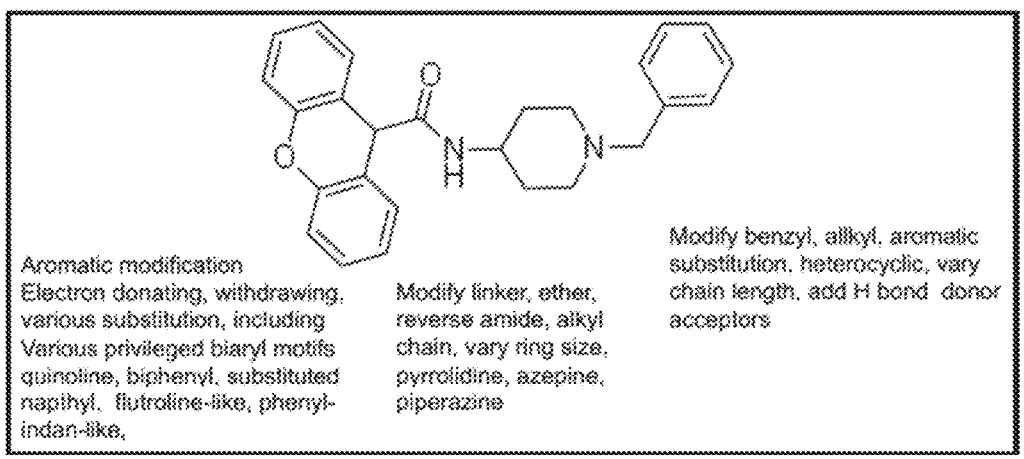
FIG. 10 is a scheme illustrating various types of modification planned for Compound 2, a CCR1 antagonist.

FIG. 10 highlights the strategy to modify the compound 2. Analogs include compounds where the 9-xanthenyl aromatic motif is modified with electron donating, electron withdrawing, H-bond donors and acceptors, and replacement with phenylindan-like and flutroline-like priviledged biaryl structures found in known drugs and GPCR ligands. The central core is modified by varying the amide linker with reverse amide and ether replacements, and the ring size of the central piperidine ring is varied to give five, six and seven member rings.

The benzyl group is modified to examine the optimum alkyl tether length, aromatic substitution, and heterocyclic replacements for the phenyl ring. These analogs are synthesized using standard robust chemistry methods and where appropriate efficient parallel synthesis methods. This modular approach facilitates the ability to mix and match various optimized motifs across different chemical series in an efficient manner to quickly optimize for potency and selectivity.

Figure 11:
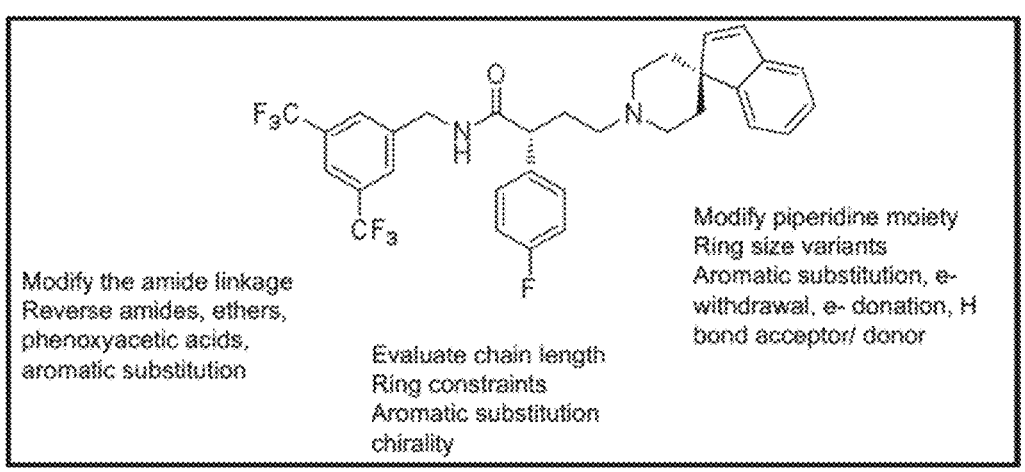
FIG. 11 is a scheme illustrating the contemplated modification of (S)—N-(3,5-bis(trifluoromethyl)benzyl)-2-(4-fluorophenyl)-4-(spiro[indene-1,4'-piperidin]-1'-yl)butanamide for compound 1, a CCR2 receptor antagonist.

A third chemical series is also examined, adopting a strategy modifying a CCR2 antagonist (FIG. 11). Various analogs are made to explore the effect of ring size of the right-hand piperidine ring, aromatic substitution with electron withdrawing and donating groups, H-bond donating and acceptor modification on affinity and functional activity. Central core analogs are made to evaluate the tether chain length, introduce ring conformation constraints, and vary the substitution of the aromatic moiety. Variations of the right hand side are made to probe the amide linkage, and evaluate various changes to the aromatic ring. A concise informative set of analogs are synthesized around this CCR2 antagonist in order to discover a novel lead series. The current information available in the literature indicates that small molecule non-peptide chemokine antagonists tend to be non-specific, and specificity is built in through lead optimization. The exploration of multiple chemical series, the first already demonstrating weak activity, provides an excellent chance to discover several chemical lead series. Lead optimization then provide potent, specific, and drug-like CX$_3$CR1 antagonists based on strong literature precedent from programs focused on optimizing chemokines such as CCR2 or CCR1.

Example 3: Binding Assays

The compounds synthesized for each chemical series, according to the different strategies described above, are first screened for their binding affinity to CX$_3$CR1 before being optimized to identify lead series.

MDA-436 have been recently reported to express very low levels of CX$_3$CR1. MDA-436 cells engineered to exogenously express CX$_3$CR1 and SKBR3 cells, which endogenously express the receptor, will be used. Cells are plated in 96-well plates, which will be mounted on a Multiscreen HTS vacuum manifold apparatus (Millipore). Radioactive FKN ($^{125}$I-FKN, 25 µCi, 925 kBq, Perkin Elmer) is used at a concentration of 50 pM and each newly synthesized compound is tested at five different concentrations starting from $10^{-10}$M and up to $10^{-6}$M, in quadruplicate. The nonradioactive form of the chemokine is also included in each assay at the same concentrations used for the compounds to be evaluated. Non-specific binding is considered as the binding determined in the presence of 0.1 µM of unlabelled FKN. Each competition-binding assay is conducted at 4° C. for 3 hours. IC$^{50}$ values is determined by non-linear regression and K$_D$ and Bmax values are calculated using the equations $$K_D=IC_{50}-L \text{ and } =B_0(1+(K_D/L)).$$

The compounds that display affinity for CX$_3$CR1 with a K$_i$<100 nM are then tested for their selectivity over the CCR1, CCR2 and US28 in binding experiments including COS-7 cells engineered to exogenously overexpress each receptor as previously reported (Liang et al., 2000, J. Biol. Chem. 275:19000). Compounds with a K$_i$>10 µM for each receptor type will be moved to the next phase Optimization studies provide structure activity relationships for the three distinct chemical series to generate a potent and selective lead series with good drug-like properties. Evaluation of physico-chemical properties of lead-compounds, such as water solubility and lipophilicity, is performed. Thus, the increase in hydrogen bonds and addition of non-polar groups is considered while avoiding to exceed the parameters dictated by the Lipinsky rules.

The next step is the identification of compounds with favorable ADME properties (Absorption, Distribution, Metabolism and Excretion) and toxicity profiles, with the ultimate goal of ruling out unsuitable drug candidates. As a pharmacophore approach starting from non-specific chemokine receptor antagonists is used, ADME properties for some of these compounds have been already established or can be easily extrapolated. Thus, if compared to high-throughput screenings of different libraries, the approach described herein significantly facilitates optimization in order to move from lead-likeness to drug-likeness (FIG. 5).

(a) Solubility

The compounds' solubility are evaluated for its dissolution in water compared against a soluble solvent using LC-UV or LC-MS/MS analysis. There are several methods to determine water solubility at the lower concentration ranges, but if required an exact solubility limit of a test compound is determined using a more laborious HPLC or LC/MS/MS method with a saturating amount of solid test compound.

(b) Plasma and Microsomal Stability

Representative analogs are evaluated for their stability in the presence of liver microsomes by incubating the test compound for 30 minutes with a microsome concentration of 0.5 mg/ml and using NADPH as cofactor. This analysis provides critical information required to optimize bioavailability and understand the potential for hepatotoxicity of a test compound, which will be tested by measuring the inhibition of Cytochrome P450. Intrinsic clearance (Cl$_{int}$), a critical property for optimization in human and the preclinical species of the animal models, is determined based on the first order elimination constant by non-linear regression for four species; mouse, rat, dog, and human. Test compound stability in rat, dog, monkey, and human plasma is also determined by LC-MS/MS analysis.

(c) Permeability

This assay is the gold standard for evaluating the potential for oral dosing of a drug candidate. Caco-2 human colon cells are used as a polarized monolayer grown on a solid-support filter. The compound to be tested is added to one side of the monolayer and the concentration of the compound detected on the other side will be measured by using LC-MS/MS analysis and used as an indication of its permeability.

(d) hERG

This assay evaluates the potential cardiac toxicity of drug candidates, which is compared to know blockers of cardiac ion channels (Cisapride or Terfenadine for hERG channel) and screened by patch clamp performed using human cardiomyocytes.

Example 4: Inhibitory Activity of Compounds on $CX_3CR1$-Dependent Adhesion, Migration and Signaling of Human Breast Cancer Cells In Vitro Compounds with good drug-like properties are tested for their ability to interfere with the functional activities of $CX_3CR1$. First, compounds that, in addition to potently binding $CX_3CR1$, can also disrupt its adhesive interaction with FKN, are identified. This process occurs rapidly through the establishment of a strong and stable bond with the membrane-bound form of the chemokine. The adhesion mediated by $CX_3CR1$ does not require G-protein activation and downstream signaling; however the promotion of cell migration is dependent on the ability to transduce intracellular signals. Thus, the chemotaxis of $CX_3CR1$ expressing cancer cells towards a concentration gradient of soluble FKN is evaluated in the presence of the newly synthesized compounds. Finally, the activation of two downstream signaling pathways such as PI3K/Akt and MAPK is directly evaluated by using $CX_3CR1$-expressing cancer cells exposed to soluble FKN, with or without the selected drug-candidates.

(a) Adhesion

Figure 12:
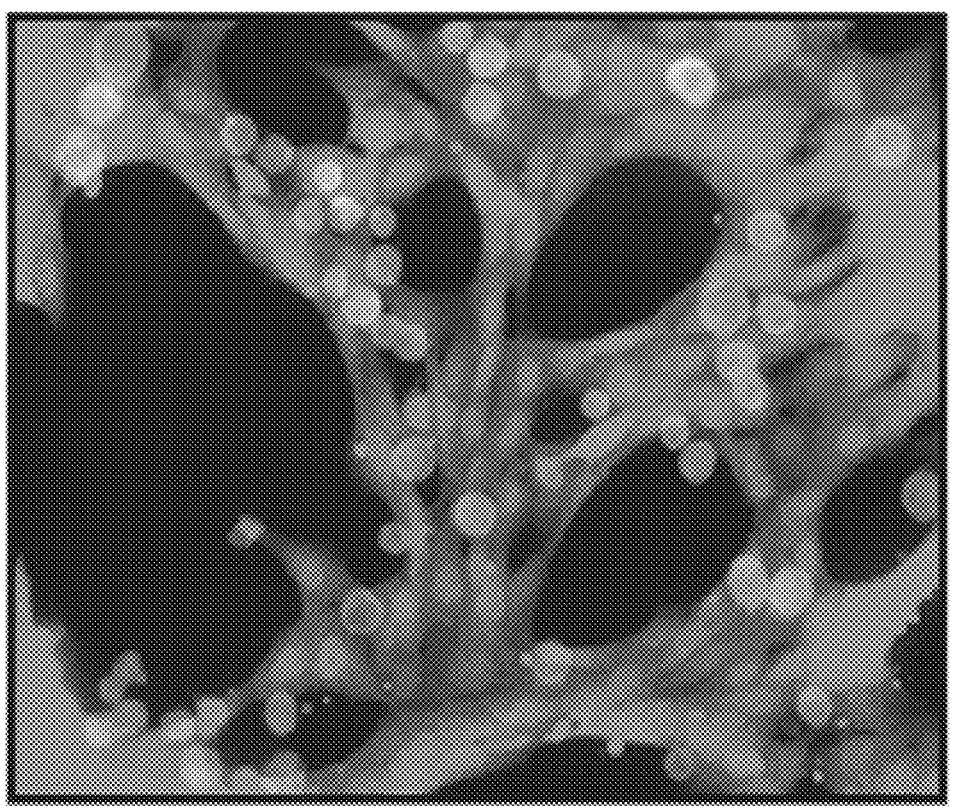
FIG. 12 illustrates the finding that red-fluorescent cancer cells firmly adhered to green-fluorescent HBMEs after being perfused at a flow rate corresponding to 10 dyne/cm².

These experiments are conducted in dynamic-flow conditions, generating shear forces that reproduce those recorded in the bone marrow sinusoids. Thus, Human Bone Marrow Endothelial cells (HBMEs) are loaded with a green fluorescent probe (CellTracker, Invitrogen) and plated on 24×50 mm glass coverslips coated with collagen and fibronectin and grown as monolayers (FIG. 12).

Coverslips are mounted in a parallel-plate flow chamber (RC-27N, Warner). A flow adhesion saline buffer (320 mOsm) containing 1% bovine serum albumine ise used to incubate the cell monolayers for 10 minutes. MDA-231 breast cancer cells in suspension ($2\times10^5$/ml) and labeled with a red-fluorescent probe is perfused through the chamber using a tachometer-regulated micro-pump (Bioptechs). The flow rate used produces shear forces similar to that recorder in bone marrow microvessels in vivo (Mazo et al., 10998, J. Exp. Med. 188:465) and comprised between 0.1 and of 10 dyne/cm$^2$, calculated as described (Kerfoot et al., 2003, Eur. J. Immunlol. 33:729).

After allowing the cells to flow in the chamber for 5 minutes, the perfusion rate is increased to bring the shear force to 10 dynes/cm$^2$, thus washing off loosely and non-adherent cells. Images are stream-acquired every 2 seconds using a CCD MicroMax 1300YHS digital camera (Roper Scientific) connected to an Olympus IX-70 microscope and managed by a computer equipped with the Metamorph/Metafluor software (Molecular Devices). The number of adherent cells is measured by examining ten separate microscopic fields (Shulby et al., 2004, Cancer Res. 64:4693), either in the presence or absence of each putative $CX_3CR1$ antagonist to be tested, which is incubated with HBMEs for 30 minutes prior perfusion of the cells in the chamber.

(b) Migration and Chemotaxis

Fluorescent MDA-231 breast cancer cells are plated on the top of FluoroBlock inserts (8 μm pore diameter, BD Biosciences) at the concentration of $8\times10^4$ per insert. The inserts are then transferred into a 24-well plate. Each well contains serum-free culture medium with or without FKN (50 nM) fields (Shulby et al., 2004, Cancer Res. 64:4693). Cells are then allowed to migrate for 24 hours following their transfer to the 24-well plate. The inserts are examined using a Wallac Victor 2 microplate reader (Perkin Elmer) set to use bottom illumination in order to detect exclusively the cells migrated through the membrane.

(c) Intracellular Signaling

MDA-231 and SKBR3 human breast cancer cells are exposed to 50 nM FKN for different time points and in the absence or presence of the selected compounds to be tested. Total cell lysate is obtained and SDS-polyacrylamide gel electrophoresis and western blot analysis performed as previously described (Russell et al., 2009, Oncogene 28:412; Dolloff et al., 2005, Oncogene 24:6848). Membranes are probed with antibodies targeting phospho-p44/42 MAPK (Thr202/Tyr204), total p44/42 MAPK, phospho-Akt (Ser-473) and total Akt (all from Cell Signaling). All primary antibody incubations are performed overnight at 4° C. Primary antibody binding is detected using horseradish peroxidase-conjugated anti-rabbit secondary antibody (Pierce). Chemiluminescent signals are obtained using SuperSignal West Femto reagents (Pierce) and detected with a Fluorochem 8900 imaging system and relative software (Alpha Innotech).

The potency of each newly synthesized compound tested in blocking $CX_3CR1$ functional activity is measured by calculating its $IC_{50}$ by constructing as dose-response curve. Only compounds displaying $IC_{50}<1$ μM is moved to the next phase, in agreement with the screening criteria previously adopted for receptor binding affinity ($K_i<100$ nM) and selectivity ($K_i>10$ μM).

Example 5: Inhibitory Activity of Potential $CX_3CR1$ Antagonists on the Metastatic Potential of Breast Cancer Cells in Animal Models Compounds are screened for selectivity using a panel of 35 different GPCRs. The bioavailability of each compound is established and its potential toxicity for brain tissue investigated. Pharmacokinetic (PK) studies identify loading doses and interdose plasma concentrations to be used in the subsequent animal studies. Two different animal models of metastatic dissemination are employed, and either immune-compromised or immune-competent mice will be used.

(a) Selectivity

The custom-assembled platform includes 35 different GPCRs, which will be selected among non-peptide receptors (Adenosine, Dopamine, Cannabinoids, etc) and peptide receptors (Angiotensin-II, Bradykinin, Endothelin, etc). The newly synthesized antagonists of $CX_3CR1$ that pass the multiple screening phases described above are analyzed and moved to the next phase only if showing a 1000× selectivity for $CX_3CR1$ over any of the 35 GPCRs included in the custom testing platform.

(b) Pharmacokinetics

New compounds deemed promising enough are screened in a mouse pharmacokinetic assay to determine the bioavailability, plasma concentration, and brain/plasma exposure. This analysis provides in-life observation on each mouse, plasma concentrations at each time point of the assay, relative bioavailability (% F) based on the AUC (area under the IV versus PO curve) for each test compound and concentration versus time profiles. The appropriate pharmacokinetic parameters is obtained including the $C_{max}$ and $T_{max}$ for each compound, in addition to half-life, clearance, and volume of distribution after IV administration.

For this study, conscious, fasted, female CD-1 mice with a body weight between 20 and 35 grams are used. Three mice are used for time point, 21 mice for IV dose route and 18 mice for PO dose route. Sample blood will be collected by cardiac puncture.

In addition to further establish the drug-like properties of the newly synthesized antagonists of $CX_3CR1$, this study provides crucial information for the execution of the experiments in the animal models of metastatic dissemination. For instance, for each compound the following parameters will be identified: the loading doses to bring plasma concentrations to steady state that are to be used in the next steps; and the average interdose plasma concentrations to extrapolate the maintenance doses that are to be used in the next steps.

(c) Brain Toxicity

The $CX_3CR1$ receptor is expressed by microglia, the resident inflammatory cells of the Central Nervous System (CNS). It has been shown that altering $CX_3CR1$ expression and/or functioning dysregulates microglia responses and induces neurotoxicity (Cardona et al., 2006, Nat. Neurosci. 9:917). Thus, penetration of the CNS by $CX_3CR1$ antagonists could produce serious toxic effects. These concerns would be partially addressed by comparing the structures of newly synthesized $CX_3CR1$ antagonists with molecules with well known high-permeability for the Blood Brain Barrier (BBB), such as imipramine and baclofen. In addition, mice matched for age and weight to those used for our in vivo metastasis models are administered with the compounds to be tested and the resulting concentrations in CNS tissue and cerebrospinal fluid measured by LC-MS/MS analysis. A brain/plasma exposure ratio <0.1 is considered the minimal requisite for each $CX_3CR1$ antagonist to be advanced to in vivo testing.

Finally, to rule out the possibility that the growth of a primary tumor and/or the presence of metastatic disease could induce systemic conditions capable of altering the BBB permeability and allowing access of $CX_3CR1$ antagonists to CNS, mice are examined for macroscopic alteration of brain morphology, loss of neuronal cells and signs of diffuse inflammation.

(d) Dissemination of Cancer Cells Through Haematogenous Route

Figure 13:
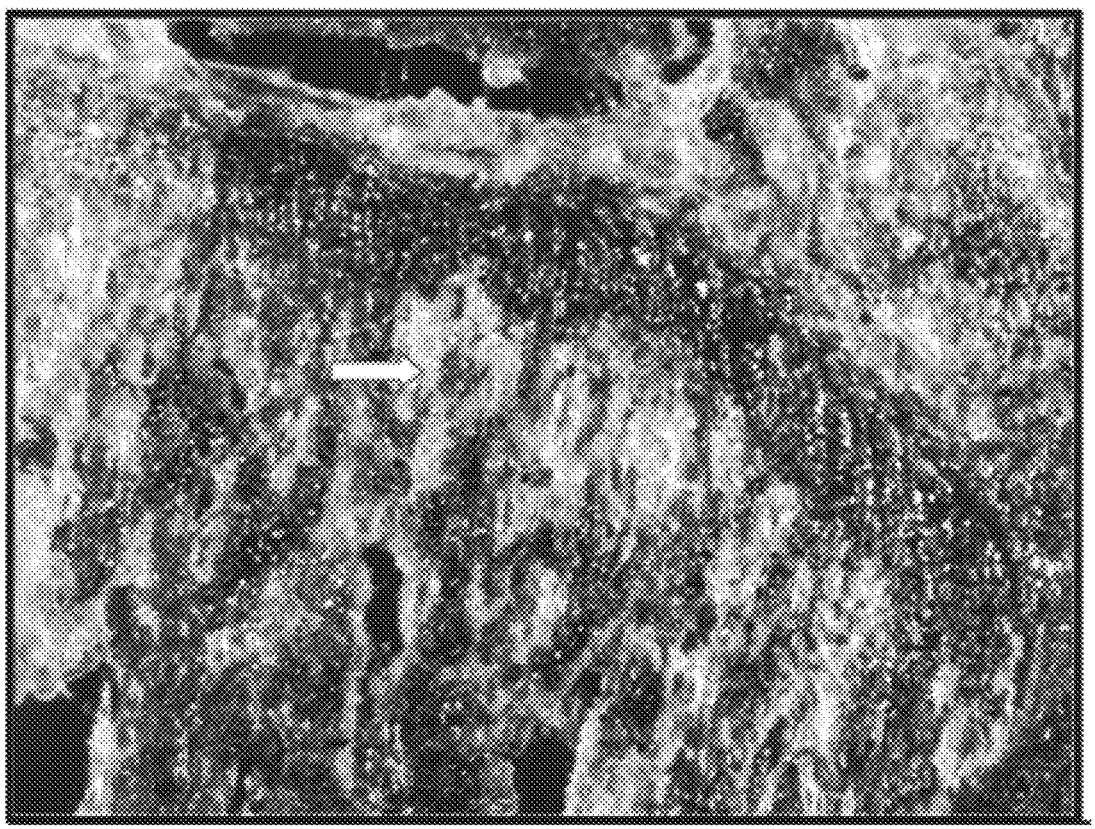
FIG. 13 illustrates fluorescent cancer cells detected in the tibia of a SCID mouse, 72 hours after being inoculated into the blood circulation via the left cardiac ventricle.

MDA-231 human breast cancer cells stably expressing eGFP are inoculated in the left cardiac ventricle of immunocompromised SCID mice (CB17-SCRF, 6 weeks, female, ~35 g body weight). A suspension of $5 \times 10^4$ fluorescent cells/100 µl is delivered using a 27-gauge needle in animals previously anesthetized with 100 mg/kg ketamine and 20 mg/kg xylazine (Russell et al., 2010, Cancer Res. 70:4195; Dolloff et al., 2007, Cancer Res. 67:555). Different organs are collected, processed for cryosectioning and serial sections of 80 µm in thickness inspected with a fluorescence stereomicroscope. Single cancer cells in the lower femur and upper tibia, frequently bilaterally, may be consistently detected in >80% of animals euthanized at either 24 or 72 hours post-inoculation (FIG. 13). If animals are allowed to progress through the study, these cells produce macroscopic bone metastases within 4 weeks. Single cells may also be identified in the lungs and adrenal glands soon after their inoculation; however, these cells eventually disappear and fail to produce tumors, an indication that their ability to adhere and extravasate to these organs is not equaled by the potential to survive and proliferate. Thus, this part of the study focuses mostly on the inhibitory effect of $CX_3CR1$ antagonists on the adhesion and extravasation of breast cancer cells to the skeleton. Since at 72 hours post-inoculation most of the cells arrived to the bone marrow sinusoids have extravasated into the surrounding stroma (Muller et al., 2001, Nature 410:50), this time-point is used for the following experiments. Each antagonist is administered to mice immediately before the inoculation of cancer cells and at the loading dose extrapolated by the PK experiments described herein.

(e) Statistical Power and Sample Calculation

The evaluation of reduced bone metastatic potential by $CX_3CR1$ antagonists requires sample size calculation. A reduction of at least 50% or more in number of cells disseminated to the skeleton (and possibly other sites) is considered a significant impairment of bone-metastatic potential.

Considering a desired power of 0.80, a significance level ($\alpha$) of 0.05, a difference in population mean ($\delta$) of 50 and a standard deviation ($\sigma$) of 50, the sample size calculated for these experiments equals to 15 mice, which corresponds to 5 mice per experiments and three total cellinoculation experiments to be conducted. If testing up to nine newly synthesized antagonists, these experiments require $15 \times 9 = 135$ mice. Control experiments also require fifteen mice and this sub-aim will then require 150 mice in total.

(f) Dissemination and Metastasis of Breast Cancer Cells from the Mammary Fat Pad The tumorigenic and metastatic abilities of human cancer cells must be investigated in immunocompromised animal models (Welch, 1997, Clin. Exp. Metastasis 15:272). However, this approach might fail to address the possibility that in the study the immune system of the animals receiving the cancer cells is affected by the administration of $CX_3CR1$ antagonist. Based on the evidence that this receptor is involved in the trafficking of leukocytes and lymphocytes, it is appropriate to establish the anti-metastatic effect of each newly synthesized antagonist both in immune-compromised and immune-competent mice.

i. Immuno-Compromised Animals

Figure 14:
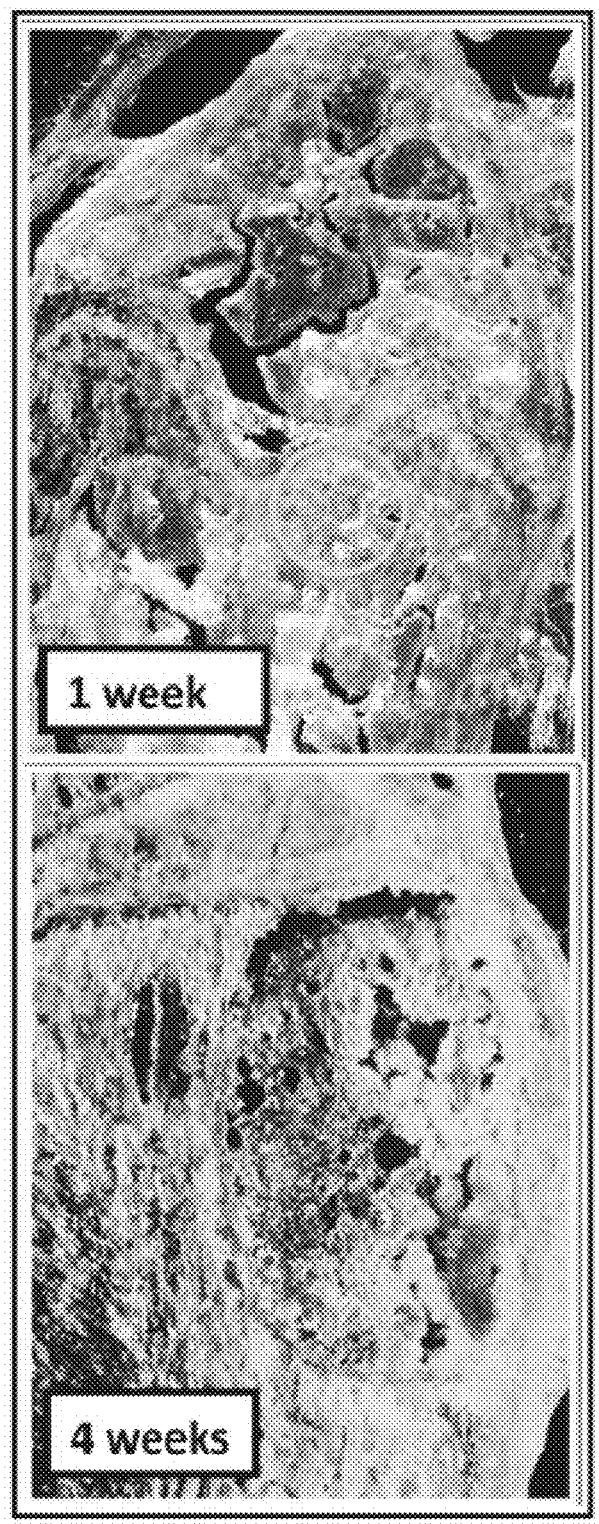
FIG. 14 is a picture illustrating bone metastatic tumors of different size and stage of progression produced by human fluorescent cancer cells in SCID mice, identified by fluorescence stereomicroscopy of bone cryo-sections.

Fluorescent MDA-231 breast cancer cells are grafted into the fourth nipple area of 8-week female SCID mice, as a suspension of $1 \times 10^4$ cells in 100 µl of serum-free DMEM. Animals are inspected for palpable tumors and weighted starting from the fifth day post-inoculation. Inoculated mice receive a dose of the antagonist for the entire duration of the experiments, starting from the day of cellinoculation and based on the information on interdose plasma concentrations extrapolated from the PK analysis performed above. After 4 weeks animals are euthanized and femora, tibiae, lungs, adrenal glands and brain are collected. Tissues are processed for cryosectioning and inspected for single cancer cells, small foci and macroscopic secondary tumors (FIG. 14).

ii. Immuno-Competent Animals

Fluorescent 4T-1 murine breast cancer cells are inoculated in the fourth nipple of 8-week female Balb/C mice, as a suspension of $7 \times 10^3$ cells in 100 µl of serum-free DMEM. The administration of $CX_3CR1$ antagonists and the processing of different tissues at the end of the 4-week experiments is conducted as described above for SCID mice.

In a second set of experiments the primary tumor produced by the inoculation of 4T-1 cells in the mammary fat pad is resected. This approach is conventionally used to extend the time during which 4T-1 cells can metastasize before tumor burden is reached. This procedure also, at least partially, simulates the scenario normally observed in the clinic after surgical excision of primary breast cancer.

Also, in these experiments the animals are treated with CX$_3$CR1 antagonist for the entire duration of the experiments, which use overall survival as endpoint. Thus, animals are inoculated with cancer cells in the mammary fat pad and the tumors are surgically removed after three weeks. Mice are euthanized when the recurring primary mammary tumor exceeds 1.5 cm in diameter or they become moribund for diffuse metastatic disease. Different organs are collected and inspected for secondary tumors as described above.

(g) Measurement of Metastatic Tumors

Bright-field and fluorescence images of tissue cryosections are acquired using a SZX12 Olympus stereomicroscope coupled to an Olympus DT70 CCD color camera. Digital images will be then analyzed with ImageJ software at (http colon double forward slash.rsb.info.nih.gov forward slash ij forward slash) and calibrated by obtaining a pixel to millimeter ratio. The largest cross-section for each metastasis is identified; its relative length and width (perpendicular and centered relative to one another) measured and total area calculated using the ellipse formula: l×w×3.14.

(h) Statistical Analyses, Power and Sample Calculation.

The same power and sample calculations described above is be used for the experiments included herein. For each of the three sets of experiments 150 mice are used (15 mice ×9 antagonists in addition to 15 control mice), for a total number of 450 mice. Number and size of skeletal metastases between groups are analyzed using a two-tailed Student's t-test. Statistical significance between multiple groups is established using a one-way ANOVA, followed by Tukey's Multiple Comparison Test. A value of P≤0.05 is considered statistically significant. Kaplan-Meyer graphs represent data on overall survival.

Figure 15:
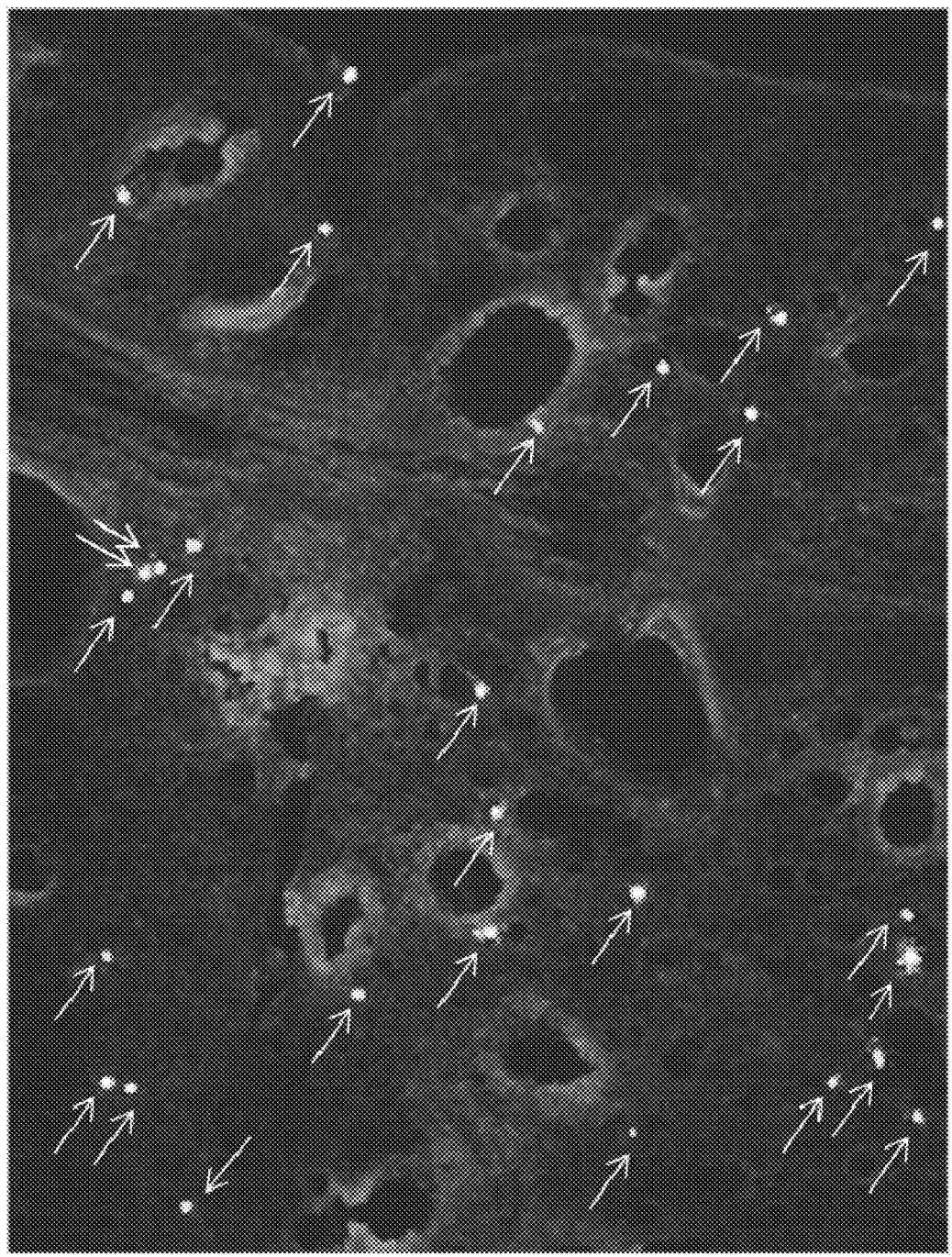
FIG. 15 is a picture illustrating the presence of fluorescent beads (shown as light circles and indicated by arrows) in the examined organs used to confirm the correct execution of cancer cell inoculation in the blood circulation on animal models.

Single cancer cells may be detected immediately after their arrest to secondary organs, and the skeleton in particular. This study greatly benefits from this powerful approach. However, it is imperative to validate each intracardiac inoculation to confirm that the absence of disseminated cancer cells is not due to misinjection. To this end, cancer cells are coinjected with blue-fluorescent polystyrene beads (10 μm in diameter, Invitrogen) (FIG. 15). As these beads are carried by the blood flow in the capillary bed of all organs, their absence in the examined tissues will induce the removal of that specific animal from the study.

Example 6: Functional Mutants of CX$_3$CR1 Receptor

Figure 16A:
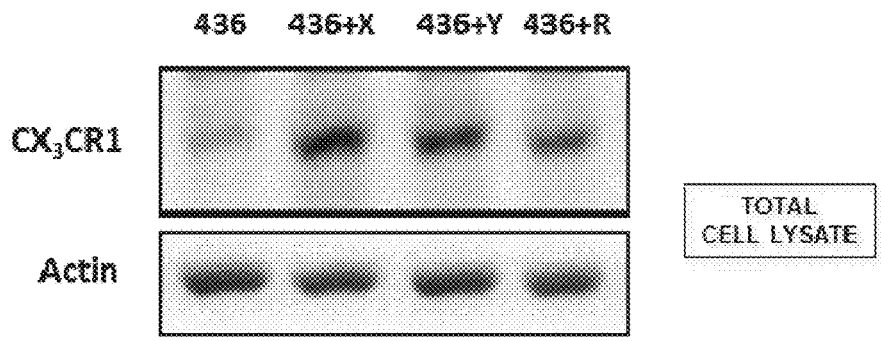
FIGS. 16A-16B illustrate exogenous expression of wild type and functional mutants of the $CX_3CR1$ receptor in MDA-436 breast cancer cells. Western blotting analysis of total cell lysates collected from parental MDA-436 cells as well as cells stably expressing the wild type $CX_3CR1$, the adhesion-impaired Y14F mutant or the chemotaxis-impaired R128N mutant of the receptor was performed. Actin was used as a loading control (FIG. 16A); the correct insertion of each exogenously expressed form of the $CX_3CR1$ receptor on the plasma membrane of transfected MDA-436 cells was confirmed by cell surface protein isolation (FIG. 16B). Actin detected in the cytosolic fraction was used as a loading control.
Figure 16B:
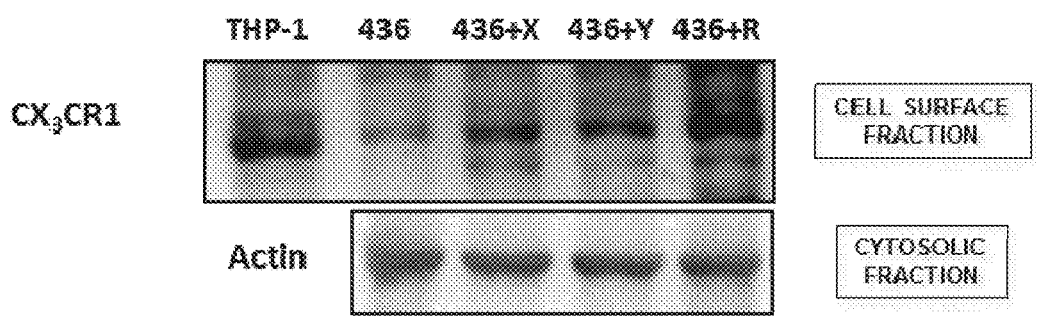

Experiments were conducted with MDA-436 cells stably expressing either the wild-type form of CX$_3$CR1 or one of the two following functional mutants of this receptor. The first mutant was generated by inducing a tyrosine to phenylalanine mutation at amino acid 14 of the first extracellular domain of CX$_3$CR1 (Y14F) (Fong et al., 2002, J. Biol. Chem 277:19418-23). This mutant was previously characterized for its failure to firmly bind to FKN, most likely because of the inability of phenylalanine to be sulfated, a modification that enhances the binding to this chemokine. Although defective in capture and adhesion, CX$_3$CR1 (Y14F) is competent in signal transduction, but with a 100-fold decreased affinity to immobilized FKN (Fong et al., 2002, J. Biol. Chem 277:19418-23). The specific involvement of CX$_3$CR1 in extravasation was evaluated using a second functional mutant containing an arginine to asparagine mutation at amino acid 128, which is located in the second intracellular loop of CX$_3$CR1 and in the highly conserved aspartic acid-arginine-tyrosine (DRY) sequence of G-protein coupled receptor. Chemoattractant properties of chemokine receptors are dependent on G-protein activation and subsequent ability to transduce downstream signals following stimulation by the appropriate ligand. As the DRY sequence is required for G-protein activation, the R-to-N mutation makes the receptor incompetent of intracellular signaling and cells expressing the CX$_3$CR1 (R128N) mutant do not migrate toward FKN, while showing normal binding/adhesion to this chemokine (Haskell et al., 1999, J. Biol. Chem. 274:10053-58). The expression of wild type and mutated forms of CX$_3$CR1 by MDA-436 cells was verified by western blotting performed on total cell lysates (FIG. 16A). In addition, the insertion of each form of the receptor at the plasma membrane of transfected cells was confirmed by isolation of cell surface proteins obtained by biotinylation (FIG. 16B).

Example 7: Evaluation of CX$_3$CR1 Antagonists on the Homing of Cancer Cells to the Skeleton and Soft-Tissue Organs Via Haematogenous Circulation Human breast cancer cells are inoculated in the left cardiac ventricle of immune-compromised SCID mice (CB17-SCRF, 6 weeks, female, ~25 g body weight). To allow the identification of disseminated cells by microscopic inspection, cells are engineered to stably express enhanced Green Fluorescent Protein (EGFP) using a lentiviral vector from America Pharma Source (Bethesda, Md.). Transduced cells are then enriched for EGFP expression by flow cytometry and sorting before being used for the in vivo experiment.

A suspension of 25×10$^4$ fluorescent cells/100 ml is delivered using a 30-gauge needle in animals previously anesthetized with 100 mg/kg ketamine and 20 mg/kg xylazine. The correct execution of intracardiac inoculation is established by the appearance of fresh arterial blood in the Luer-Lok fitting of the hypodermic needle, which indicates the successful penetration of the ventricular wall. In addition, blue-fluorescent polystyrene beads (10 mm diameter, Invitrogen-Molecular Probes) are routinely co-injected with cancer cells. Their detection by fluorescence microscopy in different organs at necropsy is used to confirm the successful inoculation in the blood circulation.

Different organs are collected and processed for cryosectioning as follows: Tissues are fixed in 4% Formalin for 48 hours, decalcified in 0.5 M EDTA if necessary and frozen in O.C.T. embedding medium (Electron Microscopy Sciences, Hatfield, Pa.). Serial tissue sections of 80 μm in thickness are obtained using a Microm HM550 cryostat (Mikron, San Marcos, Calif.). Sections of each hind leg and soft-tissue organs are transferred to glass slides, stored at −20° C. and examined for the presence of disseminated cancer cells using an Olympus IX50 fluorescence microscope connected to a Nuance spectral microscopy system (CRI).

Using this approach single cancer cells are consistently detected in bone and soft-tissue organs in >90% of animals euthanized at either 24 or 72 hours post-inoculation.

Control group: mice receive 100 ml of a saline solution via the intraperitoneal route (IP) 20 to 30 minutes prior to being inoculated with cancer cells via the intracardiac route (IC).

Antagonist group: mice receive 100 ml of a saline solution IP containing each compound dissolved in DMSO, 20 to 30 minutes prior to being inoculated with cancer cells. The final dose of compound is equal to 50 mg/Kg and final concentration of DMSO is 5%.

Example 8: Evaluation of CX$_3$CR1 Antagonists on the Chemotactic Migration of Cancer Cells Fluorescent human cancer cells stably expressing EGFP are plated on the inserts of the BD Falcon Fluoroblock System (upper chamber). This system provides a platform to monitor migration of fluorescent cells using a plate reader.

The bottom of each insert is made of a light-opaque PET microporous membrane that absorbs fluorescence within the 490-700 nm range. The illumination of this membrane from the bottom using a plate reader allows detecting only fluorescent cells that have migrated through the membrane towards a given chemoattractant substance located in the lower chamber of the Fluoroblock system.

Human cancer (1×10$^5$) are plated in each insert and allowed to adhere to the membrane overnight and in the absence of control or chemoattractant solution in the lower chamber.

The migration experiment is started by adding either serum-free culture medium as control or the same medium containing the chemokine fractalkine (1 to 50 nM) to the lower chamber of the migration system. The potential inhibitory effect of each CX$_3$CR1 antagonist to be screened is tested by adding the compound (1 nM-1 mM) to the cells in the upper chamber.

The plate reader is set to 485 nm for excitation and 510 nm for emission. Emitted fluorescence is measured at time 0 as well as at 1, 3 and 6 hours and subtracted of background signal acquired by measuring emitted fluorescence in the absence of cells in the upper chamber and solution in the lower chamber.

Example 9: 5-(3-(4-(4-Chlorophenyl)-4-hydroxypiperidin-1-yl)propyl)pyrrolo[1,2-a]quinoxalin-4(5H)-one—Compound 3

5-(3-chloropropyl)pyrrolo[1,2-a]quinoxalin-4(5H)-one

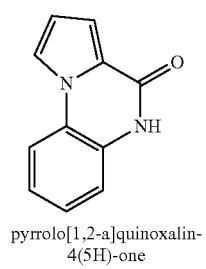

pyrrolo[1,2-a]quinoxalin-4(5H)-one

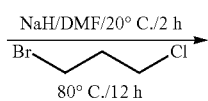

NaH/DMF/20° C./2 h
Br⌒⌒⌒Cl
80° C./12 h

Pyrrolo[1,2-a]quinoxalin-4(5H)-one (500 mg; 2.71 mmol) was dissolved in anhydrous DMF (10 mL) in a 25 mL round bottomed flask. NaH (68.6 mg; 2.71 mmol; 95%) was carefully added to the flask under a blanket of nitrogen. The reaction mixture was allowed to react for 2 h at room temperature after which 1-bromo-3-chloropropane (511.99 mg, 3.25 mg) was added and the mixture was heated to 80° C. overnight. The reaction mixture was diluted with ethyl acetate and washed with H$_2$O, brine, dried over sodium sulfate, then filtered and concentrated. The crude mixture was purified by flash chromatography to yield the desired 5-(3-chloropropyl)pyrrolo[1,2-a]quinoxalin-4(5H)-one and 5-(3-bromopropyl)pyrrolo[1,2-a]quinoxalin-4(5H)-one in approximately a 60:40 ratio. The mixture was used in the next step without further purification. [M+1]$^+$=261 Chloride; [M+1]$^+$=305 Bromide. $^1$H NMR (CDCl$_3$): δ 2.18-2.42 (2H); 3.49-3.62 (1H); 3.63-3.81 (1H); 4.38-4.50 (2H); 6.61-6.71 (1H); 7.13-7.514 (4H); 7.65-7.80 (2H).

5-(3-(4-(4-Chlorophenyl)-4-hydroxypiperidin-1-yl)propyl)pyrrolo[1,2-a]quinoxalin-4(5H)-one

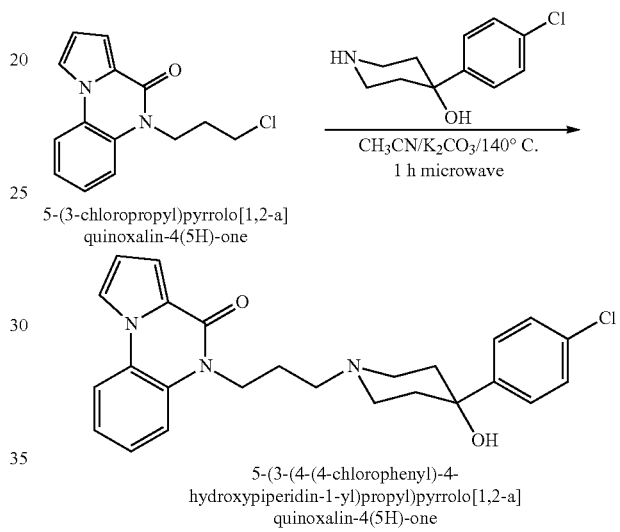

5-(3-chloropropyl)pyrrolo[1,2-a]quinoxalin-4(5H)-one 5-(3-(4-(4-chlorophenyl)-4-hydroxypiperidin-1-yl)propyl)pyrrolo[1,2-a]quinoxalin-4(5H)-one 5-(3-chloropropyl)pyrrolo[1,2-a]quinoxalin-4(5H)-one (100 mg; 0.38 mmol) was added to a 5 mL microwave vessel containing a magnetic stir bar. 4-(4-Chlorophenyl)piperidin-4-ol (89.3 mg; 0.42 mmol), potassium carbonate (78.77 mg; 0.57 mmol), and 2 mL of acetonitrile were added to the vessel. The vessel was sealed and heated to 140° C. for 1 hour, after which the solvent was evaporated and the reaction mixture was purified by flash chromatography to yield 5-(3-(4-(4-chlorophenyl)-4-hydroxypiperidin-1-yl)propyl)pyrrolo[1,2-a]quinoxalin-4(5H)-one (48.5 mg; 0.11 mmol; 29%). [M+1]$^+$=436.

Example 10: 5-(3-(4-(4-chlorophenyl)piperidin-1-yl)propyl)pyrrolo[1,2-a]quinoxalin-4(5H)-one—Compound 4

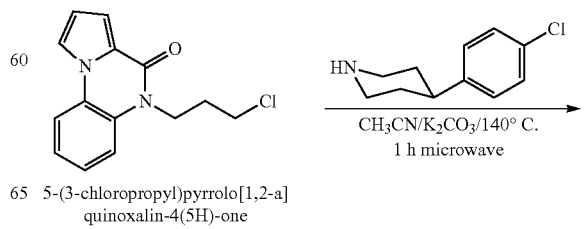

5-(3-chloropropyl)pyrrolo[1,2-a]quinoxalin-4(5H)-one

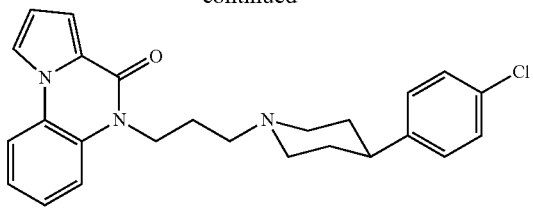

5-(3-(4-(4-chlorophenyl)piperidin-1-yl)
propyl)pyrrolo[1,2-a]quinoxalin-4(5H)-
one 5-(3-chloropropyl)pyrrolo[1,2-a]quinoxalin-4(5H)-one (100 mg; 0.38 mmol) was added to a 5 mL microwave vessel containing a magnetic stir bar. 4-(4-chlorophenyl)piperidine (82.8 mg; 0.42 mmol), potassium carbonate (78.77 mg; 0.57 mmol), and 2 mL of acetonitrile were added to the vessel. The vessel was sealed and heated to 140° C. for 1 hour, after which the solvent was evaporated and the reaction mixture was purified by flash chromatography to yield 5-(3-(4-(4-chlorophenyl)piperidin-1-yl)propyl)pyrrolo[1,2-a]quinoxalin-4(5H)-one (110 mg; 0.26 mmol; 70%) $[M+1]^+=420$.

Example 11: Agonist and Antagonist Activity Against the Human CX3CR1 Receptor Using Calcium Mobilization ($Ca^{2+}$) Assay Material Cells: Mammalian HEK293T cells stably expressing human CX3CR1 (Multispan, Hayward, Calif.)—Host cell: HEK293T; Transfection: Expression vector containing full-length human CX3CR1 cDNA (GenBank Accession Number NM_001337) with FLAG tag sequence at N-terminus; Propagation Medium: DMEM, 10% FBS, 1 µg/mL puromycin.

Compounds were reconstituted in DMSO at 10 mM. Control agonist CX3CL1 was from Peprotech (Cat #300-31). Calcium assay kit was Screen Quest™ Fluo-8 No Wash kit (AAT Bioquest, Cat #36315), and instrument was FlexStation III (Molecular Devices).

Methods

Calcium assay: Cells expressing the CX3CR1 receptor were transiently transfected with the chimeric G protein Gαqi5 and seeded in 384-well plates at appropriate densities and cultured overnight. Calcium assays were conducted according to the manufacturer's protocols. The calcium dye loading buffer was added to the cells and incubated for one hour at 37° C. Calcium flux was monitored for 90 seconds with compound injected into the wells at 20th second. In antagonist mode, carrier or compounds were preincubated with the cells for 30 minutes before calcium flux measurement with the control agonist at $EC_{80}$ concentration (0.04 µM).

Figure 17:
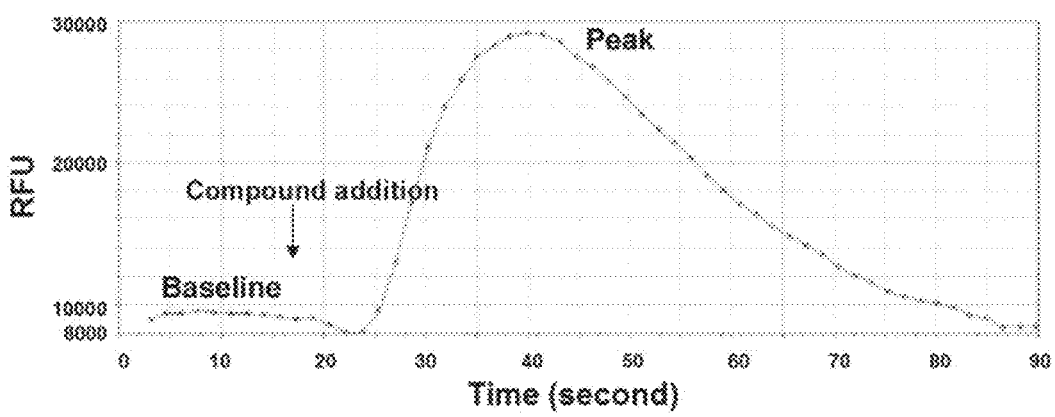
FIG. 17 is a graph illustrating sample calcium flux trace and signal calculation.

Data analysis: Calcium assay results were expressed as "RFU" and "% Increase in RFU" (FIG. 17). Data were represented in Mean±SEM. Dose-response curves were fitted using "Sigmoidal dose-response (variable slope)" function in Prism 4 without constraint. $EC_{50}$, $EC_{80}$ and $IC_{50}$ values were derived from "% Increase in RFU".

Discussion

Figure 18A:
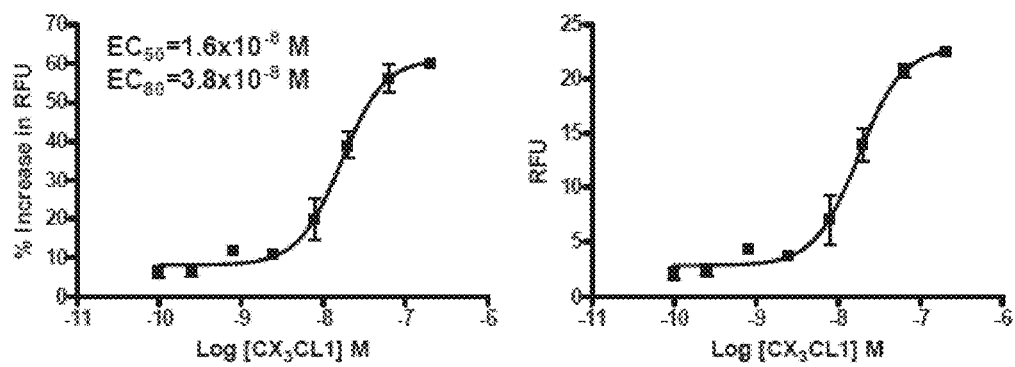
FIGS. 18A-18C are a series of graphs illustrating calcium assay results.
Figure 18B:
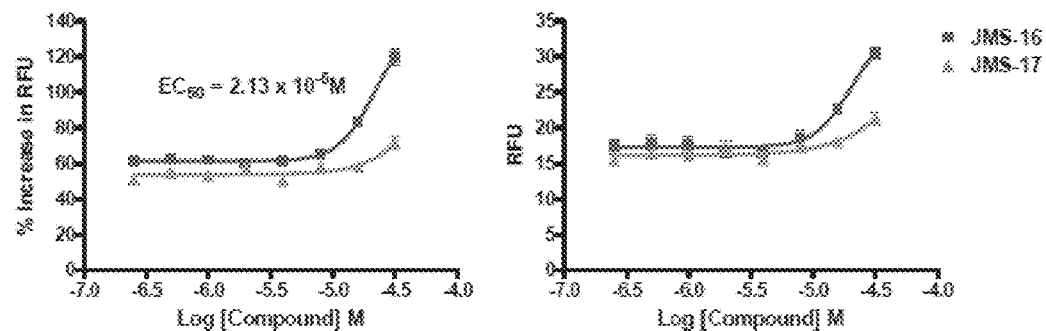
Figure 18C:
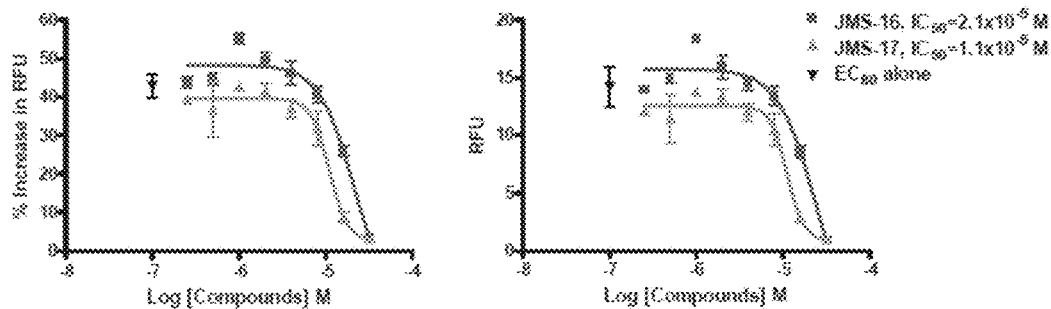

Control compound CX3CL1 displayed dose-dependent stimulation of calcium flux in CX3CR1-expressing cells with an expected $EC_{50}$ value (FIG. 18A). Compound 3 (labeled as JMS-16) showed agonist activity at the two highest concentrations while compound 4 (labeled as JMS-17) did not have agonist activity (FIG. 18B). Compounds 3 and 4 inhibited CX3CL1-evoked calcium flux with $IC_{50}$ values of 21 µM and 11 µM, respectively (FIG. 18C). The antagonist activity with Compound 3 could be due to desensitization of the receptor during pre-incubation since it had agonist activity.

Compound 3 was shown to have a p-ERK1/2 inhibition $EC_{50}$ of ~10 nM by Western blot analysis. Compound 5 was shown to have a p-ERK1/2 inhibition $EC_{50}$ of ~5 nM by Western blot analysis.

The following tables summarize the raw data for the experiments.

Control Agonist

| Log [$CX_3CL1$] M | % Increase in RFU | | RFU | |
|---|---|---|---|---|
| −10.0 | 7.6 | 4.7 | 2.6 | 1.6 |
| −9.6 | 8.3 | 5.1 | 2.9 | 1.9 |
| −9.1 | 12.2 | 11.0 | 4.4 | 4.1 |
| −8.6 | 9.6 | 11.8 | 3.3 | 4.0 |
| −8.1 | 25.3 | 14.3 | 9.3 | 4.8 |
| −7.7 | 42.3 | 35.6 | 15.5 | 12.4 |
| −7.2 | 59.9 | 52.7 | 21.4 | 20.1 |
| −6.7 | 59.0 | 61.1 | 22.2 | 22.7 |

Agonist Mode

| Log [Compounds] M | % Increase in RFU | | | | | | RFU | | | | | |
|---|---|---|---|---|---|---|---|---|---|---|---|---|
| | JMS-16 | | | JMS-17 | | | JMS-16 | | | JMS-17 | | |
| −4.5 | 127.9 | 118.0 | 112.4 | 77.7 | 72.3 | 65.1 | 31.7 | 30.7 | 29.0 | 23.0 | 20.7 | 20.2 |
| −4.8 | 80.2 | 85.0 | 84.7 | 58.0 | 60.8 | 54.8 | 22.1 | 22.5 | 23.3 | 17.1 | 19.2 | 17.8 |
| −5.1 | 60.1 | 70.3 | 64.9 | 59.6 | 61.5 | 52.9 | 16.5 | 20.3 | 18.8 | 17.3 | 16.8 | 17.5 |
| −5.4 | 61.1 | 62.3 | 60.5 | 52.6 | 50.9 | 47.5 | 15.5 | 16.9 | 17.1 | 15.5 | 15.8 | 15.2 |
| −5.7 | 57.2 | 61.7 | 60.7 | 57.2 | 63.4 | 50.6 | 15.2 | 17.8 | 17.1 | 17.2 | 18.7 | 15.9 |
| −6.0 | 58.3 | 63.2 | 63.0 | 55.8 | 53.7 | 49.4 | 15.6 | 18.7 | 18.6 | 16.5 | 15.7 | 15.9 |
| −6.3 | 59.0 | 66.2 | 61.9 | 59.0 | 59.9 | 47.4 | 16.0 | 18.2 | 19.5 | 17.7 | 17.0 | 14.8 |
| −6.6 | 61.6 | 62.1 | 60.1 | 52.7 | 51.8 | 48.0 | 15.5 | 18.6 | 17.8 | 16.0 | 15.5 | 14.8 |

Antagonist Mode

| Log [Compounds] M | % Increase in RFU | | | | | | RFU | | | | | |
|---|---|---|---|---|---|---|---|---|---|---|---|---|
| | JMS-16 | | | JMS-17 | | | JMS-16 | | | JMS-17 | | |
| −4.5 | 4.4 | 3.5 | 2.2 | 2.1 | 4.4 | 3.1 | 1.2 | 0.9 | 0.6 | 0.7 | 1.3 | 1.0 |
| −4.8 | 27.9 | 23.6 | 26.7 | 11.1 | 7.0 | 8.3 | 9.5 | 7.6 | 8.5 | 3.5 | 2.3 | 2.7 |
| −5.1 | 45.0 | 38.6 | 38.7 | 39.8 | 31.5 | 24.2 | 15.0 | 13.0 | 12.3 | 13.2 | 9.5 | 8.6 |
| −5.4 | 52.1 | 45.7 | 41.1 | 41.9 | 36.0 | 33.2 | 15.5 | 14.4 | 13.5 | 13.5 | 11.8 | 10.7 |
| −5.7 | 48.9 | 53.1 | 47.0 | 41.9 | 44.7 | 38.4 | 15.6 | 17.9 | 14.4 | 13.8 | 14.3 | 12.2 |
| −6.0 | 58.1 | 54.8 | 53.3 | 43.1 | 44.1 | 41.5 | 18.4 | 18.6 | 18.2 | 14.0 | 14.2 | 13.2 |
| −6.3 | 46.4 | 46.2 | 42.0 | 40.2 | 47.0 | 23.2 | 15.7 | 14.6 | 14.5 | 13.0 | 14.1 | 7.2 |
| −6.6 | 45.9 | 41.3 | 44.0 | 39.9 | 40.6 | 37.8 | 13.6 | 14.0 | 14.4 | 12.7 | 12.3 | 11.4 |
| $EC_{80}$ $CX_3CL1$ | 45.9 | 37.2 | 45.8 | 45.9 | 37.2 | 45.8 | 16.0 | 10.9 | 15.8 | 16.0 | 10.9 | 15.8 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound of Formula (IX):

$$R^A\text{—}R^B \quad (IX)$$

wherein:

$R^A$ is selected from the group consisting of:

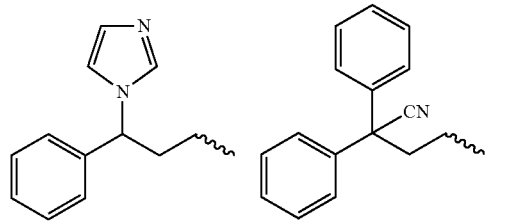

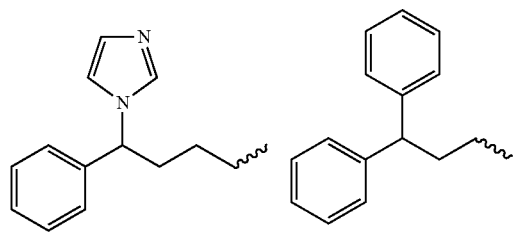

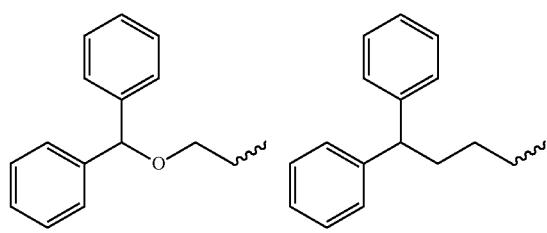

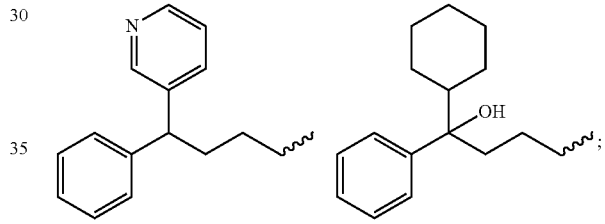

and $R^B$ is selected from the group consisting of:

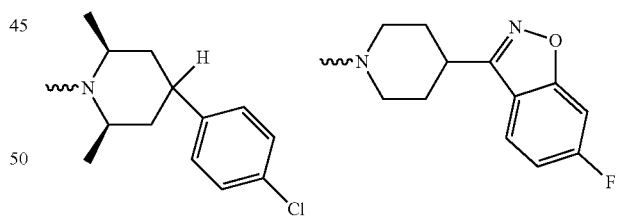

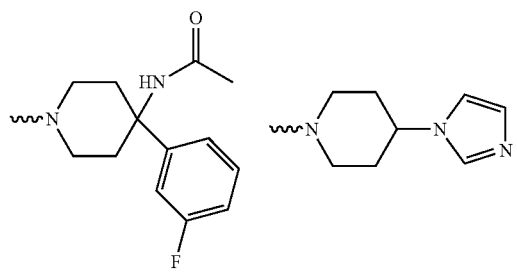

-continued

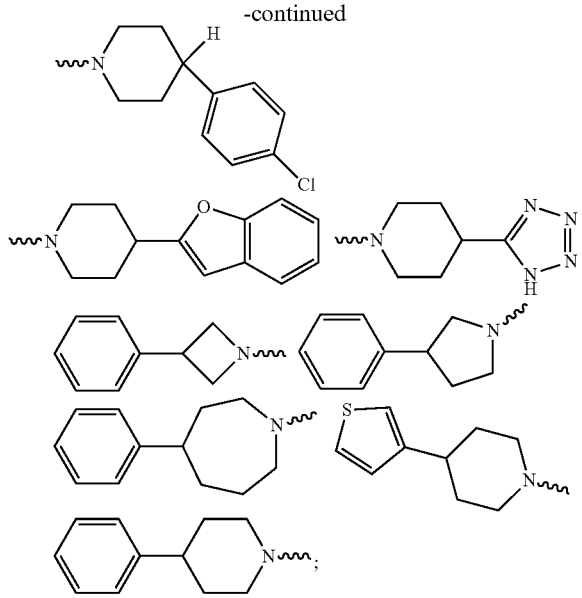

or a pharmaceutically acceptable salt thereof.

2. A pharmaceutical composition comprising a compound of Formula (IX) and at least one pharmaceutically acceptable carrier, wherein the compound of Formula (IX) is:

$$R^A—R^B \quad (IX)$$

wherein:
$R^A$ is selected from the group consisting of:

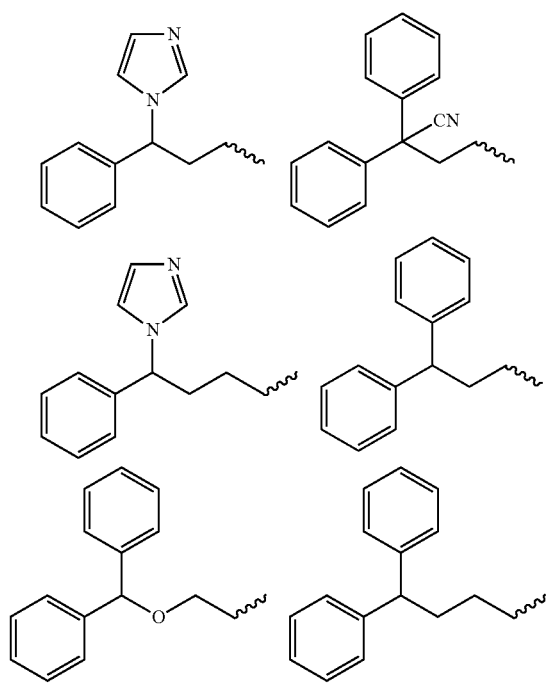

-continued

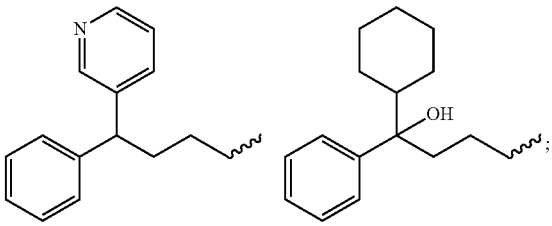

and
$R^B$ is selected from the group consisting of:

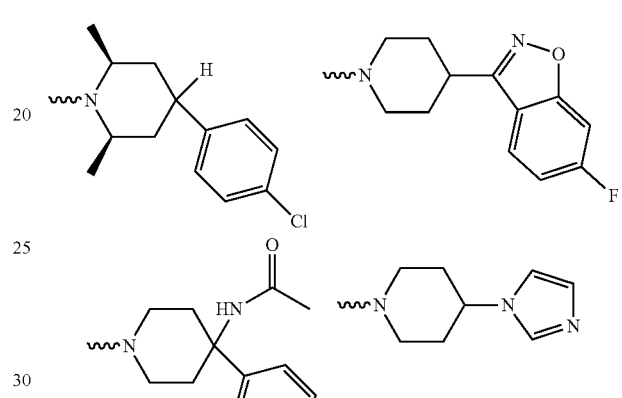

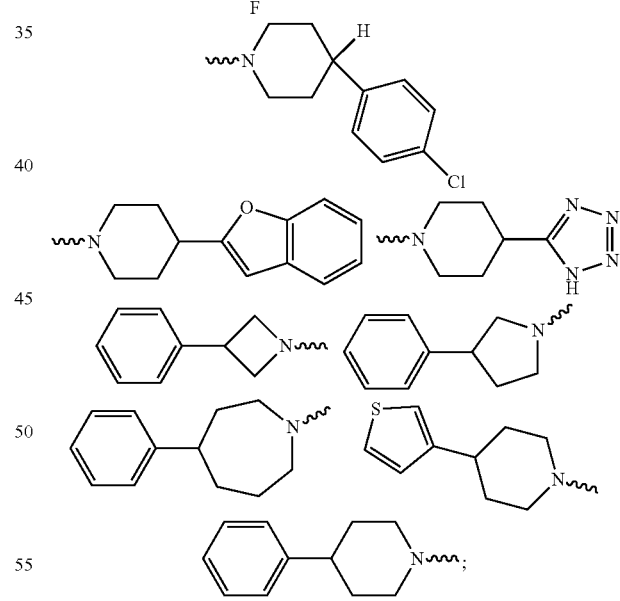

or a pharmaceutically acceptable salt thereof.

* * * * *

SEQUENCE LISTING

```
<160> NUMBER OF SEQ ID NOS: 2

<210> SEQ ID NO 1
<211> LENGTH: 355
<212> TYPE: PRT
<213> ORGANISM: Homo sapiens

<400> SEQUENCE: 1

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
    50                  55                  60

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
                85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
```

-continued

```
                225                 230                 235                 240
        Phe Leu Phe Trp Thr Pro Tyr Asn Val Met Ile Phe Leu Glu Thr Leu
                        245                 250                 255

Lys Leu Tyr Asp Phe Phe Pro Ser Cys Asp Met Arg Lys Asp Leu Arg
                        260                 265                 270

Leu Ala Leu Ser Val Thr Glu Thr Val Ala Phe Ser His Cys Cys Leu
                        275                 280                 285

Asn Pro Leu Ile Tyr Ala Phe Ala Gly Glu Lys Phe Arg Arg Tyr Leu
                        290                 295                 300

Tyr His Leu Tyr Gly Lys Cys Leu Ala Val Leu Cys Gly Arg Ser Val
        305                 310                 315                 320

His Val Asp Phe Ser Ser Glu Ser Gln Arg Ser Arg His Gly Ser
                        325                 330                 335

Val Leu Ser Ser Asn Phe Thr Tyr His Thr Ser Asp Gly Asp Ala Leu
                        340                 345                 350

Leu Leu Leu
                355

<210> SEQ ID NO 2
<211> LENGTH: 397
<212> TYPE: PRT
<213> ORGANISM: Homo sapiens

<400> SEQUENCE: 2

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
                20                  25                  30

Asn Ile Thr Cys Ser Lys Met Thr Ser Lys Ile Pro Val Ala Leu Leu
            35                  40                  45

Ile His Tyr Gln Gln Asn Gln Ala Ser Cys Gly Lys Arg Ala Ile Ile
        50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Leu Glu Pro Thr Pro Ser Ser
                130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
                180                 185                 190

Thr Ala Ala Thr Trp Gln Ser Ser Ala Pro His Gln Pro Gly Pro Ser
            195                 200                 205

Leu Trp Ala Glu Ala Lys Thr Ser Glu Ala Pro Ser Thr Gln Asp Pro
        210                 215                 220

Ser Thr Gln Ala Ser Thr Ala Ser Ser Pro Ala Pro Glu Glu Asn Ala
225                 230                 235                 240
```

```
Pro Ser Glu Gly Gln Arg Val Trp Gly Gln Gly Gln Ser Pro Arg Pro
            245                 250                 255
Glu Asn Ser Leu Glu Arg Glu Glu Met Gly Pro Val Pro Ala His Thr
            260                 265                 270
Asp Ala Phe Gln Asp Trp Gly Pro Gly Ser Met Ala His Val Ser Val
            275                 280                 285
Val Pro Val Ser Ser Glu Gly Thr Pro Ser Arg Glu Pro Val Ala Ser
            290                 295                 300
Gly Ser Trp Thr Pro Lys Ala Glu Glu Pro Ile His Ala Thr Met Asp
305                 310                 315                 320
Pro Gln Arg Leu Gly Val Leu Ile Thr Pro Val Pro Asp Ala Gln Ala
            325                 330                 335
Ala Thr Arg Arg Gln Ala Val Gly Leu Leu Ala Phe Leu Gly Leu Leu
            340                 345                 350
Phe Cys Leu Gly Val Ala Met Phe Thr Tyr Gln Ser Leu Gln Gly Cys
            355                 360                 365
Pro Arg Lys Met Ala Gly Glu Met Ala Glu Gly Leu Arg Tyr Ile Pro
            370                 375                 380
Arg Ser Cys Gly Ser Asn Ser Tyr Val Leu Val Pro Val
385                 390                 395
```